US012264172B2

(12) United States Patent
Metcalf et al.

(10) Patent No.: US 12,264,172 B2
(45) Date of Patent: Apr. 1, 2025

(54) PHOSPHONATE PRODUCTS AND METHODS

(71) Applicant: The Board of Trustees of the University of Illinois, Urbana, IL (US)

(72) Inventors: William W. Metcalf, Savoy, IL (US); Alexander L. Polidore, Urbana, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 18/043,987

(22) PCT Filed: Sep. 2, 2021

(86) PCT No.: PCT/US2021/048904
§ 371 (c)(1),
(2) Date: Mar. 3, 2023

(87) PCT Pub. No.: WO2022/051527
PCT Pub. Date: Mar. 10, 2022

(65) Prior Publication Data
US 2023/0357291 A1 Nov. 9, 2023

Related U.S. Application Data

(60) Provisional application No. 63/181,745, filed on Apr. 29, 2021, provisional application No. 63/075,138, filed on Sep. 5, 2020.

(51) Int. Cl.
*A61K 31/662* (2006.01)
*A01N 57/20* (2006.01)
*C07F 9/38* (2006.01)

(52) U.S. Cl.
CPC ............ *C07F 9/3826* (2013.01); *A01N 57/20* (2013.01)

(58) Field of Classification Search
CPC .................................................... A61K 31/662
See application file for complete search history.

(56) References Cited

U.S. PATENT DOCUMENTS

| | | | |
|---|---|---|---|
| 4,847,017 | A | 7/1989 | Clubley et al. |
| 5,998,332 | A | 12/1999 | Sato et al. |
| 6,046,180 | A | 4/2000 | Jackson et al. |
| 6,384,022 | B1 | 5/2002 | Jackson et al. |
| 6,881,707 | B2 | 4/2005 | Howat et al. |
| 8,969,048 | B2 | 3/2015 | Kozlov et al. |
| 2018/0044703 | A1 | 2/2018 | Hara et al. |
| 2020/0157555 | A1 | 5/2020 | Lira et al. |

FOREIGN PATENT DOCUMENTS

| | | | |
|---|---|---|---|
| CN | 101993455 | A | 3/2011 |
| CN | 104788491 | A | 7/2015 |
| EP | 2479831 | A1 | 7/2012 |
| WO | 1998043987 | A1 | 10/1998 |
| WO | 2011086532 | A1 | 7/2011 |

OTHER PUBLICATIONS

American Chemical Society. Chemical Abstract Service. RN 2763876-62-4. Entered into STN: Apr. 3, 2022. (Year: 2022).*

Sallis, J.D., et al. "Chapter 11: Phosphorylated and Nonphosphorylated Carboxylic Acids." ACS Symposium Series: American Chemical Society. (1991), pp. 150-160. (Year: 1991).*

Asselin et al., "Center Rot of Onion (*Allium cepa*) Caused by Pantoea ananatis Requires pepM, a Predicted Phosphonate-Related Gene," Mol Plant Microbe Interact., 31(12):1291-1300, Dec. 2018.

Davidson et al., "Analogues of Phosphoenolpyruvate. 4.1 Syntheses of Some New Vinyl- and Methylene-Substituted Phosphonate Derivatives," J Org Chem., 45(13):2698-2703, Jun. 1980.

Eliot et al., "Cloning, Expression, andBiochemical Characterization of Streptomyces rubellomurinus Genes Required for Biosynthesis of Antimalarial Compound FR900098," Chem Biol., 15(8):765-770, Aug. 2008.

International Search Report and Written Opinion of the ISA/US in PCT/US2021/048904, dated Feb. 4, 2022, 10pgs.

Ju et al., "Discovery of Phosphonic Acid Natural Products by Mining the Genomes of 10,000 Actinomycetes, " PNAS, 112(39):12175-12180, Sep. 2015.

Ju et al., "Genomics-Enabled Discovery of Phosphonate Natural Products and Their Biosynthetic Pathways," J Ind Microbiol Biotechnol., 41(2):345-356, Feb. 2014.

McFadden et al., "Potential Inhibitors of Phosphoenolpyruvate Carboxylase. 11* Phosphonic Acid Substrate Analogues Derived from Reaction of Trialkyl Phosphites with Halomethacrylates," Aust J Chem., 42(2):301-314, 1989.

Metcalf et al., "Biosynthesis of Phosphonic and Phosphinic Acid Natural Products, "Annu Rev Biochem., 78:65-94, 2009.

Morohoshi et al., "The Plant Pathogen Pantoea ananatis Produces N-Acylhomoserine Lactone and Causes Center Rot Disease of Onion by Quorum Sensing," J Bacteriol., 189(22):8333-8338, Nov. 2007.

(Continued)

*Primary Examiner* — John S Kenyon
(74) *Attorney, Agent, or Firm* — Haukaas Fortius PLLC; Michael Haukaas

(57) ABSTRACT

Here we show that *P. ananatis* produces at least three phosphonates, two of which were purified and structurally characterized. The first, designated pantaphos, was shown to be 2-(hydroxy(phosphono)methyl)maleate; the second, a probable biosynthetic precursor, was shown to be 2-(phosphonomethyl)maleate. Purified pantaphos is both necessary and sufficient for the hallmark lesions of onion center rot. Moreover, when tested against mustard seedlings, the phytotoxic activity of pantaphos was comparable to the widely used herbicides glyphosate and phosphinothricin. Pantaphos was also active against a variety of human cell lines.

6 Claims, 10 Drawing Sheets

Specification includes a Sequence Listing.

(56) References Cited

OTHER PUBLICATIONS

Polidore et al., "A Phosphonate Natural Product Made by Pantoea ananatis is Necessary and Sufficient for the Hallmark Lesions of Onion Center Rot," mBio, 12(1):e03402-3420, Feb. 2021.
Polidore et al., "A Phosphonate Natural Product Made by Pantoea ananatis is Necessary and Sufficient for the Hallmark Lesions of Onion Center Rot," mBio, 12(1):e03402-3420, Feb. 2021, SI.
Shin et al., "Functional Characterization of a Global Virulence Regulator Hfq and Identification of Hfq-Dependent SRNAs in the Plant Pathogen Pantoea ananatis," Front Microbiol., 10(2075):1-19, Sep. 2019.
Stice et al., "Pantoea ananatis Defeats Allium Chemical Defenses With a Plasmid-Borne Virulence Gene Cluster," bioRxiv preprint doi: https://doi.org/10.1101/2020.02.12.945675, Feb. 2020.
Stice et al., "Pantoea ananatis Genetic Diversity Analysis Reveals Limited Genomic Diversity as Well as Accessory Genes Correlated with Onion Pathogenicity," Front Microbiol., 9(184):1-18, Feb. 2018.
Wanner et al., "Molecular Genetic Studies of a 10.9-Kb Operon in *Escherichia coli* for Phosphonate Uptake and Biodegradation," FEMS Microbiol Lett., 100(1-3):133-139, Dec. 1992.
Weller-Stuart et al., "Swimming and Twitching Motility Are Essential for Attachment and Virulence of Pantoea ananatis in Onion Seedlings," Mol Plant Pathol., 18(5):734-745, Jun. 2017.
White et al., "Microbial Metabolism of Reduced Phosphorus Compounds," Annu Rev Microbiol., 61:379-400, 2007.
Woodyer et al., "Heterologous Production of Fosfomycin and Identification of the Minimal Biosynthetic Gene Cluster," Chem Biol., 13(11):1171-1182, Nov. 2006.
Yu et al., "Diversity and Abundance of Phosphonate Biosynthetic Genes in Nature," PNAS, 110(51):20759-20764, Dec. 2013.
Yu et al., "Purification and Characterization of Phosphonoglycans from Glycomyces sp. Strain NRRL B-16210 and Stackebrandtia nassauensis NRRL B-16338," J Bacteriol., 196(9):1768-1779, May 2014.
Bavcon et al., "Photodegradation of organophosphorus insecticides—Investigations of products and their toxicity using gas chromatography-mass spectrometry and AChE-thermal lens spectrometric bioassay," Chemosphere., 67 (1):99-107, Feb. 2007.
Craig et al., "The reaction of sodamide with aß-acetylenic acids and their derivatives," Proc. Chem. Soc., Issue 8, pp. 283-284, Jan. 1, 1962.
Fernandez et al., "Theoretical study of the deposition and adsorption of bisphosphonates on the 001 hydroxyapatite surface: Implications in the pathological crystallization inhibition and the bone antiresorptive action," Applied Surface Science, vol. 392, pp. 204-214, Sep. 13, 2016.
Friedkin et al., "The Synthesis of Phosphomalic Acid," J. Bio. Chem., vol. 169, No. 1, pp. 183-190, Mar. 31, 1947.
Partial Search Report of the European Patent office dated Nov. 11, 2024 in EP Application No. 21865127.1; 18 pgs.
Extended Search Report and Written Opinion of the European Patent Office dated Feb. 3, 2025 in EP Application No. 21865127.1; 15 pgs.

* cited by examiner

A 0.5 mM pantaphos water

PHOSPHONATE PRODUCTS AND METHODS

RELATED APPLICATIONS

This application is a National Stage filing under 35 U.S.C. § 371 of International Application No. PCT/US2021/048904 filed Sep. 2, 2021, which claims the benefit of U.S. Provisional Patent Application No. 63/181,745, filed Apr. 29, 2021, and U.S. Provisional Patent Application No. 63/075,138, filed Sep. 5, 2020, which applications are incorporated herein by reference.

GOVERNMENT SUPPORT

This invention was made with government support under Grant No. R01 GM127659 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 1, 2021, is named 500_127WO1_SL.txt and is 58,914 bytes in size.

BACKGROUND OF THE INVENTION

*Pantoea* species have been recognized as plant pathogens since 1928. These gram-negative Enterobacteriaceae were originally classified as members of the genus *Erwinia*, but were subsequently moved to *Pantoea* based on DNA hybridization experiments. Although many *Pantoea* species are benign or beneficial plant mutualists, strains of *P. ananatis* are consistently associated with harmful crop and forest infestations. Since 1983, the known hosts of *P. ananatis* have increased to eight plant species in 11 countries, including important crops such as rice, corn, onions, melon, and pineapple. Upon plant infection, these bacteria cause internal rotting, dieback, and blight resulting in severe economic losses. In addition to primary infection in the field, significant post-harvest losses, as observed in onion center rot, have also been reported. Moreover, this plant pathogen can also infect humans and insects, which serve as vectors for plant infection. Thus, there is a compelling need to understand *P. ananatis* pathogenesis to help address their epidemic spread among essential food crops.

Despite the economic and food safety implications of *P. ananatis* infection, the mechanisms of plant pathogenicity have only recently been investigated. Comparative genomic analyses revealed substantial diversity between *P. ananatis* strains, which may account for their ability to colonize and thrive in so many different hosts. The pathogenicity determinants encoded by diverse *P. ananatis* genomes include quorum sensing systems, type VI secretion systems, motility factors, cell-wall degrading enzymes and thiosulfinate resistance alleles. A novel pathogenicity determinant for onion center rot was recently revealed by comparison of the genomic sequences of two pathogenic and two non-pathogenic *P. ananatis* strains (Mol Plant Microbe Interact 2018, 31:1291).

This approach identified a genomic island designated "HiVir", which was subsequently shown to be present in fourteen pathogenic strains and absent in sixteen non-pathogenic strains using a PCR-based screen. The HiVir locus encodes an eleven-gene operon (hereafter designated hvr) that was suggested to encode a biosynthetic pathway for an unknown phosphonic acid natural product based on the presence of a putative pepM gene. This gene encodes the enzyme phosphoenolpyruvate (PEP) phosphonomutase, which catalyzes the first step in all characterized phosphonate biosynthetic pathways, and which has been extensively used as a genetic marker for the ability to produce phosphonic acid metabolites. Deletion of pepM in *P. ananatis* OC5a resulted in a strain with severely attenuated pathogenicity in *Allium cepa* (onion), demonstrating a required role for the hvr operon in onion center rot. Based on this finding, Asselin et al suggested that a small molecule phosphonate is involved in plant disease caused by *P. ananatis*.

Phosphonates, defined by the presence of chemically stable carbon-phosphorus bonds, are an underdeveloped class of bioactive molecules with significant applications in both medicine and agriculture. The bioactivity of these molecules results from their structural similarity to phosphate esters and carboxylic acids, which allows them to bind enzymes that act on analogous substrates, thus inhibiting enzyme activity. A prominent example is the manmade herbicide glyphosate, which was first synthesized by chemists in the 1950's. The phytotoxicity of glyphosate is due to its inhibition of 5-enolpyruvylshikimate-3-phosphate (EPSP) synthase, a key enzyme in the biosynthesis of aromatic amino acids in plants. Significantly, enzyme inhibition by individual phosphonates is quite specific and typically confined to enzymes that act on chemically homologous substrates. Accordingly, a phosphonate can be toxic to one group of organisms, while remaining innocuous to another. Thus, depending on the organism in which the target enzyme is found, phosphonates find applications as specific antibacterial, antifungal, antiparasital and herbicidal compounds. Given the ubiquitous occurrence of phosphate esters and carboxylic acids in metabolism, the range of potential biological targets for phosphonate inhibitors is vast. Indeed, as demonstrated by the number of organisms known to produce bioactive phosphonates, nature has often capitalized on this metabolic Achilles heel. Examples include phosphinothricin tripeptide and fosmidomycin, produced by members of the genus *Streptomyces*, which have potent herbicidal and antimicrobial activity due to their inhibition of the essential enzyme's glutamate synthase and deoxyxylulose-5-phosphate reductoisomerase, respectively. Nature also makes use of the fact that the C—P bond is highly stable and resistant to both chemical and enzymatic degradation. Accordingly, many organisms replace labile biomolecules such as phospholipids and phosphate ester-modified exopolysaccharides with analogous phosphonates.

Considering their useful biological properties, it is not surprising that biosynthesis of phosphonate compounds is common among microbes. Based on the presence of pepM in sequenced genomes and metagenomes, ca. 5% of all bacteria possess the capacity for phosphonate biosynthesis. Biosynthetic gene clusters that include pepM are known to direct the biosynthesis of phosphonolipids, phosphonoglycans, and a wide variety of small molecule secondary metabolites. Like the streptomycete-derived natural products described above, many of these small molecule phosphonates are bioactive. Although considerable progress has been made in understanding the bioactivity and biosynthesis of small molecule phosphonates, only a fraction of the observed pepM-encoding gene clusters have been characterized. Thus, the extent of phosphonate chemical diversity in nature has yet to be established.

Consistent with the idea that phosphonate biosynthesis is common in nature, it has also been observed that about 30% of sequenced bacterial genomes contain genes for phosphonate catabolism, which allows their use as sources of phosphorus, carbon or nitrogen. Genes encoding the carbon-phosphorus (C—P) lyase system, which catalyzes a multi-step phosphonate degradation pathway with broad substrate specificity, are particularly common in bacteria. Other examples include the enzyme phosphonatase, which is specific for aminoethylphosphonate, and a recently characterized oxidative pathway for use of hydroxymethylphosphonate.

One of the challenges for agriculture is the emerging resistance to synthetic herbicides and the lack of novel, effective natural product herbicides. It is estimated that only 7% of conventional pest control agents (includes insecticides, fungicides, and herbicides) are natural products or natural products derived. However, in the case of herbicidal compounds, only one class of natural product-derived herbicide has been registered since 1997, and compared to 30% of fungicides and insecticides, only 8% of herbicidal compounds are natural product-derived. Derivatives of this natural product produced from this strain can be an alternative organic treatment strategy for herbicide-resistant crops.

The problem is the increased resistance to commercially available herbicides poses a threat to the agriculture industry. Accordingly, there is in need for the development of novel herbicides to combat this resistance.

SUMMARY

*Pantoea ananatis* is a significant plant pathogen that targets a number of important crops, a problem that is compounded by the absence of effective treatments to prevent its spread. Our identification of pantaphos as the key virulence factor in onion center rot suggests a variety of approaches that could be employed to address this significant plant disease. Moreover, the general phytotoxicty of the molecule suggests that it could be developed into an effective herbicide to counter the alarming rise in herbicide-resistant weeds.

Accordingly, this disclosure provides a composition comprising a compound of Formula I:

(I)

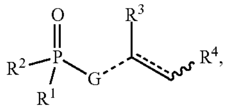

or a salt thereof; wherein

- ----- represents single or double bond;
- ===== represents double or single bond, wherein both ===== and ----- are not double bonds;
- G is $X^ACHOR^5$, O, C(═O), C(═$CH_2$), CHP(═O)$(R^6)_2$, or $CX^B{}_2$;
- $X^A$ is absent or O;
- each $X^B$ is independently H or halo;
- $R^1$ and $R^2$ are each independently $OR^A$ or an amino acid;
- $R^3$ is —C(═O)$R^7$ or a triazole or tetrazole;
- $R^4$ is —C(═O)$R^8$ or a triazole or tetrazole;
- $R^5$ is H, —$(C_1$-$C_6)$alkyl, —$(C_3$-$C_6)$cycloalkyl, aryl, or heteroaryl;
- each $R^6$ is independently $OR^B$ or an amino acid;
- $R^7$ and $R^8$ are each independently $OR^C$ or an amino acid; and
- each $R^A$, $R^B$ and $R^C$ are independently H, —$(C_1$-$C_6)$alkyl, —$(C_3$-$C_6)$cycloalkyl, aryl, or heteroaryl; and a non-aqueous fluid, additive or combination thereof.

This disclosure also provides a method for inhibiting growth or formation of a weed comprising contacting the weed and/or soil where the weed can form and a herbicidally effective amount of a composition or compound disclosed herein, wherein growth or formation of the weed is inhibited.

Also, this disclosure provides a method for inhibiting growth of a cancer cell, treatment of cancer in a subject in need of cancer therapy. Additionally, this disclosure provides a method for forming or manufacturing 2-(hydroxy(phosphono)methyl)maleic acid and 2-phosphonomethylmaleate.

The technology described herein provides novel compounds of Formula I and Formula II, intermediates for the synthesis of compounds of Formula I and Formula II, as well as methods of preparing compounds of Formula I and II. The technology also provides compounds of Formula I and II that are useful as intermediates for the synthesis of other useful compounds. The technology provides for the use of compounds of Formula I and Formula II for the manufacture of medicaments useful for the treatment of cancer in a mammal, such as a human.

The technology provides for the use of the compositions described herein for use in medical therapy or as herbicides. The medical therapy can be treating cancer, for example, brain cancer, breast cancer, lung cancer, pancreatic cancer, prostate cancer, or colon cancer. The invention also provides for the use of a composition as described herein for the manufacture of a medicament to treat a disease in a mammal, for example, cancer in a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
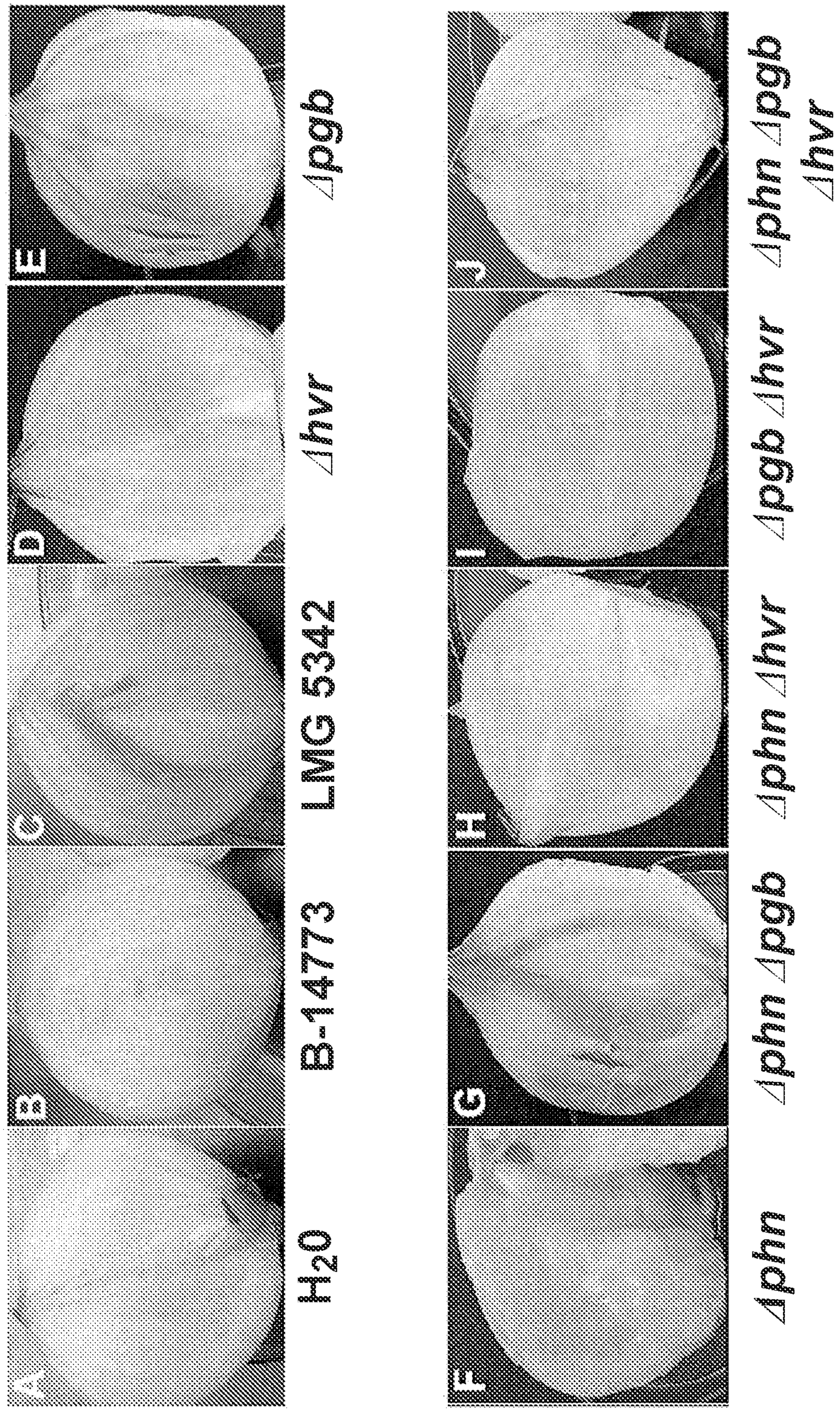
FIG. 1. Onion center rot phenotype of *P. ananatis* strains used in the study. Surface sterilized onion bulbs were inoculated as indicated in each panel, then incubated at 30° C. for fourteen days prior to sectioning to reveal the center rot phenotype. Panels A-C show inoculations of a sterile water control and wild-type strains. Panels D-J show inoculations with mutant derivatives of *P. ananatis* LMG 5342.

*Pantoea ananatis* is the primary cause of onion center rot. Genetic data suggest that a phosphonic acid natural product is required for pathogenesis; however, the nature of the molecule is unknown. Here we show that *P. ananatis* produces at least three phosphonates, two of which were purified and structurally characterized. The first, designated pantaphos, was shown to be 2-(hydroxy(phosphono)methyl) maleate; the second, a probable biosynthetic precursor, was shown to be 2-(phosphonomethyl)maleate. Purified pantaphos is both necessary and sufficient for the hallmark lesions of onion center rot. Moreover, when tested against mustard seedlings, the phytotoxic activity of pantaphos was comparable to the widely used herbicides glyphosate and phosphinothricin. Pantaphos was also active against a variety of human cell lines but was significantly more toxic to glioblastoma cells. Pantaphos showed little activity when tested against a variety of bacteria and fungi.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14' Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent “about,” it will be understood that the particular value without the modifier “about” also forms a further aspect.

The terms “about” and “approximately” are used interchangeably. Both terms can refer to a variation of ±5%, ±10%, ±20%, or ±25% of the value specified. For example, “about 50” percent can in some embodiments carry a variation from 45 to 55 percent, or as otherwise defined by a particular claim. For integer ranges, the term “about” can include one or two integers greater than and/or less than a recited integer at each end of the range. Unless indicated otherwise herein, the terms “about” and “approximately” are intended to include values, e.g., weight percentages, proximate to the recited range that are equivalent in terms of the functionality of the individual ingredient, composition, or embodiment. The terms “about” and “approximately” can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as “up to”, “at least”, “greater than”, “less than”, “more than”, “or more”, and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as “number1” to “number2”, implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than “number10”, it implies a continuous range that includes whole numbers and fractional numbers less than number10, as discussed above. Similarly, if the variable disclosed is a number greater than “number10”, it implies a continuous range that includes whole numbers and fractional numbers greater than number10. These ranges can be modified by the term “about”, whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term “contacting” refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An “effective amount” refers to an amount effective to treat a disease, disorder, and/or condition, or to bring about a recited effect. The disease, disorder, and/or condition is in a living organism such as in an animal, plant, or crop. For example, an effective amount can be an amount effective to reduce the progression or severity of the condition or symptoms being treated. Determination of a therapeutically effective amount is well within the capacity of persons skilled in the art. The term “effective amount” is intended to include an amount of a compound described herein, or an amount of a combination of compounds described herein, e.g., that is effective to treat or prevent a disease or disorder, or to treat the symptoms of the disease or disorder, in a host. Thus, an “effective amount” generally means an amount that provides the desired effect.

Alternatively, the terms “effective amount” or “therapeutically effective amount,” as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an “effective amount” for therapeutic uses is the amount of the composition comprising a compound as disclosed herein required to provide a clinically significant decrease in disease symptoms. An appropriate “effective” amount in any individual case may be determined using techniques, such as a dose escalation study. The dose could be administered in one or more administrations. However, the precise determination of what would be considered an effective dose may be based on factors individual to each patient, including, but not limited to, the patient’s age, size, type or extent of disease, stage of the disease, route of administration of the compositions, the type or extent of supplemental therapy used, ongoing disease process and type of treatment desired (e.g., aggressive vs. conventional treatment).

Compounds disclosed herein may be used as an active ingredient in a medicament to treat an animal or an active ingredient in a herbicidal formulation to treat a plant or crop. The active ingredient in the medicament or the herbicide is administered in an amount that effective for the treatment of a disease, disorder, and/or condition in the animal, plant, or crop.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of a compound of the disclosure into a subject by a method or route that results in at least partial localization of the compound to a desired site. The compound can be administered by any appropriate route that results in delivery to a desired location in the subject.

The compound and compositions described herein may be administered with additional compositions to prolong stability and activity of the compositions, or in combination with other therapeutic drugs or herbicides.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl", defined below. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl(t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below or otherwise described herein. The alkyl can also be optionally partially or fully unsaturated. As such, the recitation of an alkyl group can include an alkenyl group or an alkynyl group. The alkyl can be a monovalent hydrocarbon radical, as described and exemplified above, or it can be a divalent hydrocarbon radical (i.e., an alkylene).

An alkylene is an alkyl group having two free valences at a carbon atom or two different carbon atoms of a carbon chain. Similarly, alkenylene and alkynylene are respectively an alkene and an alkyne having two free valences at two different carbon atoms.

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl can be unsubstituted or substituted. The cycloalkyl group can be monovalent or divalent and can be optionally substituted as described for alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "heterocycloalkyl" or "heterocyclyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 30 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with a substituent described below.

The term "heteroaryl" refers to a monocyclic, bicyclic, or tricyclic ring system containing one, two, or three aromatic rings and containing at least one nitrogen, oxygen, or sulfur atom in an aromatic ring. The heteroaryl can be unsubstituted or substituted, for example, with one or more, and in particular one to three, substituents, as described in the definition of "substituted". Typical heteroaryl groups contain 2-20 carbon atoms in the ring skeleton in addition to the one or more heteroatoms, wherein the ring skeleton comprises a 5-membered ring, a 6-membered ring, two 5-membered rings, two 6-membered rings, or a 5-membered ring fused to a 6-membered ring. Examples of heteroaryl groups include, but are not limited to, 2H-pyrrolyl, 3H-indolyl, 4H-quinolizinyl, acridinyl, benzo[b]thienyl, benzothiazolyl, P-carbolinyl, carbazolyl, chromenyl, cinnolinyl, dibenzo[b, d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments, 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl. Substituents of the indicated groups can be those recited in a specific list of substituents described herein, or as one of skill in the art would recognize, can be one or more substituents selected from alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, and cyano. Suitable substituents of indicated groups can be bonded to a substituted carbon atom include F, Cl, Br, I, OR', $OC(O)N(R')_2$, CN, $CF_3$, $OCF_3$, R', O, S, C(O), S(O), methylenedioxy, ethylenedioxy, $N(R')_2$, SR', SOR', $SO_2R'$, $SO_2N(R')_2$, $SO_3R'$, C(O)R', C(O)C(O)R', $C(O)CH_2C(O)R'$, C(S)R', C(O)OR', OC(O)R', $C(O)N(R')_2$, $OC(O)N(R')_2$, $C(S)N(R')_2$, $(CH_2)_{0-2}NHC(O)R'$, N(R')N(R')C(O)R', N(R')N(R')C(O)OR', $N(R')N(R')CON(R')_2$, $N(R')SO_2R'$, $N(R')SO_2N(R')_2$, N(R')C(O)OR', N(R')C(O)R', N(R')C(S)R', $N(R')C(O)N(R')_2$, $N(R')C(S)N(R')_2$, N(COR')COR', N(OR')R', $C(=NH)N(R')_2$, C(O)N(OR')R', or C(=NOR')R' wherein each R' can independently be hydrogen or a carbon-based moiety (e.g., $(C_1-C_6)$alkyl), and wherein the carbon-based moiety can itself be further substituted. When a substituent is monovalent, such as, for example, F or Cl, it is bonded to the atom it is substituting by a single bond. When a substituent is divalent, such as O, it is bonded to the atom it is substituting by a double bond; for example, a carbon atom substituted with O forms a carbonyl group, C=O.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof, such as racemic mixtures, which form part of the present invention. Many organic compounds exist in optically active forms, i.e., they have the ability to rotate the plane of plane-polarized light. In describing an optically active compound, the prefixes D and L, or R and S. are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate (defined below), which may occur where there has been no stereoselection or stereospecificity in a chemical reaction or process.

The terms "racemic mixture" and "racemate" refer to an equimolar mixture of two enantiomeric species, devoid of optical activity.

The term "$IC_{50}$" is generally defined as the concentration required to kill 50% of the cells in 24 hours.

The term "genome" or "genomic DNA" is referring to the heritable genetic information of a host organism. Said genomic DNA comprises the entire genetic material of a cell or an organism, including the DNA of the bacterial chromosome and plasmids for prokaryotic organisms and includes for eukaryotic organisms the DNA of the nucleus (chromosomal DNA), extrachromosomal DNA, and organellar DNA (e.g., of mitochondria). Preferably, the terms genome or genomic DNA is referring to the chromosomal DNA of the nucleus.

The term "chromosomal DNA" or "chromosomal DNA sequence" in the context of eukaryotic cells is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), in situ PCR and next generation sequencing (NGS).

The term "promoter" refers to a polynucleotide which directs the transcription of a structural gene to produce mRNA. Typically, a promoter is located in the 5' region of a gene, proximal to the start codon of a structural gene. If a promoter is an inducible promoter, then the rate of transcription increases in response to an inducing agent. In contrast, the rate of transcription is not regulated by an inducing agent if the promoter is a constitutive promoter. The term "enhancer" refers to a polynucleotide. An enhancer can increase the efficiency with which a particular gene is transcribed into mRNA irrespective of the distance or orientation of the enhancer relative to the start site of transcription. Usually, an enhancer is located close to a promoter, a 5'-untranslated sequence or in an intron.

A polynucleotide is "heterologous to" an organism or a second polynucleotide if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e. g. a genetically engineered coding sequence or an allele from a different ecotype or variety).

"Transgene", "transgenic" or "recombinant" refers to a polynucleotide manipulated by man or a copy or complement of a polynucleotide manipulated by man. For instance, a transgenic expression cassette comprising a promoter operably linked to a second polynucleotide may include a promoter that is heterologous to the second polynucleotide as the result of manipulation by man (e.g., by methods described in Sambrook et al., Molecular Cloning-A Laboratory Manual, Cold Spring Harbor Laboratory, Cold Spring Harbor, New York, (1989) or Current Protocols in Molecular Biology Volumes 1-3, John Wiley & Sons, Inc. (1994-1998)) of an isolated nucleic acid comprising the expression cassette. In another example, a recombinant expression cassette may comprise polynucleotides combined in such a way that the polynucleotides are extremely unlikely to be found in nature. For instance, restriction sites or plasmid vector sequences manipulated by man may flank or separate the promoter from the second polynucleotide. One of skill will recognize that polynucleotides can be manipulated in many ways and are not limited to the examples above.

In case the term "recombinant" is used to specify an organism or cell, e.g., a microorganism, it is used to express that the organism or cell comprises at least one "transgene", "transgenic" or "recombinant" polynucleotide, which is usually specified later on.

A polynucleotide "exogenous to" an individual organism is a polynucleotide which is introduced into the organism by any means other than by a sexual cross.

The terms "operable linkage" or "operably linked" are generally understood as meaning an arrangement in which a genetic control sequence, e.g., a promoter, enhancer or terminator, is capable of exerting its function with regard to a polynucleotide being operably linked to it, for example a polynucleotide encoding a polypeptide. Function, in this context, may mean for example control of the expression, i.e., transcription and/or translation, of the nucleic acid sequence. Control, in this context, encompasses for example initiating, increasing, governing, or suppressing the expression, i.e., transcription and, if appropriate, translation. Controlling, in turn, may be, for example, tissue- and/or time-specific. It may also be inducible, for example by certain chemicals, stress, pathogens, and the like. Preferably, operable linkage is understood as meaning for example the sequential arrangement of a promoter, of the nucleic acid sequence to be expressed and, if appropriate, further regulatory elements such as, for example, a terminator, in such a way that each of the regulatory elements can fulfill its function when the nucleic acid sequence is expressed. An operably linkage does not necessarily require a direct linkage in the chemical sense. For example, genetic control sequences like enhancer sequences are also capable of exerting their function on the target sequence from positions located at a distance to the polynucleotide, which is operably linked. Preferred arrangements are those in which the nucleic acid sequence to be expressed is positioned after a sequence acting as promoter so that the two sequences are linked covalently to one another. The distance between the promoter and the amino acid sequence encoding polynucleotide in an expression cassette, is preferably less than 200 base pairs, especially preferably less than 100 base pairs, very especially preferably less than 50 base pairs. The skilled worker is familiar with a variety of ways in order to obtain such an expression cassette. However, an expression cassette may also be constructed in such a way that the nucleic acid sequence to be expressed is brought under the control of an endogenous genetic control element, for example an endogenous promoter, for example by means of homologous recombination or else by random insertion. Such constructs are likewise understood as being expression cassettes for the purposes of the invention.

The term "expression cassette" or "expression vector" means those constructs in which the nucleic acid sequence encoding an amino acid sequence to be expressed is linked operably to at least one genetic control element which enables or regulates its expression (i.e., transcription and/or translation). The expression may be, for example, stable or transient, constitutive, or inducible. Examples of expression vectors are well known in the art and are described, for example, in U.S. Pat. No. 7,416,874.

The terms "express," "expressing," "expressed" and "expression" refer to expression of a gene product (e.g., a biosynthetic enzyme of a gene of a pathway or reaction defined and described in this application) at a level that the resulting enzyme activity of this protein encoded for or the pathway or reaction that it refers to allows metabolic flux through this pathway or reaction in the organism in which this gene/pathway is expressed in. The expression can be done by genetic alteration of the microorganism that is used as a starting organism. In some embodiments, a microorganism can be genetically altered (e.g., genetically engineered) to express a gene product at an increased level relative to that produced by the starting microorganism or in a comparable microorganism which has not been altered. Genetic alteration includes, but is not limited to, altering or modifying regulatory sequences or sites associated with expression of a particular gene (e.g. by adding strong promoters, inducible promoters or multiple promoters or by removing regulatory sequences such that expression is constitutive), modifying the chromosomal location of a particular gene, altering nucleic acid sequences adjacent to a particular gene such as a ribosome binding site or transcription terminator, increasing the copy number of a particular gene, modifying proteins (e.g., regulatory proteins, suppressors, enhancers, transcriptional activators and the like) involved in transcription of a particular gene and/or translation of a particular gene product, or any other conventional means of deregulating expression of a particular gene using routine in the art (including but not limited to use of antisense nucleic acid molecules, for example, to block expression of repressor proteins).

In some embodiments, a microorganism can be physically or environmentally altered to express a gene product at an increased or lower level relative to level of expression of the gene product unaltered microorganism. For example, a microorganism can be treated with, or cultured in the presence of an agent known, or suspected to increase transcription of a particular gene and/or translation of a particular gene product such that transcription and/or translation are enhanced or increased. Alternatively, a microorganism can be cultured at a temperature selected to increase transcription of a particular gene and/or translation of a particular gene product such that transcription and/or translation are enhanced or increased.

The term "vector", preferably, encompasses phage, plasmid, fosmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, preferably, further comprises selectable markers for propagation and/or selection in a recombinant microorganism. The vector may be incorporated into a recombinant microorganism by various techniques well known in the art. If introduced into a recombinant microorganism, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques.

The terms "transformation" and "transfection", conjugation and transduction, as used in the present context, are intended to comprise a multiplicity of prior-art processes for introducing foreign nucleic acid (for example DNA) into a recombinant microorganism, including calcium phosphate, rubidium chloride or calcium chloride co-precipitation, DEAE-dextran-mediated transfection, lipofection, natural competence, carbon-based clusters, chemically mediated transfer, electroporation or particle bombardment. Methods for many species of microorganisms are readily available in the literature.

Nucleic acid sequences cited herein are written in a 5' to 3' direction unless indicated otherwise. The term "nucleic acid" refers to either DNA or RNA or a modified form thereof comprising the purine or pyrimidine bases present in DNA (adenine "A", cytosine "C", guanine "G", thymine "T") or in RNA (adenine "A", cytosine "C", guanine "G", uracil "U"). Interfering RNAs provided herein may comprise "T" bases, for example at 3' ends, even though "T" bases do not naturally occur in RNA. In some cases, these bases may appear as "dT" to differentiate deoxyribonucleotides present in a chain of ribonucleotides.

The term "sequence identity" between two nucleic acid sequences is understood as meaning the percent identity of the nucleic acid sequence over in each case the entire sequence length which is calculated by alignment with the aid of the program algorithm GAP (Wisconsin Package Version 10.0, University of Wisconsin, Genetics Computer Group (GCG), Madison, USA), setting, for example, the following parameters:

Gap Weight: 12 Length Weight: 4; Average Match: 2,912 Average Mismatch:-2,003.

The term "sequence identity" between two amino acid sequences is understood as meaning the percent identity of the amino acids sequence over in each case the entire sequence length which is calculated by alignment with the aid of the program algorithm GAP (Wisconsin Package Version 10.0, University of Wisconsin, Genetics Computer Group (GCG), Madison, USA), setting, for example, the following parameters: Gap Weight: 8; Length Weight: 2; Average Match: 2,912; Average Mismatch:-2,003.

The term "hybridization" as defined herein is a process wherein substantially homologous complementary nucleotide sequences anneal to each other. The hybridization process can occur entirely in solution, i.e., both complementary nucleic acids are in solution. The hybridization process can also occur with one of the complementary nucleic acids immobilized to a matrix such as magnetic beads, Sepharose beads or any other resin. The hybridization process can furthermore occur with one of the complementary nucleic acids immobilized to a solid support such as a nitro-cellulose or nylon membrane or immobilized by e.g., photolithography to, for example, a siliceous glass support (the latter known as nucleic acid arrays or microarrays or as nucleic acid chips). In order to allow hybridization to occur, the nucleic acid molecules are generally thermally or chemically denatured to melt a double strand into two single strands and/or to remove hairpins or other secondary structures from single stranded nucleic acids.

The term "stringency" refers to the conditions under which a hybridization takes place. The stringency of hybridization is influenced by conditions such as temperature, salt concentration, ionic strength, and hybridization buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridization conditions are typically used for isolating hybridizing sequences that have high sequence similarity to the target nucleic acid sequence. However, nucleic acids may deviate in sequence and still encode a substantially identical polypeptide, due to the degeneracy of the genetic code. Therefore, medium stringency hybridization conditions may sometimes be needed to identify such nucleic acid molecules.

The $T_m$ is the temperature under defined ionic strength and pH, at which 50% of the target sequence hybridizes to a perfectly matched probe. The $T_m$ is dependent upon the solution conditions and the base composition and length of the probe. For example, longer sequences hybridize specifically at higher temperatures. The maximum rate of hybridization is obtained from about 16° C. up to 32° C. below $T_m$. The presence of monovalent cations in the hybridization solution reduces the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridization to be performed at 30 to 45° C., though the rate of hybridization will be lowered. Base pair mismatches reduce the hybridization rate and the thermal stability of the duplexes. On average and for large probes, the $T_m$ decreases about 1° C. per % base mismatch. The $T_m$ may be calculated using the following equations, depending on the types of hybrids:

1) DNA-DNA hybrids (Meinkoth and Wahl, Anal. Biochem., 138: 267-284, 1984):

$$T_m=81.5°\text{ C.}+16.6\times \text{logio}[Na^+]^a+0.41\times\%[G/C^b]-500\times[L^c]^{-1}-0.61\times\%\text{ formamide}$$

2) DNA-RNA or RNA-RNA Hybrids:

$$T_m=79.8°\text{ C.}+18.5(\text{logio}[Na^+]^a)+0.58(\%\ G/C^b)+11.8(\%\ G/C^b)^2-820/L^c$$

3) oligo-DNA or oligo-RNA$^d$ Hybrids:

For <20 nucleotides: $T_m=2(l_n)$

For 20-35 nucleotides: $T_m=22+1\ 0.46(l_n)$ a or for other monovalent cation, but only accurate in the 0.01-0.4 M range.
b only accurate for % GC in the 30% to 75% range.
c L=length of duplex in base pairs.
d oligo, oligonucleotide; $l_n$, =effective length of primer=2×(no. of G/C)+(no. of A/T).

Non-specific binding may be controlled using any one of a number of known techniques such as, for example, blocking the membrane with protein containing solutions, additions of heterologous RNA, DNA, and SDS to the hybridization buffer, and treatment with RNAse. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridization, and which will either maintain or change the stringency conditions.

Besides the hybridization conditions, specificity of hybridization typically also depends on the function of post-hybridization washes. To remove background resulting from non-specific hybridization, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridization stringency. A positive hybridization gives a signal that is at least twice of that of the background. Generally, suitable stringent conditions for nucleic acid hybridization assays or gene amplification detection procedures are as set forth above. More or less stringent conditions may also be selected. The skilled artisan is aware of various parameters which may be altered during washing, and which will either maintain or change the stringency conditions.

For example, typical high stringency hybridization conditions for DNA hybrids longer than 50 nucleotides encompass hybridization at 65° C. in 1×SSC or at 42° C. in 1×SSC and 50% formamide, followed by washing at 65° C. in 0.3×SSC. Examples of medium stringency hybridization conditions for DNA hybrids longer than 50 nucleotides encompass hybridization at 50° C. in 4×SSC or at 40° C. in 6×SSC and 50% formamide, followed by washing at 50° C. in 2×SSC. The length of the hybrid is the anticipated length for the hybridizing nucleic acid. When nucleic acids of known sequence are hybridized, the hybrid length may be determined by aligning the sequences and identifying the conserved regions described herein. 1×SSC is 0.15M NaCl and 15 mM sodium citrate; the hybridization solution and wash solutions may additionally include 5×Denhardt's reagent, 0.5-1.0% SDS, 100 μg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

Embodiments of the Technology

This disclosure provides a composition comprising a compound of Formula I:

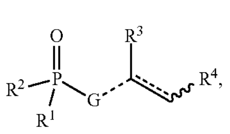

(I)

or a salt thereof; wherein

----- represents single or double bond;

----- represents double or single bond, wherein both ----- and ----- are not double bonds;

G is $X^A CHOR^5$, O, C(═O), C(═$CH_2$), CHP(═O)$(R^6)_2$, or $CX^B_2$;

$X^A$ is absent or O;

each $X^B$ is independently H or halo;

$R^1$ and $R^2$ are each independently $OR^A$ or an amino acid;

$R^3$ is —C(═O)$R^7$ or a triazole or tetrazole;

$R^4$ is —C(═O)$R^8$ or a triazole or tetrazole;

$R^5$ is H, —$(C_1$-$C_6)$alkyl, —$(C_3$-$C_6)$cycloalkyl, aryl, or heteroaryl;

each $R^6$ is independently $OR^B$ or an amino acid;

$R^7$ and $R^8$ are each independently $OR^C$ or an amino acid; and each $R^A$, $R^B$ and $R^C$ are independently H, —($C_1$-$C_6$)alkyl, —($C_3$-$C_6$)cycloalkyl, aryl, or heteroaryl; and a fluid (aqueous or non-aqueous), additive (non-naturally occurring) or combination thereof.

In various embodiments, $R^1$, $R^2$, $R^6$, $R^7$ and $R^8$ are each independently $NR^XR^Y$, wherein each $R^X$ and $R^Y$ are independently H, —($C_1$-$C_6$)alkyl, —($C_3$-$C_6$)cycloalkyl, aryl, or heteroaryl. In various additional embodiments, $R^3$ and $R^4$ are each independently $NO_2$, $CO_2R^X$, P(═O)($OR^X$)$_2$, S(═O)$_2OR^X$, or S(═O)$R^X$, wherein each $R^X$ is independently H, —($C_1$-$C_6$)alkyl, or —($C_1$-$C_6$)cycloalkyl. In various other embodiments, the compound is a prodrug. In various embodiments, the compound is suitably substituted with a substituent (e.g., to form an ester) that is metabolized or cleaved to release the active form of the compound (e.g., pantaphos).

In some embodiments, the fluid is water or an aqueous solution, a non-aqueous fluid or solution, an oil, an organic solvent, a liquid, or combination thereof. In other embodiments, the composition is formulated as a powder, fine powder, granule, or pellet. The formulation can comprise additives, salts, an emulsifier, nanoparticles, surfactants, buffering agents, wetting agents, colloids, lipids, phospholipids, biodegradable polymers, a second active agent, one or more active agents, or a combination thereof. In other embodiments, the compound in the composition can be encapsulated in a micro- or nanocapsule, or a time release capsule.

In various embodiments, G is $CHOR^5$. In various embodiments, the compound is the (S)-enantiomer. In various embodiments, the compound is the (R)-enantiomer. In various embodiments, $R^1$ and $R^2$ are $OR^A$. In various embodiments, $R^3$ and $R^4$ are —$CO_2R^C$. In s various embodiments, $R^3$ and $R^4$ have a cis-configuration when ⋯⋯ is double bond.

In various embodiments, a compound of Formula I is represented by Formula II:

(II)

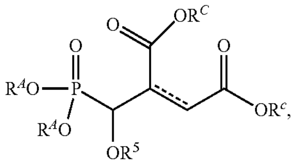

or a salt thereof.

In various embodiments, the compound is pantaphos:

(pantaphos)

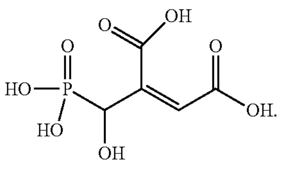

In various embodiments, the compound is compound 2:

(2)

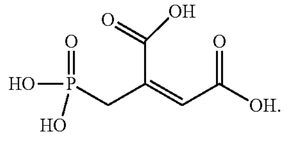

In some embodiments, the composition comprises pantaphos and compound 2.

This disclosure also provides a compound of Formula I:

(I)

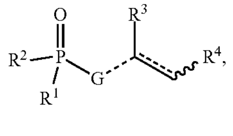

or a salt thereof; wherein

----- represents single or double bond;

⋯⋯ represents double or single bond, wherein both ⋯⋯ and ----- are not double bonds;

G is $X^ACHOR^5$, O, C(═O), C(═$CH_2$), CHP(═O)($R^6$)$_2$, or $CX^B{}_2$;

$X^A$ is absent or O;

each $X^B$ is independently H or halo;

$R^1$ and $R^2$ are each independently $OR^A$ or an amino acid;

$R^3$ is —C(═O)$R^7$ or a triazole or tetrazole;

$R^4$ is —C(═O)$R^8$ or a triazole or tetrazole;

$R^5$ is H, —($C_1$-$C_6$)alkyl, —($C_3$-$C_6$)cycloalkyl, aryl, or heteroaryl;

each $R^6$ is independently $OR^B$ or an amino acid;

$R^7$ and $R^8$ are each independently $OR^C$ or an amino acid; and each $R^A$, $R^B$ and $R^C$ are independently H, —($C_1$-$C_6$)alkyl, —($C_3$-$C_6$)cycloalkyl, aryl, or heteroaryl.

In some embodiments, the compound is not a natural product. In some embodiments, the compound is not 2-(hydroxy(phosphono)methyl)maleic acid or 2-(phosphonomethyl)maleic acid. In various embodiments, G is CHOH. In various embodiments, $R^1$ and $R^2$ are OH. In various embodiments, $R^3$ and $R^4$ are —$CO_2H$.

In some other embodiments the compound is represented by any one of the following structures:

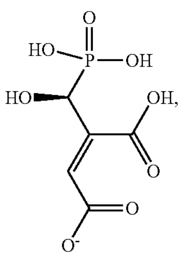

Pantaphos

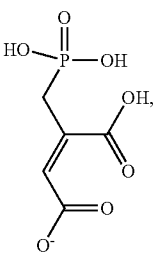

Compound 2

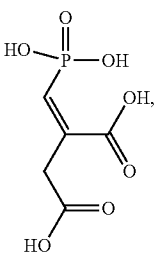

ΔShift

-continued

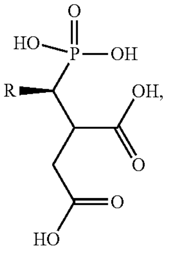

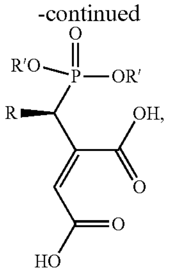

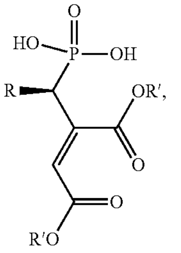

ΔReduction
R = OH or H

R = (OH or H)
R' = alkyl

Ester
R = OH or H

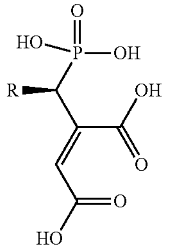

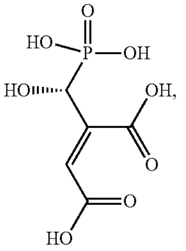

Alcohol manipulation

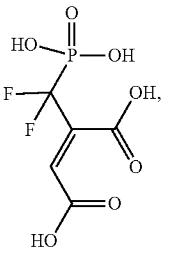

Difluoromethylene phosponate

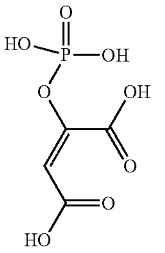

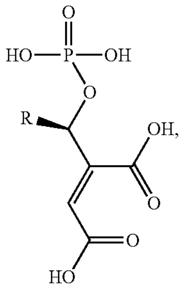

Phosphate
R = (OH or H)

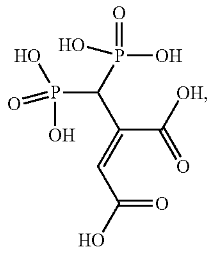

Di-Phosphonate

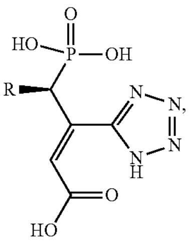

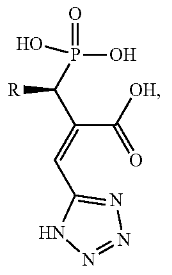

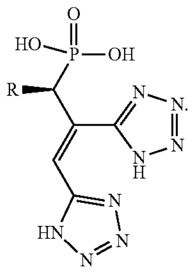

tetrazoles
R = (OH or H)

In some embodiments the compound is represented by:

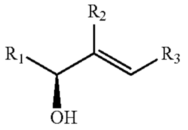

or the enantiomer thereof, wherein $R_1$, $R_2$, and $R_3$ are each independently carboxylate, phosphonate, nitrate, sulfonate, sulfoxide, or a combination thereof;

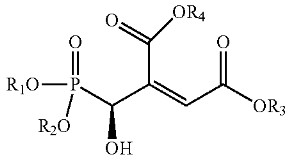

or

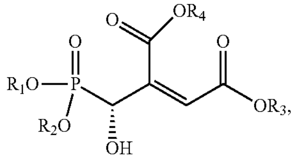

wherein $R^1$, $R^2$, $R^3$, and R are each independently H, alkyl, an aromatic group, or a combination thereof;

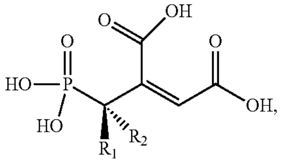

wherein $R^1$ and $R^2$ are each independently H, F, Cl, Br, I, or a combination thereof;

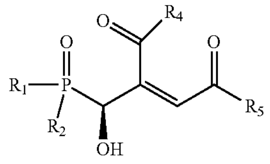

or the enantiomer thereof, wherein $R^1$, $R^2$, $R^4$, and $R^5$ are each independently any amino acid, wherein the amino acid forms an amide or phosphonamide linkage.

In some embodiments, an aqueous composition comprises any one or more of the structures disclosed herein. In some embodiments the composition comprises adjuvants and surfactants known to one of ordinary skill in the art for herbicidal formulations. In various embodiments, the compound is the (R)- or (S)-enantiomer. In various embodiments, the compound is levorotatory or dextrorotatory. In various embodiments, the compound is a salt.

Also, this disclosure provides a method for inhibiting growth or formation of a weed comprising contacting the weed and/or soil where the weed can form and a herbicidally effective amount of a composition or compound disclosed herein, wherein growth or formation of the weed is inhibited. In some embodiments, the weed is killed. In some embodiments, the weed is killed, or blocked or suppressed from germinating without significantly harming other plants, vegetation or crops.

In some embodiments, the weed is controlled, where control is the destruction of unwanted weeds, or the damage of them to the point where they are no longer competitive with a crop, other plants or vegetation. In some other embodiments, the weed is suppressed, where suppression is incomplete control but provides an economic benefit, such as reduced competition with a crop, other plants or vegetation.

In some embodiments, the composition or compound contacts vegetation and/or soil where the vegetation can form, and growth or formation of the weed is selectively inhibited.

Additionally, this disclosure provides a method for inhibiting growth of a cancer cell comprising contacting the cancer cell and an effective amount of a composition or compound disclosed herein, wherein growth of the cancer is inhibited. In some embodiments, the cancer cell is a glioblastoma cell.

Furthermore, this disclosure provides a method for treating cancer in a subject in need thereof comprising administering a therapeutically effective amount of the compound or composition disclosed herein, wherein the cancer is treated.

In various embodiments, an effective amount of a compound disclosed herein, such as pantaphos, is about 0.01 $mg/m^2$ or less to about 100 $g/m^2$ or more in for an animal or crop. In other embodiments, the effective amount is about 0.1 $mg/m^2$ to about 10 $g/m^2$. In other embodiments, the effective amount is about 0.05 $mg/m^2$, 0.1 $mg/m^2$, 0.2 $mg/m^2$, about 0.5 $mg/m^2$, 1 $mg/m^2$, about 2 $mg/m^2$, about 5 $mg/m^2$, 10 $mg/m^2$, about 15 $mg/m^2$, 20 $mg/m^2$, about 50 $mg/m^2$, about 100 $mg/m^2$, 200 $mg/m^2$, about 300 $mg/m^2$, 500 $mg/m^2$, about 750 $mg/m^2$, about 1000 $mg/m^2$, 1500 $mg/m^2$, about 2000 $mg/m^2$, 3000 $mg/m^2$, about 5000 $mg/m^2$, about 7500 $mg/m^2$, 10,000 $mg/m^2$, about 20,000 $mg/m^2$, 50,000 $mg/m^2$, about 75,000 $mg/m^2$, about 100,000 $mg/m^2$, or any amount between the cited amounts.

In various embodiments, a compound disclosed herein in an herbicidal composition or pharmaceutical composition is synergistic with a second active agent to control weeds or treat a cancer.

Furthermore, this disclosure provides a method for forming 2-(hydroxy(phosphono)methyl)maleic acid:

(pantaphos)

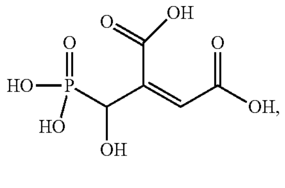

or salt thereof, comprising:

a) isomerizing phosphoenolpyruvate (PEP; 2-(phosphonooxy)acrylic acid) to 3-phosphonopyruvate (PnPy; 2-oxo-3-phosphonopropanoic acid);

b) condensing an acetyl group and PnPy to form phosphonomethylmalate (PMM; 2-hydroxy-2-(phosphonomethyl)succinic acid);

c) dehydrating PMM to 2-phosphonomethylmaleate (2-(phosphonomethyl)maleic acid); and d) oxidizing 2-phosphonomethylmaleate to pantaphos (2-(hydroxy(phosphono)methyl) maleic acid);

wherein each step a)-d) is completed in in-vitro, a vessel, or reactor, wherein the vessel or reactor is man-made.

In some embodiments, isomerizing is catalyzed by PEP mutase (HvrA); condensing is catalyzed by phosphonomethylmalate synthase (HvrC) and the acetyl group is acetyl-CoA; dehydrating is catalyzed by large isopropylmalate dehydratase (HvrD) and/or small isopropylmalate dehydratase (HvrE) dehydratase; and oxidizing is catalyzed by flavin-dependent monooxygenase (HvrB) and optionally flavin reductase (HvrK).

In some embodiments, the compound pantaphos can be prepared from a sequential biosynthetic process using purified enzymes HvrA, HvrC, HvrDE and HvrBK (see Scheme 1), in the order shown, beginning by contacting phosphoenolpyruvate (PEP) and HvrA, wherein the reaction products are contacted by the next enzyme in the sequence.

In another embodiment, the compound pantaphos can be prepared from a sequential biosynthetic process using purified enzymes HvrA (SEQ ID NO: 14), HvrC (SEQ ID NO: 16), HvrD (SEQ ID NO: 17), HvrE (SEQ ID NO: 18), HvrB (SEQ ID NO: 15), and HvrK (SEQ ID NO: 24) (see Scheme 1), in the order shown, beginning by contacting phosphoenolpyruvate (PEP) and HvrA (SEQ ID NO: 14), wherein the reaction products are contacted by the next enzyme in the sequence.

Additionally, this disclosure provides a nucleic acid molecule comprising an hvr operon (hvrA-hvrL) of *Pantoea* Sp. In other embodiments, a nucleic acid molecule comprises one or more genes selected from the group consisting of hvrA, hvrB, hvrC, hvrD, hvrE, and hvrK of *Pantoea* Sp. In another embodiment, a nucleic acid molecule comprises the genes hvrA, hvrB, hvrC, hvrD, hvrE, and hvrK of *Pantoea* Sp.

In other embodiments, a nucleic acid molecule comprises the genes hvrA (SEQ ID NO: 1), hvrB (SEQ ID NO: 2), hvrC (SEQ ID NO: 3), hvrD (SEQ ID NO: 4), hvrE (SEQ ID NO: 5), hvrF (SEQ ID NO: 6), hvrG (SEQ ID NO: 7), hvrH (SEQ ID NO: 8), hvrI (SEQ ID NO: 9), hvrJ (SEQ ID NO: 10), hvrK (SEQ ID NO: 11), and hvrL (SEQ ID NO: 12) of *Pantoea ananatis*.

In some embodiments, a nucleic acid molecule comprises one or more genes selected from the group consisting of hvrA (SEQ ID NO: 1), hvrB (SEQ ID NO: 2), hvrC (SEQ ID NO: 3), hvrD (SEQ ID NO: 4), hvrE (SEQ ID NO: 5), hvrF (SEQ ID NO: 6), hvrG (SEQ ID NO: 7), hvrH (SEQ ID NO: 8), hvrI (SEQ ID NO: 9), hvrJ (SEQ ID NO: 10), hvrK (SEQ ID NO: 11), and hvrL (SEQ ID NO: 12) of *Pantoea ananatis*.

In other embodiments, a nucleic acid molecule comprises the genes hvrA (SEQ ID NO: 1), hvrB (SEQ ID NO: 2), hvrD (SEQ ID NO: 4), hvrE (SEQ ID NO: 5), and hvrK (SEQ ID NO: 11) of *Pantoea ananatis*. In still other embodiments, a nucleic acid molecule comprises the genes hvrA (SEQ ID NO: 1), hvrB (SEQ ID NO: 2), hvrC (SEQ ID NO: 3), hvrD (SEQ ID NO: 4), hvrE (SEQ ID NO: 5), and hvrK (SEQ ID NO: 11) of *Pantoea ananatis*.

In other embodiments, a nucleic acid molecule comprises one or more genes selected from the group consisting of hvrA (SEQ ID NO: 1), hvrB (SEQ ID NO: 2), hvrC (SEQ ID NO: 3), hvrD (SEQ ID NO: 4), hvrE (SEQ ID NO: 5), and hvrK (SEQ ID NO: 11) of *Pantoea ananatis*.

In other embodiments, the disclosure provides a nucleic acid molecule comprising an hvr operon (hvrA-hvrL) of *Pantoea* Sp. operably linked to an inducible promotor sequence, wherein induction of the promoter and expression of the genes of the hvr operon causes the production of a phosphonate compound of Formula I or Formula II. In various embodiments the phosphonate compound is 2-(hydroxy(phosphono)methyl) maleic acid (pantaphos).

Suitable inducible promoters for use with various embodiments include, but are not limited to, T7, T7lac, rpoS, PrhaBAD, mmsA, trc, tetA, tac, lac, tacM, $P_L$, araBAD, cspA, cspB, phyL, NBP3510, P43, Pspac, $P_{170}$, Pgrac, and trp. In some embodiments, the inducible promoter is a lac or a tac promoter. In some embodiments, the inducible promoter is a tac promoter having the nucleic acid sequence according to SEQ ID NO: 13.

In other embodiments, a nucleic acid molecule comprises an inducible promoter and one or more genes selected from the group consisting of hvrA, hvrB, hvrC, hvrD, hvrE, and hvrK of *Pantoea* Sp, wherein the one or more genes are operably linked to the inducible promoter.

In some embodiments, a nucleic acid molecule comprises an inducible promoter and the genes hvrA (SEQ ID NO: 1), hvrB (SEQ ID NO: 2), hvrC (SEQ ID NO: 3), hvrD (SEQ ID NO: 4), hvrE (SEQ ID NO: 5), hvrF (SEQ ID NO: 6), hvrG (SEQ ID NO: 7), hvrH (SEQ ID NO: 8), hvrI (SEQ ID NO: 9), hvrJ (SEQ ID NO: 10), hvrK (SEQ ID NO: 11), and hvrL (SEQ ID NO: 12) of *Pantoea ananatis*, wherein the genes are operably linked to the inducible promoter.

In some embodiments, a nucleic acid molecule comprises an inducible promoter and one or more genes selected from the group consisting of hvrA (SEQ ID NO: 1), hvrB (SEQ ID NO: 2), hvrC (SEQ ID NO: 3), hvrD (SEQ ID NO: 4), hvrE (SEQ ID NO: 5), hvrF (SEQ ID NO: 6), hvrG (SEQ ID NO: 7), hvrH (SEQ ID NO: 8), hvrI (SEQ ID NO: 9), hvrJ (SEQ ID NO: 10), hvrK (SEQ ID NO: 11), and hvrL (SEQ ID NO: 12) of *Pantoea ananatis*, wherein the one or more genes are operably linked to the inducible promoter.

In other embodiments, a nucleic acid molecule comprises an inducible promoter and the genes hvrA (SEQ ID NO: 1), hvrB (SEQ ID NO: 2) hvrD (SEQ ID NO: 4), hvrE (SEQ ID NO: 5), and hvrK (SEQ ID NO: 11) of *Pantoea ananatis*, wherein the genes are operably linked to the inducible promoter. In another embodiment, a nucleic acid molecule comprises an inducible promoter and the genes hvrA (SEQ ID NO: 1), hvrB (SEQ ID NO: 2), hvrC (SEQ ID NO: 3), hvrD (SEQ ID NO: 4), hvrE (SEQ ID NO: 5), and hvrK (SEQ ID NO: 11) of *Pantoea ananatis*, wherein the genes are operably linked to the inducible promoter.

In other embodiments, a nucleic acid molecule comprises an inducible promoter and one or more genes selected from the group consisting of hvrA (SEQ ID NO: 1), hvrB (SEQ ID NO: 2), hvrD (SEQ ID NO: 4), hvrE (SEQ ID NO: 5), and hvrK (SEQ ID NO: 11) of *Pantoea ananatis* or one or more genes selected from the group consisting of hvrA (SEQ ID NO: 1), hvrB (SEQ ID NO: 2),), hvrC (SEQ ID NO: 3), hvrD (SEQ ID NO: 4), hvrE (SEQ ID NO: 5), and hvrK (SEQ ID NO: 11) of *Pantoea ananatis*.

In another embodiment, a nucleic acid molecule comprises an inducible promoter according to the nucleic acid sequence of SEQ ID NO: 13 and a nucleic acid sequence according to SEQ ID NO: 1, 2, 3, 4, 5, and 11 encoding the genes hvrA, hvrB, hvrC, hvrD, hvrE, and hvrK, respectively, wherein the genes are operably linked to the inducible promoter.

In some embodiments, a nucleic acid molecule comprises a nucleic acid sequence having at least 60%, preferably at least 65, 70, 75, 80, 85, 90, 95, 96, 97, 98 or 99%, identity to SEQ ID NO: 1, 2, 3, 4, 5, 6, 7, 8, 9, 10, 11, and 12.

Also, this disclosure provides a recombinant cell for producing a phosphonate compound according to Formula I or Formula II comprising a nucleic acid molecule (e.g., expression vector) disclosed herein. In some embodiments, a recombinant cell expresses one or more proteins selected from the group consisting of SEQ ID NO: 14, 15, 16, 17, 18, 19, 20, 21, 22, 23, 24, and 25. In some embodiments, a recombinant cell expresses one or more proteins having an amino acid sequence having at least 60%, preferably at least 65, 70, 75, 80, 85, 90, 95, 96, 97, 98 or 99%, identity to one or more proteins selected from the group consisting of SEQ ID NO: 14, 15, 16, 17, 18, 19, 20, 21, 22, 23, 24, and 25.

In various embodiments, the nucleic acid molecule is inserted into a cell and maintained as a plasmid or integrated into a chromosome of the cell. In various embodiments, the cell is selected from a genus from the group consisting of *Pantoea, Clostridium, Zymomonas, Escherichia, Salmonella, Serratia, Erwinia, Klebsiella, Shigella, Rhodococcus, Pseudomonas, Bacillus, Lactobacillus, Lactococcus, Enterococcus, Alcaligenes, Paenibacillus, Arthrobacter, Corynebacterium, Brevibacterium, Schizosaccharomyces, Kluveromyces, Yarrowia, Pichia, Zygosaccharomyces, Debaryomyces, Candida, Brettanomyces, Pachysolen, Hansenula, Issatchenkia, Trichosporon, Yamadazyma*, and *Saccharomyces.*

In various embodiments, the cell is of the genus *Pantoea, Escherichia*, or *Saccharomyces*. Examples of species belonging to the *Pantoea* genus include, but are not limited to *Pantoea agglomerans, Pantoea ananatis, Pantoea stewartii, Pantoea citrea, Pantoea dispersa, Pantoea punctate, Pantoea terrea, Pantoea deleyi, Pantoea anthophila, Pantoea allii*, and *Pantoea eucalypti*. In various embodiments, the cell is *Pantoea ananatis, Escherichia coli*, or *Saccharomyces cerevisiae.*

Methods of making recombinant cells and nucleic acid molecules are known in the art and are described herein and, for example, in International Pat. Pub. No. WO/2020/090940 and WO2014129898; and U.S. Pat. Pub. No. US20190256838 and US20140134689.

This disclosure also provides a process for producing a phosphonate compound according to Formula I or Formula II comprising the steps of:

a) providing a cell culture of a recombinant cell disclosed herein (see above), wherein the recombinant cell produces the phosphonate, and the cell culture is about 1 L to about 10 L in volume;
b) mixing an inducer molecule with the recombinant cell culture;
c) incubating the induced recombinant cell culture for up to 96 hours with constant oxygenation;
d) pelleting cells of the recombinant cell culture and collecting a supernatant; e) concentrating the supernatant;
f) extracting the phosphonate from the concentrated supernatant using methanol extraction to form an extracted supernatant; and g) purifying the phosphonate from a methanol soluble fraction of the extracted supernatant.

In various embodiments, the phosphonate is 2-(hydroxy (phosphono)methyl)maleic acid. In some embodiments, step g comprises iron-IMAC purification followed by flash chromatography and HILIC HPLC. In some embodiments, the cell culture comprises a recombinant *Pantoea ananatis, Escherichia coli*, or *Saccharomyces cerevisiae* cell. In some embodiments, the cell culture is a recombinant *Pantoea ananatis*. In some embodiments, the constant oxygenation has a flow rate of 5 L/min, and the cell culture is maintained at a temperature of 30° C.

Another embodiment of the present disclosure provides a compound comprising a hydroxylated allyl phosphonic acid of Formula A, wherein $R_1$ and $R_2$ are independently selected from the group comprising carboxylic acids and derivatives (ketones, esters, carboxylic acids); hydroxyl groups; amines; ethers; halogens; alkyl or aryl groups; or alkyl or aryl groups containing the abovementioned functional groups.

Formula A

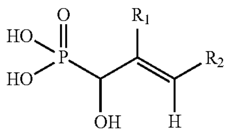

Another embodiment of the present disclosure provides a compound comprising a hydroxylated allyl phosphonic acid of Formula B, wherein each R is independently selected from the group comprising halogens, amino acids, carboxylic acids and derivatives (ketones, esters, carboxylic acids); hydroxyl groups; amines; ethers; halogens; alkyl or aryl groups; or alkyl or aryl groups containing the abovementioned functional groups.

Formula B

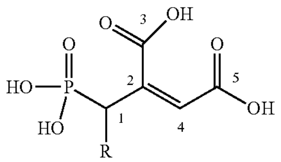

Another embodiment of the present disclosure provides a compound of Formula A wherein $R_1$ and $R_2$ are in the (Z) configuration.

Another embodiment of the present disclosure provides a compound of Formula A wherein $R_1$ and $R_2$ are in the (E) configuration.

Another embodiment of the present disclosure provides a compound of Formula A or Formula B wherein the chiral orientation is R.

Another embodiment of the present disclosure provides a compound of Formula A or Formula B wherein the chiral orientation is S.

Another embodiment of the present disclosure provides a compound of Formula A wherein $R_1$ and $R_2$ are COOH or COO—.

Another embodiment of the present disclosure provides a compound of Formula A wherein $R_1$ and $R_2$ are COOH or COO—, and one or both of the carboxylates is provided as a salt selected of the group comprising monovalent and divalent counterions.

Another embodiment of the present disclosure provides a salted form of the compound of Formula A and/or Formula B wherein the monovalent and divalent counterions are selected from the group consisting of sodium, potassium, calcium, lithium, magnesium, manganese, and mixtures thereof.

Another embodiment of the present disclosure provides a herbicidal formulation comprising the compound of Formula A and/or Formula B that is effective against plants.

Another embodiment of the present disclosure provides a salted form of the compound of Formula A and/or Formula B that is effective against monocot plants.

Another embodiment of the present disclosure provides a salted form of the compound of Formula A and/or Formula B that is effective against dicot plants.

Another embodiment of the present disclosure provides a salted form of the compound of Formula A and/or Formula B comprising water, one or more emulsifying agents, one or more surfactants, one or more wetting agents, and/or one or more pH buffering components, wherein the said composition has a pH between 5 and 9.

Another embodiment of the present disclosure provides a salted form of the compound of Formula A and/or Formula B comprising other bioactive agents, including other pesticides, adjuvants, or macro- or micro-nutrients.

Another embodiment of the present disclosure provides a method of biosynthesizing the compound of Formula A and/or Formula B using bacteria of the genus *Pantoea.*

Another embodiment of the present disclosure provides a method of biosynthesizing the compound of Formula A and/or Formula B using bacteria, wherein the bacterial strain is *Pantoea ananatis.*

Another embodiment of the present disclosure provides a method of biosynthesizing the compound of Formula A and/or Formula B using the bacteria *Pantoea* wherein the expression of the hvr gene cluster is modified.

Another embodiment of the present disclosure provides a method of biosynthesizing the compound of Formula A and/or Formula B using the bacteria *Pantoea*, which has been genetically modified to biosynthesize the compound of Formula A and/or Formula B in titers of >3 mg/L.

Another embodiment of the present disclosure provides a genetically modified bacterium wherein the expression of the hvr gene cluster has been modified to produce Formula A and/or Formula B.

Another embodiment of the present disclosure provides an herbicidal composition comprising the bacteria, bacterial-derived isolates, or supernatant of the bacteria of any of the foregoing embodiments that is effective against plants.

Another embodiment of the present disclosure provides an herbicidal composition of the foregoing embodiments that is effective against monocot plants.

Another embodiment of the present disclosure provides an herbicidal composition of the foregoing embodiments that is effective against dicot plants.

Another embodiment of the present disclosure provides a method for killing or suppressing a plant, which comprises contacting the plant with the herbicidal composition of the foregoing embodiments.

Another embodiment of the present disclosure provides a method of treating or preventing a fungal infection comprising the step of administering an antifungal amount of a compound or Formula A and/or Formula B to a patient in need thereof.

Another embodiment of the present disclosure provides a method of treating or preventing cancer comprising the step of administering a therapeutic amount of a compound or Formula A and/or Formula B to a patient in need thereof.

Another embodiment of the present disclosure provides a method of treating or preventing cancer comprising the step of administering a therapeutic amount of a compound or Formula A and/or Formula B to a patient in need thereof wherein the patient is a mammal and the cancer is glioblastoma.

A Phosphonate Natural Product Made by *Pantoea ananatis* is Necessary and Sufficient for the Hallmark Lesions of Onion Center Rot Although the indirect evidence for the involvement of a bioactive phosphonate in *P. ananatis* pathogenesis is strong, this has yet to be established. Here, we show that the hvr operon indeed encodes enzymes responsible for production of a small molecule phosphonate, which we show to be 2-(hydroxy(phosphono)methyl)maleate. The purified molecule, which we have designated pantaphos, has significant herbicidal activity and is able to produce the characteristic lesions of onion center rot in the absence of *P. ananatis*. Accordingly, this novel phosphonate natural product is both necessary and sufficient for onion rot pathogenesis. In addition, pathogenicity is enhanced in strains lacking phosphonate catabolism, suggesting that endogenous catabolism of pantaphos attenuates virulence.

Results

Role of phosphonate metabolism in onion center rot. To examine the broader role of phosphonate metabolism in onion pathogenesis, we characterized *P. ananatis* LMG 5342, which carries the hvr, pgb and phn loci, using *P. ananatis* B-14773, which does not encode any phosphonate biosynthetic genes, as a control. Because the pathogenicity of these strains has not been established, initial experiments were conducted to assess their ability to cause onion rot. Consistent with the previously observed correlation between the presence of the hvr locus and pathogenesis, we observed onion center rot in bulbs inoculated with strain LMG 5342, but not in bulbs inoculated with B-14773 (FIG. 1).

To verify that the observed pathogenic phenotype required hvr, and to examine whether the additional phosphonate metabolism genes play a role in pathogenesis, we constructed a series of LMG 5342 mutants lacking the hvr, pgb and phn loci in all possible combinations and scored their ability to cause onion rot (FIG. 1). The center rot phenotype was observed in all mutants that retained the hvr locus and absent in all strains with the Δhvr mutation. Therefore, as observed in *P. ananatis* OC5a, the hvr locus is necessary for onion pathogenicity in strain LMG 5342. In contrast, the pgb locus does not significantly contribute to pathogenicity, because the onion rot phenotype for mutants lacking these genes was identical to each of the otherwise isogenic strains. Interestingly, strains with intact hvr and phn loci were attenuated relative to those with the Δphn mutation, suggesting that endogenous phosphonate catabolism minimizes virulence (FIG. 1).

Production of phosphonic acids in *P. ananatis* LMG 5342. To examine whether phosphonates are actually produced by *P. ananatis* LMG 5342, we grew the wild-type strains in a variety of liquid and solid media. Spent media were then concentrated and screened for the presence of phosphonates using $^{31}P$ nuclear magnetic resonance (NMR), which allows relatively sensitive detection of molecules containing a carbon-phosphorus (C—P) bond, even in complex mixtures containing phosphate and phosphate esters. In no case did we observe signals consistent with the presence of phosphonates. We suspected that our inability to detect phosphonates in spent media was due to poor expression of the hvr operon in the media we employed. Thus, we conducted similar experiments in media supplemented with onion extract, with the idea that a plant metabolite was required to induce expression of the hvr locus; however, we failed to detect phosphonates in these media as well.

Figure 2:
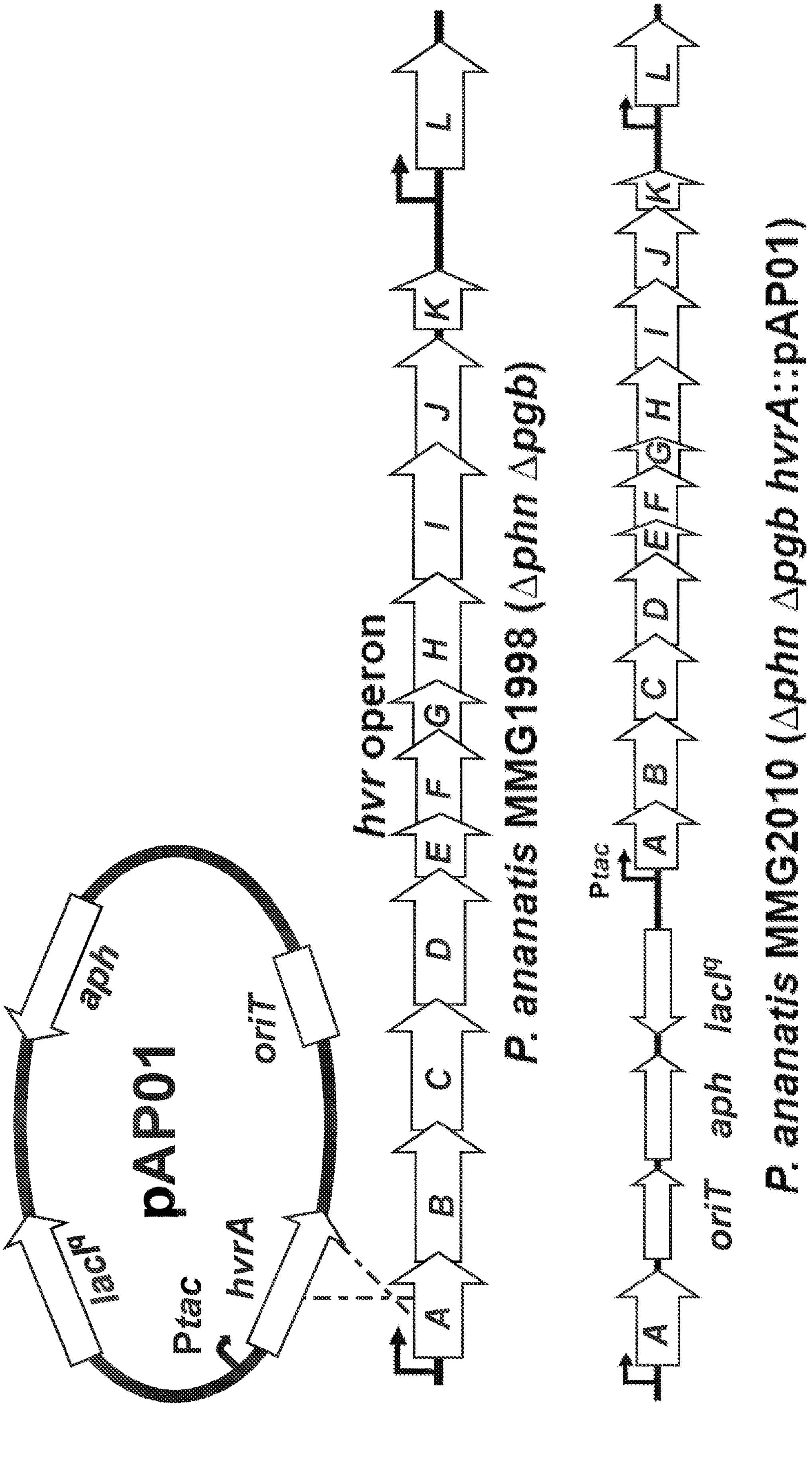
FIG. 2. Construction of a *P. ananatis* LMG 5342 derivative with IPTG-inducible hvr expression. Plasmid pAP01, which carries the hvrA gene under control of the IPTG-inducible Ptac promoter, was transferred to *P. ananatis* MMG1998 via conjugation from an *E. coli* donor. Because pAP01 is incapable of autonomous replication in *P. ananatis*, kanamycin-resistant (conferred by the aph gene) excongugants can only be obtained by chromosomal integration of the plasmid via homologous recombination (depicted as dotted lines). The resulting strain, *P. ananatis* MMG2010, expresses the entire hvr operon from the Ptac promoter. The positions of the native hvr promoters are shown as unlabeled bent arrows.
Figure 3:
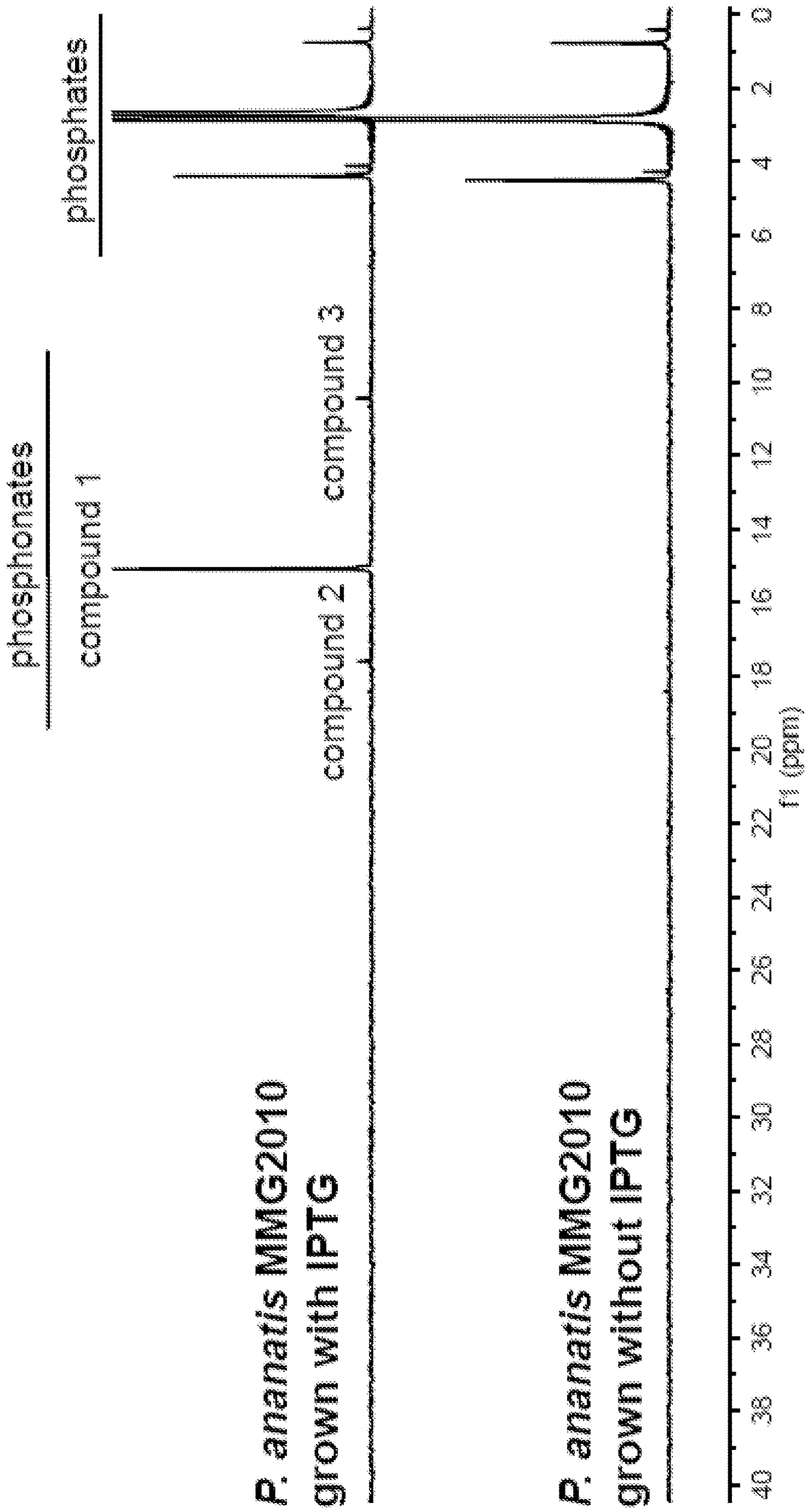
FIG. 3. Production of phosphonates is correlated with expression of the hvr operon. *P. ananatis* MMG2010, which expresses the hvr operon from an IPTG-inducible promoter, was grown in glycerol minimal medium with and without IPTG. Spent media were then concentrated and analyzed by $^{31}P$ NMR. Phosphonic acids typically produce peaks in the 5-30 ppm range, whereas peaks from phosphate and its esters and anhydrides typically have chemical shifts in the <5 ppm range.

To circumvent issues arising from native gene regulation, we constructed a strain that expresses the hvr operon from a strong, isopropyl-3-D-1-thiogalactopyranoside (IPTG)-inducible promoter (FIG. 2). To avoid complications caused by the other phosphonate metabolic genes, this strain also carried the Δphn and Δpgb mutations. After growth of this recombinant strain in media with IPTG, three distinct $^{31}P$ NMR peaks were observed (FIG. 3). The chemical shifts of these peaks ($\delta_P$ 17.6, δ15.0, and δ10.4 ppm) are consistent with the presence of molecules containing C—P bonds. These peaks were not observed after growth in media without IPTG. Thus, putative phosphonates are produced only when the hvr operon is expressed. After optimization of the medium and growth conditions, the IPTG-inducible strain catalyzed nearly complete conversion of phosphate to biomass and phosphonates, with final concentrations of approximately 0.653, 0.080, 0.039 mM for compounds 1; $^{31}P$ NMR (δ 17.6), 2 (δ15.0), and 3 (δ10.4 ppm), respectively.

Structure elucidation of hvr-related phosphonates. From a 3.2-liter culture grown using these optimized conditions, we were able to isolate 8.9 mg of pure compound 1 and small amount (<600 μg) of pure compound 2. Compound 3 ($\delta_P$ 10.42 ppm) was not obtained, because it is unstable at the low pH used during affinity chromatography (data not shown).

The structures of the compounds 1 and 2 were elucidated using a series of one- and two-dimensional carbon, phosphorus and proton NMR experiments (summarized in Table 1; the full data set is described in the Supplementary Dataset 2). Compound 1, which we designated pantaphos, was shown to be 2-(hydroxy(phosphono)methyl)maleate. Compound 2 (2-phosphonomethylmaleate) has a nearly identical structure, but lacks the hydroxyl-group, suggesting that it may be an intermediate in the biosynthesis of pantaphos (Table 1). High-resolution mass spectrometry data of the purified compounds are fully consistent with these structures (see Examples, FIG. 7).

TABLE 1

Summary of NMR data supporting the structure of compounds 1 & 2. Primary data and full description of structural elucidation is provided in the Examples.

$^1H—^{31}P$HMBC $^1H—^{13}C$HMBC

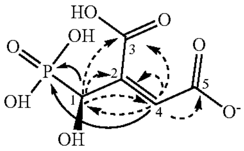

Compound 1 (pataphos)

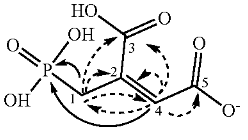

Compound 2

| position | $\delta_C$ (mult.; J in Hz) | $\delta_H$ (mult.; J in Hz) | $^1H$-$^{13}C$ HSQC | $^1H—^{13}C$ HMBC | $^1H—^{31}P$ HMBC | $^1H—^1H$ NOSEY/ COSY |
|---|---|---|---|---|---|---|
| Compound 1 (pantaphos) | | | | | | |
| 1 | 71.00 (d; 144.0) | 4.31 (d; 15.3) | Y | H1 → C2, C3, C4 | H1 → $\delta_P$ 15.40 ppm | H4 |
| 2 | 142.98 | | N | | | |
| 3 | 174.62 | | N | | | |
| 4 | 126.50 (d; 9.05) | 5.91 (d; 6.00) | Y | H4 → C1, C2, C3, C5 | H4 → $\delta_P$ 15.40 ppm | H1 |
| 5 | 175.20 | | N | | | |
| Compound 2 | | | | | | |
| 1 | 34.05 (d; 123.0) | 2.43 (d; 18.0) | Y | H1 → C2, C3, C4 | H1 → $\delta_P$ 18.47 ppm | H4 |
| 2 | 140.36 | | N | | | |
| 3 | 174.68 | | N | | | |
| 4 | 126.10 (d; 10.60) | 5.71 (d; 6.00) | Y | H4 → C1, C2, C3, C5 | H4 → $\delta_P$ 18.47 ppm | H1 |
| 5 | 177.02 | | N | | | |

Figure 4:
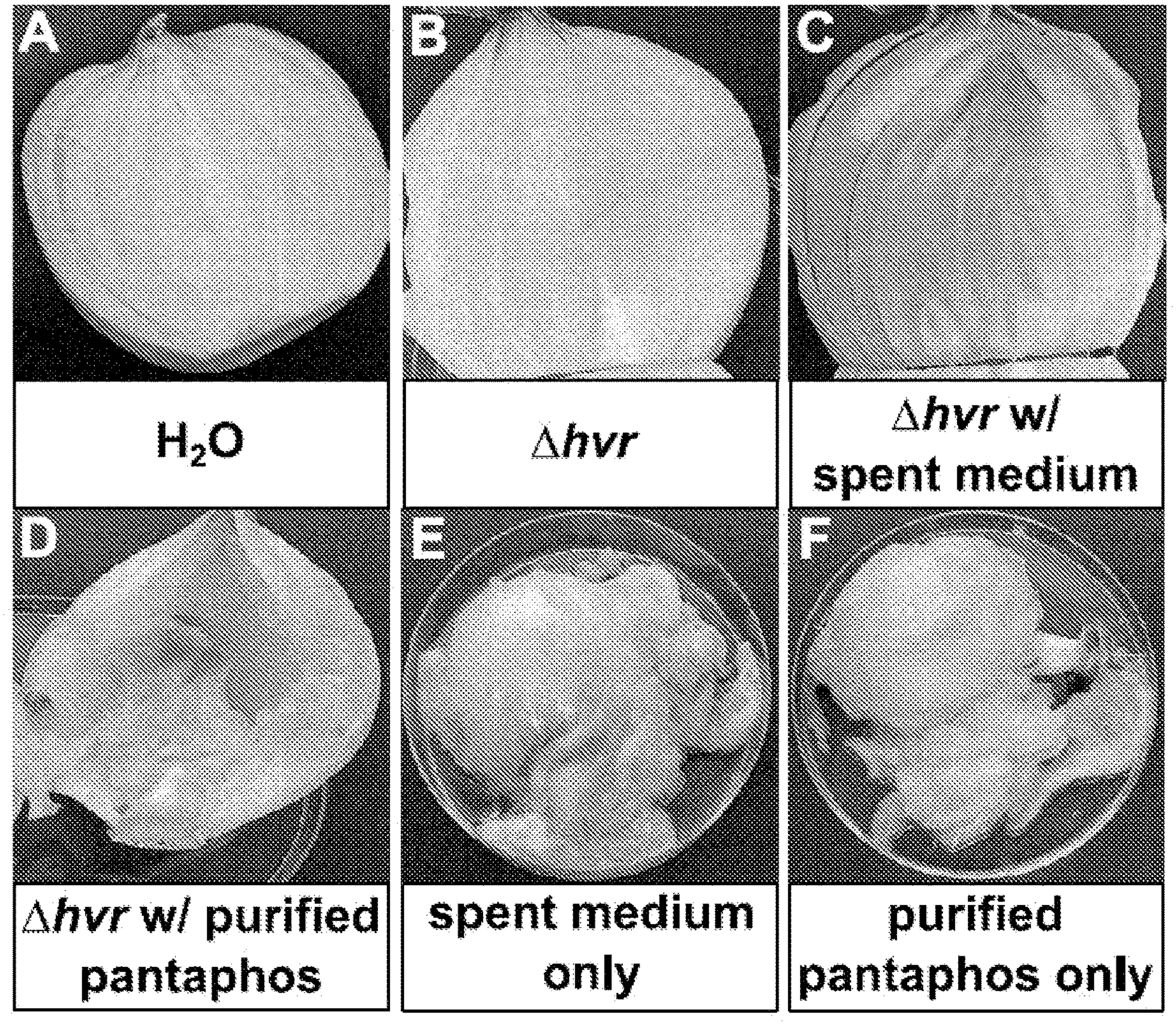
FIG. 4. Chemical complementation of the Δhvr onion rot phenotype by *P. ananatis* phosphonates. Surface sterilized onion bulbs were inoculated as indicated in each panel, then incubated at 30° C. for fourteen days prior to sectioning to reveal the center rot phenotype. Panels A and B show inoculations of a sterile water control and the Δhvr mutant. Panels C and D show inoculations with the hvr mutant supplemented with spent medium from an IPTG-induced culture of the phosphonate producing strain *P. ananatis* MMG2010 or purified pantaphos. Panels E-F show inoculations of onion with sterile spent medium or purified pantaphos in the absence of bacteria.

Lesions of onion center rot are caused by pantaphos. To investigate the role of hvr-associated phosphonates in pathogenesis, we repeated the onion rot assay using concentrated culture supernatants or purified pantaphos in the presence and absence the *P. ananatis* Δhvr mutant (FIG. 4). (Pure compound 2 was not obtained in sufficient quantities to allow bioactivity testing.) As described above, onions inoculated with *P. ananatis* Δhvr mutants showed minimal damage. However, when concentrated spent medium from IPTG-induced cultures of the phosphonate over-producing strain was co-inoculated with the Δhvr mutant, center rot was again observed. Similarly, co-inoculation with purified pantaphos also resulted in onion rot. Significantly, onions injected with either concentrated spent medium or purified pantaphos showed severe onion rot lesions in the absence of bacteria. The occurrence of center rot was dose-dependent with the characteristic lesions observed using as little as 90 μg (0.40 μmol) of pantaphos. Therefore, pantaphos is both necessary and sufficient to cause the center rot lesions in onions.

Figure 5:
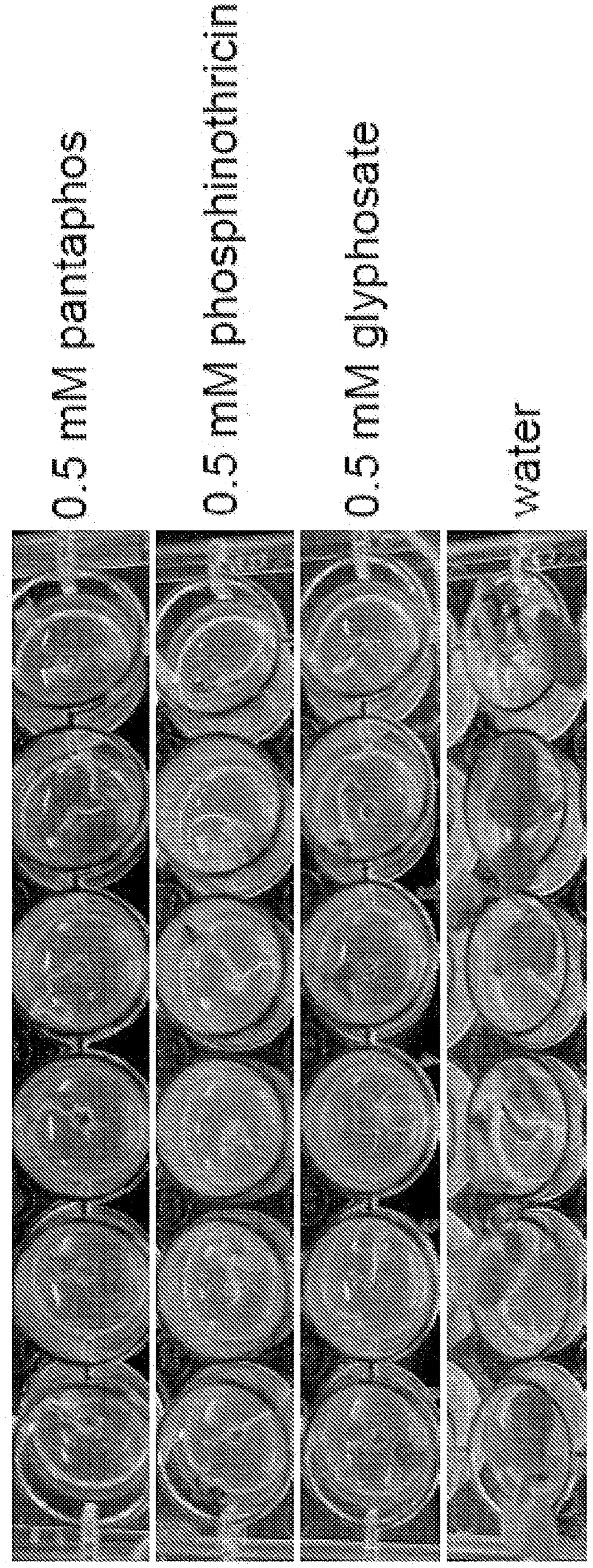
FIG. 5. Phytotoxicity of pantaphos compared to known herbicides. Mustard seedlings were treated as indicated and incubated at 23° C. under 16-hour light cycle for seven days. Panel A shows the observed phenotype after incubation with the indicated compounds. Panels B and C show root length and dry weight of each replicate after incubation. A Welch's t-test was performed to establish significant differences between the means of each treatment (*P-value<0.001, P-value<0.01, *P-value<0.05; N=6 per treatment). Error bars represent the standard error of the mean.
Figure 5:
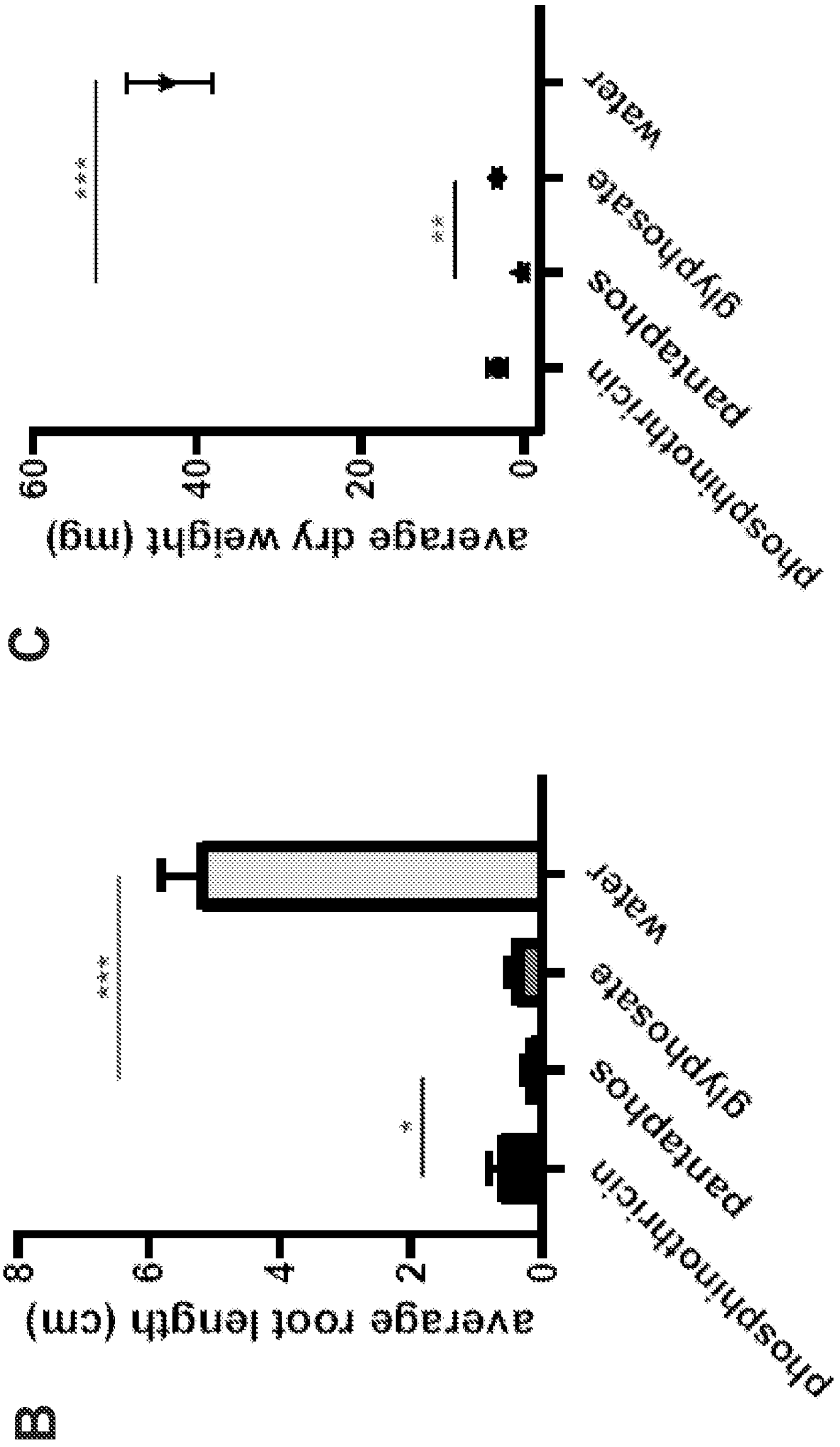
Figure 6:
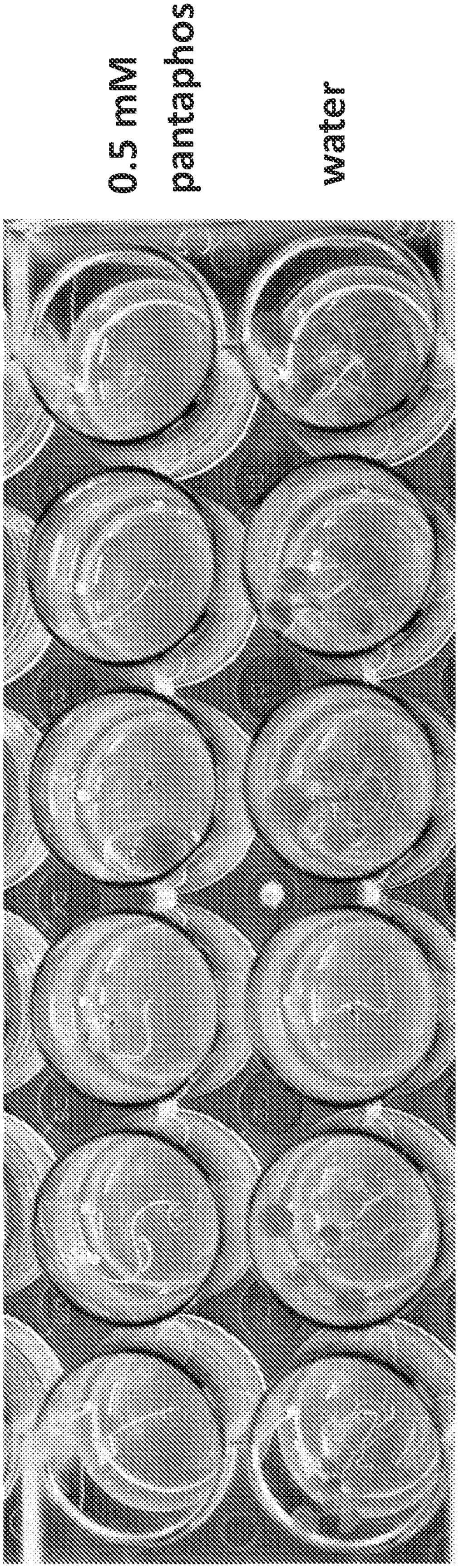
FIG. 6. Phytotoxicity of pantaphos against *Arabidopsis thaliana* Col-0. *A. thaliana* Col-0 seedlings were treated as indicated and incubated at 23° C. at 60% humidity under 16-hour light cycle for seven days. A Welch's t-test was performed to calculate statistics between the means of the different treatments (*P-value<0.001, P-value<0.01, *P-value<0.05; N=6 per treatment). Error bars represent the standard error of the mean.
Figure 6:
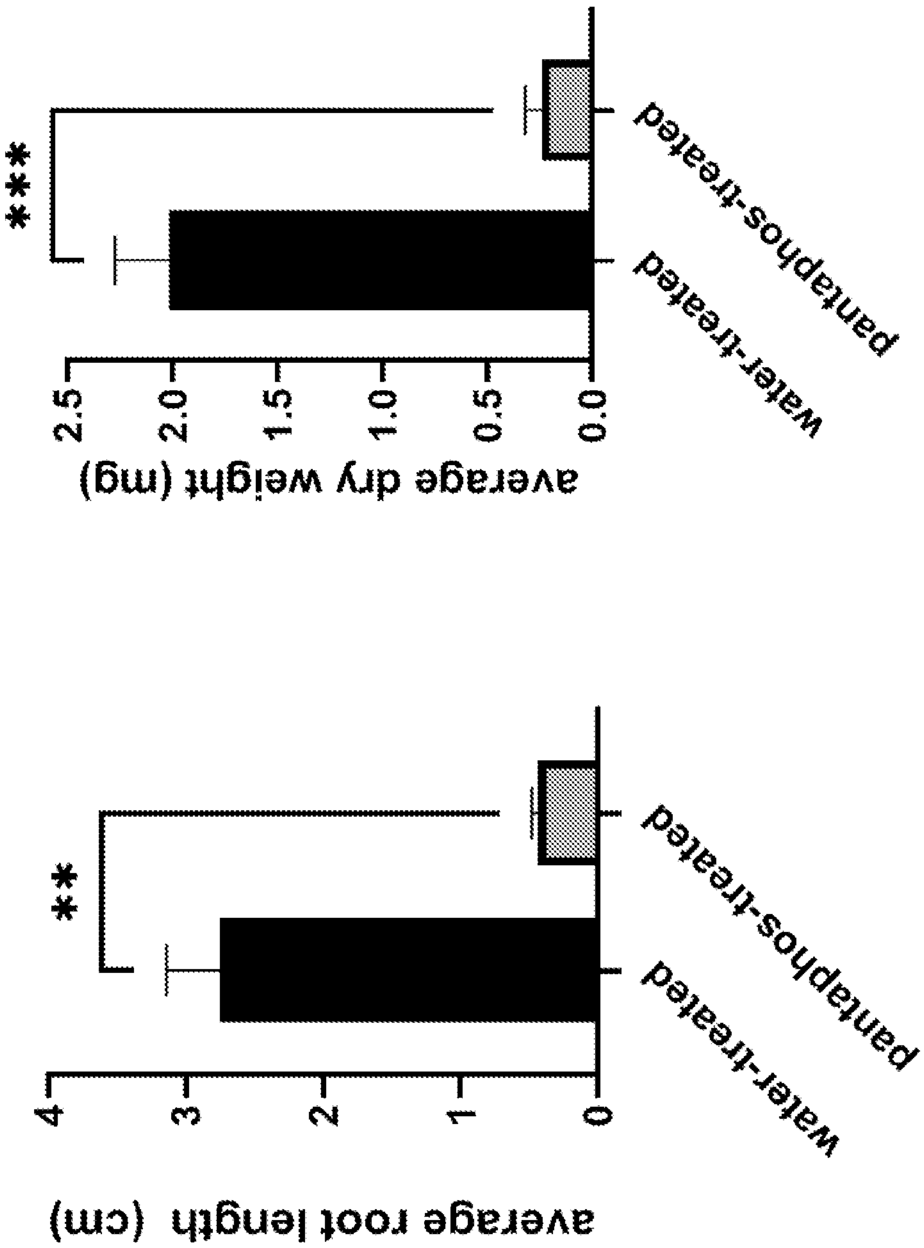

Phytotoxic effects of pantaphos treatment are comparable to known herbicides. To test whether the phytotoxicity observed in onion bulbs could be extended to growing plants, we treated newly germinated mustard seedlings (*Brassica* sp.) and *Arabidopsis thaliana* Col-0 seedlings with purified pantaphos using two well-characterized phosphonate herbicides (glyphosate and phosphinothricin) as controls (FIG. 5 and FIG. 6). After seven days growth, all three compounds caused a substantial reduction in root length and total dry weight of the seedlings relative to water-treated controls, with pantaphos being significantly more potent than phosphinothricin in the root length assay and than glyphosate in the dry weight assays. The phytotoxicity of pantaphos was dose-dependent with significant activity at concentrations 1.95 μM and above in the root length assay and above 31.3 μM in the dry weight assay.

Cytotoxic, antibacterial, and antifungal bioactivities of pantaphos. To examine whether bioactivity of pantaphos was specific to plants, we also conducted a series of bioassays against human cell lines, bacteria and fungi. Pantophos showed modest cytotoxicity to several human cell lines (Table 2). With the exception of one ovarian cancer cell line (ES-2), which was unaffected at the maximum dose, the $IC_{50}$ levels were roughly similar, in the range of 6.0 to 37.0 μM for each of the cell lines tested. One glioma cell line (A-172) was especially sensitive to pantaphos ($IC_{50}$ of 1.0 μM). In contrast, the molecule had no effect on the growth of fungi in rich or minimal media, including *Candida albicans, Aspergillus fumigatus* and two strains of *Saccharomyces cerevisiae* (Table 2). Similarly, a variety of Gram-negative and Gram-positive bacteria, including all of the so-called ESKAPE pathogens, were insensitive to pantaphos in both minimal and rich media (Table 2). To examine whether the insensitivity of *E. coli* was due to a lack of transport, we also tested bioactivity using the phosphonate-specific bioassay strain *E. coli* WM6242, which carries two copies of an IPTG-inducible, broad substrate-specificity phosphonate transporter. This strain was insensitive to pantaphos, with or without IPTG induction, suggesting that the lack of bioactivity in *E. coli* is not due to poor transport of the molecule.

TABLE 2

Bioactivity of pantaphos against human cells and microorganisms.

| Human cell line | $IC_{50}$ (μM)[a] | |
|---|---|---|
| HOS (human osteosarcoma) | 36.98 + 6.28; $E_{max}$ 58% | |
| ES-2 (human ovarian cancer) | >100 | |
| HCT-116 (human colon cancer) | 10.42 + 2.00; $E_{max}$ 59% | |
| A-549 (human lung carcinoma) | 14.73 + 0.61; $E_{max}$ 66% | |
| HFF-1 (human fibroblast cells) | 6.69 + 0.29; $E_{max}$ 85% | |
| A-172 (human glioma cancer) | 1.01 + 0.06; $E_{max}$ 99% | |
| | MIC (μM) for:[b] | |
| Fungi | Rich medium | Minimal medium |
| *Candida albicans* SN250 | >125 | n.t.[c] |
| *Aspergillus fumigatus* 1163 | >125 | >125 |
| *Saccharomyces cerevisiae* X2180-1A | >125 | >62.5 |
| | MIC (μM) for:[d] | |
| Bacteria | Rich medium | Minimal medium |
| *Enterococcus faecalis* ATCC 19433 | >200 | n.t.[c] |
| *Staphylococcus aureus* ATCC 29213 | >200 | >200 |
| *Klebsiella pneumoniae* ATCC 27736 | >200 | >200 |
| *Acinetobacter baumannii* ATCC 19606 | >200 | >200 |
| *Pseudomonas aeruginosa* PAO1 | >200 | >200 |
| *Escherichia coli* ATCC 25922 | >200 | >200 |
| *Salmonella enterica* LT2 | >200 | >200 |
| *Escherichia coli* WM6242 -IPTG | >200 | >200 |
| *Escherichia coli* WM6242 +IPTG | >200 | >200 |

[a]50% inhibitory concentration determined using the Alamar Blue method. Emax = percentage cell death.
[b]Minimum inhibitory concentration (MIC) determined based on CLSI guidelines after 48 hrs growth. Bioactivity in rich medium was determined using RPMI 1640 medium. Bioactivity in minimal medium was determined using M9 minimal medium.
[c]Not tested because the organism does not grow in minimal medium.
[d]Minimum inhibitory concentration (MIC) determined based on CLSI guidelines. Bioactivity in rich medium was determined using Mueller-Hinton 2 medium and bioactivity in minimal medium was determined using glucose-MOPS minimal medium.

Figure 7:
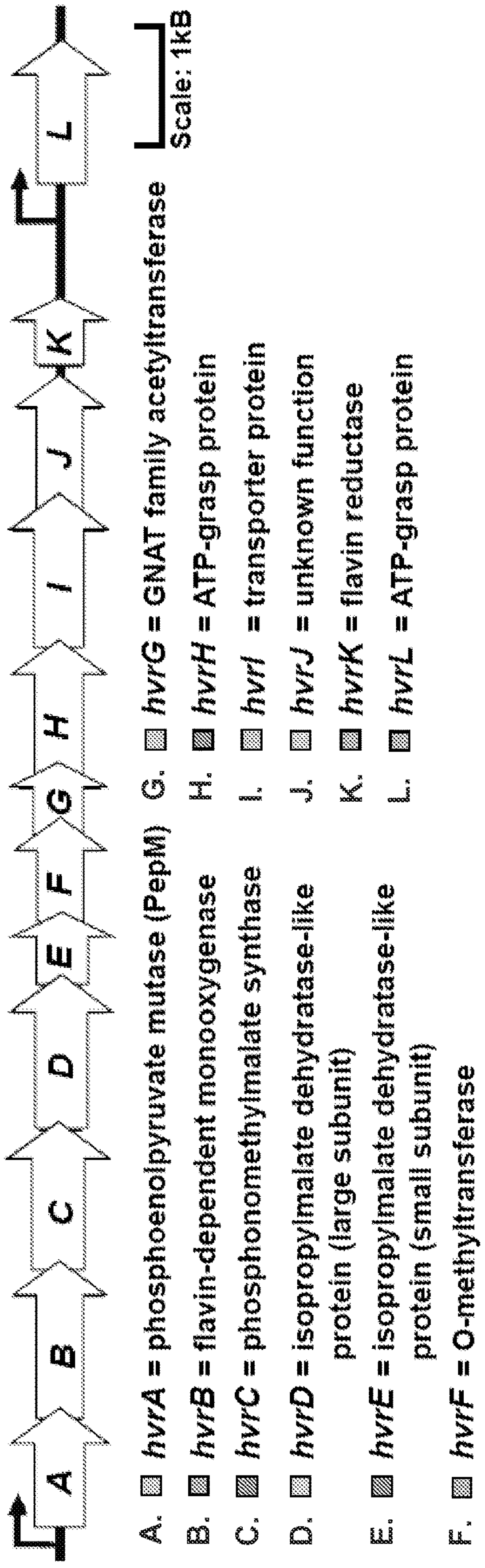
FIG. 7. Hvr biosynthetic gene cluster in *P. ananatis* LMG 5342 and the proposed biosynthetic pathway. The proposed protein functions of the Hvr BGC genes based on BLAST searches and conserved protein domain analyses.

Putative functions of the hvr-encoded proteins and proposed pantaphos biosynthetic pathway. Combining the structures determined above with the proposed functions of the Hvr proteins suggests reasonable biosynthetic route for the *P. ananatis* phosphonates (FIG. 7). As with most phosphonate natural products, the pathway begins with the rearrangement of phosphoenolpyruvate (PEP) to phosphonopyruvate (PnPy) catalyzed by the enzyme PEP mutase. In *P. ananatis*, this reaction would be catalyzed by the HvrA protein, which is highly homologous to known PEP mutases. Because the PEP mutase reaction is highly endergonic (ΔG~125 kJ/mol), subsequent steps must be highly favorable to drive net phosphonate synthesis. In the proposed pathway, this thermodynamic driving force is provided by the exergonic condensation of acetyl-CoA and phosphonopyruvate (PnPy) catalyzed by the HvrC protein, which is a homolog of the biochemically characterized phosphonomethylmalate (PMM) synthase involved in FR-900098 biosynthesis. PMM would then be dehydrated to form 2-phosphonomethylmaleate by HvrD and HvrE. These proteins are homologs of the small and large subunits of isopropylmalate dehydratase, respectively, which catalyze the isomerization of 3-isopropylmalate to 2-isopropylmalate via a dehydrated intermediate (2-isopropylmaleate) during leucine biosynthesis. We expect that HvrDE will not catalyze the full reaction, but rather stop at the dehydrated intermediate. Precedent for this partial reaction is found in the propionate catabolic pathway of some bacteria, which catalyze the dehydration of 2-methylcitrate to 2-methyl-cis-aconitate using a member of the isopropylmalate dehydratase family. Conversion of 2-phosphonomethylmaleate to pantaphos is likely to be catalyzed by HvrB, a homolog of the flavin-dependent monooxygenases, NtaA and ScmK (48% and 47% identity, respectively). Consistent with the idea that this is an oxygen dependent reaction, we have observed that poorly aerated cultures accumulate 2-phosphonomethylmaleate instead of pantaphos. Flavin-dependent monooxygenases often require a separate flavin reductase to provide the electrons needed for reduction of oxygen to water. We propose that this function is provided by HvrK, a member of the flavin reductase family that is 30% identical to NtaB, which serves this function in the analogous NtaA-catalyzed reaction. Finally, we suggest that the HvrI protein, which is a member of the major facilitator superfamily, is responsible for export of the phosphonate products.

The proposed pathway for pantaphos biosynthesis uses only seven of the eleven genes in the hvr operon (Scheme 1). Based on homology to proteins of known function, three of remaining genes are predicted to encode an O-methyltransferase (HvrF), an N-acetyltransferase (HvrG) and an ATP-Grasp family protein (HvrH). The final unassigned protein (HvrJ) has no characterized homologs and, thus, we cannot predict a function. A twelfth protein that may, or may not, be part of the hvr operon also encodes an ATP-Grasp family protein (HvrL). Members of the ATP-Grasp family of enzymes often catalyze peptide bond formation. Accordingly, we suspect that peptidic derivatives of pantaphos may be produced by *P. ananatis*. Considering the absence of nitrogen in pantaphos, a peptidic derivative could also help explain the presence of the putative N-acetyltransferase HvrG, which might act as a self-resistance gene similar to the pat gene that confers self-resistance during biosynthesis of phosphinothricin tripeptide. Finally, the putative O-methyltransferase HvrF is highly homologous to trans-acontitate methyltransferase, which is thought to be involved in resistance to the spontaneously formed trans isomer of this TCA cycle intermediate. An analogous role can be envisioned for HvrF, if similar trans isomer side products are produced during pantaphos biosynthesis.

Scheme 1. The proposed biosynthetic pathway based on the structures of the *P. ananatis* phosphonates determined in this study pantaphos and the biosynthetic logic of analogous reactions catalyzed by homologs of the Hvr proteins. PEP=phosphoenolpyruvate; PnPy=phosphonopyruvate; PMM=phosphonomethylmalate; IPMS=isopropylmalate synthase; IPMD=isopropylmalate dehydratase; ace-CoA=acetyl coenzyme A.

Analogus TCA cycle reactions

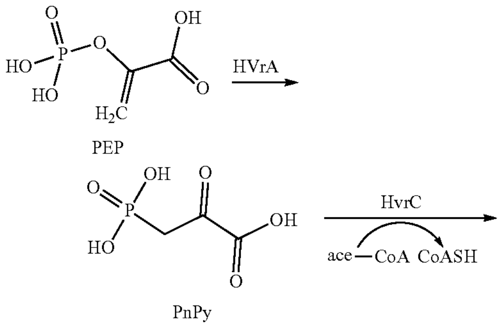

-continued

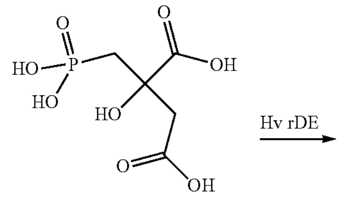

PMM

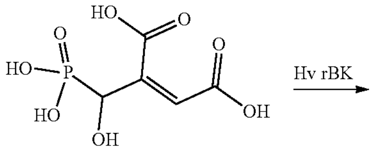

2-phosphonomethyl-maleate

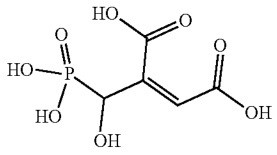

2-hydroxyphosphonomethyl-maleate (pantaphos)

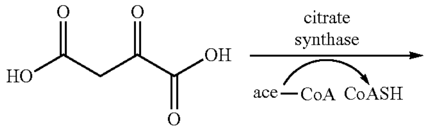

oxaloacetate

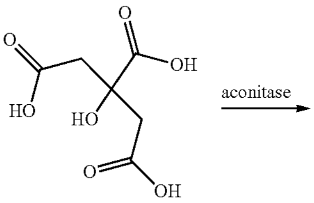

citrate

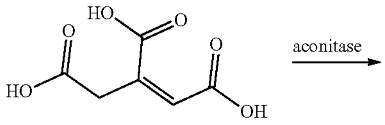

cis-aconitate

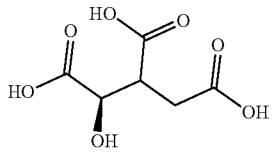

isocitrate

Analogous leucine biosnthesis reactions

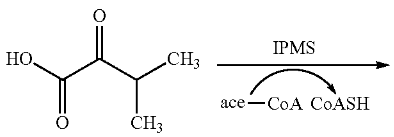

3-methyl-2-oxobutanoate

-continued

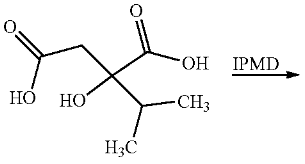

2-isopropy Imalate

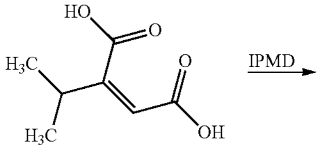

2-isopropy Imaleate

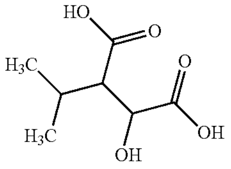

3-isopropy Imaleate

Homologs of the hvr operon in other bacteria. Asselin et al noted the presence of gene clusters similar to the hvr operon in a number of bacterial genome sequences. We felt it was worth revisiting this analysis in the light of the structures identified above. A total of thirty-three related gene clusters were identified in the NCBI genomic sequence databases using a combination of bioinformatics approaches. Based on the arrangement and the presence or absence of orthologous genes, nine types of Hvr-like biosynthetic gene clusters were observed. Putative orthologs of HvrA-F are conserved in all of these groups, with the exception of Type VIII, which replaces the HvrDE proteins with a putative aconitase. As shown in FIG. 6, aconitase catalyzes a reaction that is essentially identical to the putative HvrDE reaction. Thus, we predict that the biosynthetic pathway encoded by the Type VIII hvr-like gene cluster has identical intermediates produced by paralogous enzymes. A feature that differentiates the nine types of hvr-like clusters is the presence or absence of one or more ATP-Grasp proteins, suggesting that a variety of peptidic derivatives of pantaphos might be produced in Nature. However, Type IX, which lacks ATP-grasp family proteins, likely has very different structural modifications compared to the other types, based on the presence of homologs to several additional enzyme families. Finally, the clusters also differ with respect to their putative export proteins and the presence/absence of a putative flavin reductase. The latter is not unexpected, as many flavin dependent enzymes can utilize generic reductases encoded by unlinked genes. Interestingly, the hvr-like clusters identified in our search were only found in a few of lineages within the proteobacteria and actinobacteria.

DISCUSSION

The phosphonate natural products produced by *P. ananatis* LMG 5342 are the principal virulence factor involved in onion center rot. Indeed, our data show that application of purified pantaphos produces identical lesions in the absence of bacteria. Although bioactive phosphonate natural products are well known, data supporting a direct role for these molecules in pathogenesis are rare. To date the sole known example is a complex phosphonate-modified polysaccharide produced by *Bacteroides fragilis*, which was shown to promote abscess formation in the mammalian gut. The demonstration that pantaphos is both necessary and sufficient for onion center rot adds a second phosphonate natural product to this short list and confirms the predicted function of the *P. ananatis* hvr locus proposed by Asselin et al (Mol Plant Microbe Interact 2018, 31:1291).

Despite the fact that unmodified pantaphos is phytotoxic, it seems likely that modified derivatives of the compound are also produced by *P. ananatis*. As described above, the hvr locus encodes two ATP-Grasp proteins. Members of this protein family often catalyze the ATP-dependent formation of peptide bonds, including those found in the peptidic phosphonate natural products rhizocticin, plumbemycin and phosphonoalamide. Addition of amino acid substituents often enhances uptake of bioactive compounds. For example, phosphinothricin tripeptide is a potent antibacterial compound, while unmodified phosphinothricin has poor activity. It should be noted, however, that these transport-mediated effects are species specific. Thus, phosphinothricin and phosphinothricin tripeptide are equally effective herbicides. A particularly striking example of specificity conferred by amino acid substituents is seen in the bioactivity profile of rhizocticin and plumbemycin. These natural products have the same bioactive phosphonate warhead attached to different amino acids, which presumably governs their uptake by specific peptide transport systems. As a result, rhizocticin is a potent antifungal agent that lacks antibacterial activity; whereas plumbemycin is a potent antibacterial that lacks antifungal activity. Based on these precedents, we suspect that peptidic derivatives of pantaphos may be produced during plant infection that increase its potency or specificity for a particular target species, perhaps accounting for the unstable compound 3 we observed in spent media.

Interestingly, pantaphos is not the only phosphonate produced by *P. ananatis* species. At least four distinct phosphonate biosynthetic gene clusters can be found in the currently sequenced *P. ananatis* genomes. With the exception of the hvr operon, neither the structures, nor the biological functions of the molecules produced by these gene clusters can be suggested at this time; however, our data clearly show that the pgb cluster is not required for onion center rot. Significantly, the strict correlation between plant pathogenicity and the presence of the hvr operon breaks down when larger numbers of *Pantoea* genomes are analyzed. Accordingly, *P. ananatis* strains PA4, PNA 14-1 and PNA 200-3 lack the hvr operon, but still cause onion disease; whereas strains PANS 04-2, PNA 07-10 and PNA 200-7 carry the hvr locus, but do not cause the disease. These data indicate that additional virulence traits are important for onion pathogenesis in *Pantoea* species. They also demonstrate the need for caution when using the presence/absence of the hvr cluster as a marker for plant pathogenicity.

Gene clusters similar to the hvr locus are relatively common in sequenced bacterial genomes; however, their phylogenetic distribution is rather restricted. Interestingly, many of the bacteria encoding these hvr-like gene clusters are associated with either plant or insect hosts. Homologs of the hvr operon are particularly abundant in members of the closely related *Photorhabdus* and *Xenorhabdus* genera. These bacteria have a unique lifestyle that relies on infection of an insect host via a nematode vector. Similarly, an hvr-locus is found in *Bartonella senegalensis* OS02, a putative intracellular pathogen of mammals. Given the cytotoxic effects we observed in human cells, it is tempting to suggest that pantaphos-like compounds may be involved in bacterial pathogenesis in both insects and humans. Homologs of the hvr operon are also seen in several members of the actinobacteria, including species of *Streptomyces*. These bacteria, which are common epiphytes and endophytes, are known for their production of a wide array of secondary metabolites including antibacterial, antifungal and phytotoxic compound. Thus, it seems likely that bioactive pantaphos-like molecules are important for mutualistic interactions of actinobacteria as well.

The idea that pantaphos and its putative derivatives are involved in diverse mutualistic interactions begs the question of the biological target for these molecules. Amongst the organisms tested to date, only plants and human cells show significant sensitivity to pantaphos, while bacteria and fungi were completely insensitive to the molecule. A simple explanation for these observations is that the target is shared by plants and animals and absent from bacteria and fungi. Alternatively, the target could be shared by all organisms, but be sufficiently different in bacteria and some fungi that it is not sensitive to the molecule. It is also possible that bacteria and some fungi share the ability to inactivate pantaphos, or that they are incapable of transporting the molecule into their cells. Significant experimental effort, beyond the scope of this initial report, will be required to distinguish between these possibilities; however, at least for *E. coli*, the data suggests that lack of transport is not responsible for the absence of bioactivity. Possible targets for pantaphos can be envisioned based on the structure of pantaphos, which is similar to a number of common metabolites including citrate, isocitrate, aconitate, isopropylmalate and maleate. Because most characterized phosphonates act as molecular mimics of normal cellular metabolites, this suggests the possibility that pantaphos may target the TCA cycle or leucine biosynthesis. Because maleic acid compounds are known to inhibit transaminases, it is also possible that the molecule inhibits the synthesis of another essential amine-bearing metabolite.

Finally, the studies described here have significant agricultural implications, which provide strong motivation for future studies on the biosynthesis and molecular target of pantaphos, as well as potential mechanisms for resistance to the compound. The identification of pantaphos as the principal virulence factor in onion rot suggests multiple approaches to deal with agricultural infestations of *Pantoea ananatis*. Because the molecule is required for virulence, it seems likely that inhibitors of the pantaphos biosynthetic pathway would prevent plant infection. It should also be possible to identify the molecular target of the compound in plants using purified or synthetic pantaphos, which would pave the way for development of crops with resistant alleles that would be immune to the disease. Plants expressing the putative pantaphos-modifying enzymes encoded by the hvr locus, or unrelated phosphonate catabolic genes, would also be expected to be specifically resistant to *Pantoea* infection. Finally, there is a desperate need to develop new treatments that are effective in combatting the alarming rise of herbicide-resistant weeds. The potent phytotoxicity of pantaphos suggests that it may have agricultural utility similar to that of the widely used phosphonate herbicides glyphosate and phosphinothricin. The real possibility of developing pantaphos-resistant crops strengthens this idea, as does the absence of bioactivity towards bacteria and fungi, suggesting that the molecule would have minimal effects on the soil microbiome. A note of caution is appropriate, however, given the moderate cytotoxicity we observed in human cell lines.

General Synthetic Methods

The invention also relates to methods of making the compounds and compositions of the invention. The compounds and compositions can be prepared by any of the applicable techniques of organic synthesis, for example, the techniques described herein. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure,* $5^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compounds of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically, the temperatures will be −100° C. to 200° C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about 20° C.), although for metal hydride reductions frequently the temperature is reduced to 0° C. to −100° C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group" refers to any group which, when bound to a hydroxy or other heteroatom prevents undesired reactions from occurring at this group and which can be removed by conventional chemical or enzymatic steps to reestablish the hydroxyl group. The particular removable protecting group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TBDPS), or t-butyldimethylsilyl (TBS)) and any other group that can be introduced chemically onto a hydroxyl functionality and later selectively removed either by chemical or enzymatic methods in mild conditions compatible with the nature of the product.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Herbicidal Formulations

In general, agrochemical formulations especially liquid form comprises either inorganic or organic solvents. Most of the known organic solvents known in the art are non-biodegradable and highly flammable. Organic solvents-based agrochemical formulations generally use a solvent that is preferably water-immiscible to dissolve the active component completely and produces a clear homogenous liquid free from extraneous matter. Alternatively, organic solvents typically have a low flash point, are non-biodegradable, cause skin irritation and possess medium or high evaporation rate etc. but provide a clear homogenous liquid. The known agrochemical compositions further include at least a surfactant wherein the performance and dosage of the included surfactant is based on the active content and solvent in the formulation, type of active ingredient, and solubility of the active ingredient in the solvent and the required emulsion performance of the final product.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), 4,820,508 (Wortzman), 4,608,392 (Jacquet et al.), and 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compositions described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 $mg/m^2$, conveniently 10 to 750 $mg/m^2$, most conveniently, 50 to 500 $mg/m^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, brain cancer, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

Examples

Example 1. Methods and Materials

We constructed a *P. ananatis* LMG 5342 recombinant strain able to produce high quantities (>3 mg per liter) of a natively produced phosphonic acid small molecule produced from a biosynthetic gene cluster within a pathogenicity island (aka "HiVir" or hvr) of this bacterium. We have isolated and purified the small molecule and found it to be (2E)-3-carboxy-4-hydroxy-4-phosphonobut-2-enoate (compound 1) based on our nuclear magnetic resonance and mass spectrometry analyses. This small molecule acts in an herbicidal manner based on our data from herbicide bioassays with onion and mustard seedlings. The exact mechanism of action is unknown, but it produces similar toxicity as does the known herbicides phosphinothrcin and glyphosate. The DNA and protein sequences of *P. ananatis* may be found at ATGC database as disclosed in Kristensen et al., Nucleic Acids Res. 2017 Jan. 4; 45(D1):D210-D218. The ATGC database is hosted jointly at the University of Iowa at dmk-brain.ecn.uiowa.edu/ATGC/and the NCBI at ftp.ncbi.nlm.nih.gov/pub/kristensen/ATGC/atgc_home.html or at ftp.ncbi.nlm.nih.gov/pub/kristensen/ATGC/atgc_list.html. The database accession numbers for the nucleic acid sequences of the genes of the hvr operon of *P. ananatis* are hvrA (WP_013027161.1), hvrB (WP_041455823.1), hvrC (WP_013027159.1), hvrD (WP_014605075.1), hvrE (WP_013027157.1), hvrF (WP_013027156.1), hvrG (WP_014605077.1), hvrH (WP_013027154.1), hvrI (WP_013027153.1), hvrJ (WP_014605079.1) hvrK (WP_013027151.1), and hvrL (WP_013027150.1). Whole genome sequences of *P. ananatis* also may be found using Genbank accession number HE617160.1, NC_016816.1, HE617161.1, or NC_016817.1

Bacteria, plasmids and growth conditions. Bacterial strains, plasmids and primers used in this study are described in Table 3 and 4. General chemical and molecular biology reagents were purchased from Sigma-Aldrich or New England Biolabs. Phosphinothricin (glufosinate) was purchased from GoldBio (CAS #77182-82-2). Standard bacterial growth media were prepared as described (Current Protocols in Molecular Biology 2019, 125:e81, e82, e83). *E. coli* strains were typically grown at 37° C.; *P. ananatis* strains were typically grown at 30° C. Phosphonate induction media (PIM) was prepared as follows: 8.37 g/L MOPS, 0.72 g/L Tricine, 0.58 g/L NaCl, 0.51 g/L $NH_4Cl$, 1.6 g/L KOH, 0.1 g/L $MgCl_2 \cdot 6H_2O$, 0.05 g/L $K_2SO_4$, 0.2 g/L $K_2HPO_4$ were dissolved $H_2O$ and steam sterilized for 20 min at 121° C. After cooling, 1× sterile trace element solution was added (1000× stock: 1.5 g/L nitrilotriacetic acid trisodium salt, 0.8 g/L $Fe(NH_4)_2(SO_4)_2 \cdot 7H_2O$, 0.2 g/L $Na_2SeO_3$, 0.1 g/L $COCl_2 \cdot 6H_2O$, 0.1 g/L $MnSO_4 \cdot H_2O$, 0.1 g/L $Na_2MoO_4 \cdot 2H_2O$, 0.1 g/L $Na_2WO_4 \cdot 2H_2O$, 0.1 g/L $ZnSO_4 \cdot 7H_2O$, 0.1 g/L $NiCl_2 \cdot 6H_2O$, 0.01 g/L $1H_3BO_3$, 0.01 g/L $CuSO_4 \cdot 5H_2O$) followed by addition of 1% (v/v) sterile glycerol and 50 μg/mL sterile kanamycin. For culturing of *Candida* and *Saccharomyces* strains, Rosewell Park Memorial Institute 1640 medium (RPM; Sigma-Aldrich R6504) was used for liquid culturing and Sabouraud Dextrose Agar (SDA; Difco™ 210950) for solid plating unless otherwise specified. For *Aspergillus* strains, Rosewell Park Memorial Institute 1640 medium (RPMI) was used for liquid culturing and Potato Dextrose Agar (PDA; Difco™ 213400) was used for solid plating unless otherwise specified. YMM medium (6.7 g/L yeast nitrogen base without amino acids [BD Difco™ 291940], 20 g/L glucose, X trace element solution) was used as minimal media for fungal strains.

TABLE 3

Microorganisms used in this study.

| Strain | Genotype/Construction | Source/ Reference |
|---|---|---|
| *Escherichia coli* | | |
| DH5a/ Apir | F- endAl glnV44 thi-1 recAl relAl gyrA96 deoR nupG Φ80dlacZ ΔM15 Δ(lacZYA-argF)U169, hsdR17(rK- mK+), λpir | a, b |
| WM6026 | lacI$^q$, rrnB3, ΔlacZ4787, hsdR514, ΔaraBAD567, ΔrhaBAD568, rph-1, attλ::pAE12(ΔoriR6K-cat::Frt5), ΔendA::Frt,uidA(ΔMluI)::pir,attHK::pJK1006 Δ(oriR6K-cat::Frt5;trfA::Frt) | c |
| WM6242 | lacI$^q$, rrnB3, Δ(lacZ4787), hsdR514, attP22(EcoB), Δ(araBAD)567, A(rhaBAD)568, rph-1, Δ(phnC-P), Δ(phoA), HKattB::pJK077(ΔaadA-oriR6K), lambda-attB::pJK074(Δcat-oriR6K) | d |
| *Pantoea ananatis* | | |
| LMG 5342 | Native phosphonate producer | ATCC #22920 |
| B-133 | wild-type | ARS NRRL |
| B-14773 | wild-type | ARS NRRL |
| MMG1888 | Δpgb Δhvr; Markerless deletion in MMG1984 using allele exchange plasmid pAP04 | This study |
| MMG1904 | Δphn; Markerless deletion in LMG 5342 using allele exchange plasmid pAP05 | This study |
| MMG1912 | Δhvr; Markerless deletion in LMG 5342 using allele exchange plasmid pAP04 | This study |
| MMG1920 | Δphn Δhvr; Markerless deletion in MMG1904 using allele exchange plasmid pAP04 | This study |
| MMG1984 | Δpgb; Markerless deletion in LMG 5342 using allele exchange plasmid pAP02 | This study |
| MMG1988 | Δpgb Δphn; Markerless deletion in MMG1904 using allele exchange plasmid pAP02 | This study |
| MMG2010 | Δphn Δpgb hvr::pAP01; pAP01 recombinant host for over-expression of Hvr-BGC | This study |
| MMG2012 | Δpgb Δphn Δhvr; Markerless deletion in MMG1988 using allele exchange plasmid pAP04 | This study |
| *Enterococcus faecalis* ATCC 19433 | | ATCC #19433 |
| *Staphylococcus aureus* ATCC 29213 | | ATCC #29213 |
| *Klebsiella pneumoniae* ATCC 27736 | | ATCC #27736 |
| *Acinetobacter baumannii* ATCC 19606 | | ATCC #19606 |
| *Pseudomonas aeruginosa* PAO1 | | Hergenrother Lab (UIUC) |
| *Escherichia coli* ATCC 25922 | | ATCC #25922 |
| *Salmonella enterica* LT2 | | ATCC #700720 |
| *Candida albicans* SN250 | | Burke Lab (UIUC) |
| *Aspergillus fumigatus* 1163 | | Burke Lab (UIUC) |
| *Saccharomyces cerevisiae* X2180-1A | | Imlay Lab (UIUC) |

[a]Cell 1978, 15(4): 1199-208

[b]Proc Natl Acad Sci U S A 1990, 87(12):4645-4649

[c]Nat Chem Biol 2007, 3: 480-485

[d]Chem Biol 2008, 15(8):765-770

Bioinformatic analyses of phosphonate metabolism in *P. ananatis* strains. *P. ananatis* genomes were downloaded from NCBI database and Hidden Markov Model (HMM) search was performed using HMMER version 3.2.1. The HMMs used for analysis were phosphoenolpyruvate phosphomutase (pepM, TIGR02320), phosphonoacetaldehyde hydrolase (phnX, TIGRO1422), phosphonoacetate hydrolase (phnA, TIGR02335), 2-AEP transaminase (phnW, TIGRO2326 and TIGRO3301), phosphonopyruvate hydrolase (palA, TIGR02321), phosphonoacetaldehyde dehydrogenase (phnY, TIGR03250), HD-phosphohydrolase (phnZ, TIGR00277 and PF01966), C—P lyase (phnJ, PF06007). Genomes with an HMM match were considered to have the associated metabolism. Genomes containing pepM were screened for the presence of the hvr locus by mapping them to the *P. ananatis* LMG 5342 gene cluster using Geneious Prime® 2020.2.1 software. For pepM genes that did not correspond to the hvr operon, gene cluster boundaries around the pepM were deduced based on the presence of either flanking integrative and conjugative elements or genes that appeared to be in an operon together with pepM. BLASTP was used to assign functions to genes in the gene cluster based on homology to proteins of known function.

Genome sequencing of *Pantoea* NRRL strains. The genomes of strains *P. ananatis* NRRL B-14773 and *P. ananatis* B-133 (since renamed as *P. stewartii* based on NCBI average nucleotide identity analyses) were sequenced for use in this study. High molecular weight genomic DNA was purified using Qiagen® DNeasy UltraClean Microbial Kit. Purified genomic DNA was prepared using Shotgun Flex DNA library prep and sequenced using Illumina MiSeq v2 platform (250 nt paired end reads) by the Roy J. Carver Biotechnology Sequencing Center, UhUC. Genome reads were trimmed using BBDuk software, assembled using SPAdes 3.14.1 and annotated using RAST Server. Assembled reads were submitted to the NCBI Whole Genome Shotgun (WGS) database. This WGS project has been deposited at DDBJ/ENA/GenBank under the accessions JACETZ000000000 (for P. stewertii NRRL B-133 and JACEUA000000000 (for *P. ananatis* NRRL B-14773). Genomes were analyzed for phosphonate metabolism as described above.

TABLE 4

Plasmids used in this study.

| Plasmids | Features/Construction/Use | Source/ Reference |
|---|---|---|
| pAE4 | oriT, $Apr^R$, λattP, ΦC31 int, ΦC31attP | d |
| pAH56 | uidAF, λattP, oriR6K, $Kan^R$, $lacI^q$, Ptac | e |
| PAP01 | hvrA, oriT, λattP, oriR6K, $Kan^R$, $lacI^q$, Ptac; Gibson assembly with pAP10 PCR product (PCR primers pAP10-rev/for) and *P. ananatis* LMG 5342 pepM gene (PCR primers Hvr-PepM-rev/for); used for integrating Ptac promotor upstream of Hvr-BGC | This study |
| PAP02 | sacB, $Amp^R$, oriR6K, $T7_p$, $Kan^R$, $lac_p$; Gibson assembly with pHC001A-SacI/XhoI-digested plasmid and 1 kb upstream (PCR primers Pgb-left-hArm_R/F) and downstream (PCR primers Pgb-right-hArm_R/F) homology fragments to Pgb gene cluster; used to make markerless deletion of Pgb gene cluster | This study |
| PAP04 | sacB, $Amp^R$, oriR6K, $T7_p$, $Kan^R$, $lac_p$; Gibson assembly with pHC001A-SacI/XhoI-digested plasmid and 1kb upstream (PCR primers Hvr-left-hArm_R/F) and downstream (PCR primers Hvr-right-hArm_R/F) homology fragments to Hvr gene cluster; used to make markerless deletion of Hvr gene cluster | This study |
| PAP05 | sacB, $Amp^R$, oriR6K, $T7_p$, $Kan^R$, $lac_p$; Gibson assembly with pHC001A-SacI/XhoI-digested plasmid and 1 kb upstream (PCR primers Phn-left-hArm_R/F) and downstream (PCR primers Phn-right-hArm_R/F) homology fragments to Phn gene cluster; used to make markerless deletion of Phn gene cluster | This study |
| PAP10 | uidAF, oriT, λattP, oriR6K, $Kan^R$, $lacI^q$, Ptac; Gibson assembly with pAH56-SalI-digested plasmid and the oriT PCR-fragment from pAE4 plasmid (PCR primers pAH56-pAE4oriT-rev/for); used as parent plasmid for construction of pAP01 | This study |
| pHC001A | sacB, $Amp^R$, oriR6K, $T7_p$, $Kan^R$, $lac_p$; used as parent plasmid for allele exchange plasmid construction | f |

[d]Chem Biol 2008, 15(8):765-70

[e]J Bacteriol 2001, 183(21):6384-93

[f]J Biol Chem 2011, 286(25):22283-90

Genetic methods for making unmarked deletion mutations. Approximately 1 kb of DNA upstream and downstream of the region to be deleted were cloned into pHC001A (see Table 4 for complete list of plasmid constructs). The resulting plasmids were introduced into electrocompetent *E. coli* DH5α/λpir and maintained in LB media+50 μg/mL kanamycin (LB-Kan). Plasmid constructs were moved into the conjugation strain WM6026 via electroporation-mediated transformation, then transferred to *P. ananatis* recipients via conjugation. Conjugations were performed by streaking isolated colonies of donor and recipient together in small (2 cm×2 cm) patches on agar-solidified LB medium containing 60 μM diaminopimelic acid (DAP) to allow growth of WM6026-derived donor strains, which are DAP auxotrophs. After overnight incubation at 30° C., the patches were picked and restreaked on LB-Kan without added DAP to select for *P. ananatis* recombinants that carry the deletion plasmids, which cannot replicate autonomously in *P. ananatis*, inserted into the target locus by homologous recombination. Exconjugants were purified by streaking for isolated colonies on LB-Kan at 30° C., then by streaking on LB without antibiotics to allow for segregation of the integrated plasmid. Recombinants that had lost the integrated plasmid were then isolated by streaking on LB media without NaCl containing 5% sucrose, which selects against the sacB gene encoded on the integrated deletion plasmid. Loss of the integrated plasmid was verified by showing that the purified recombinants were kanamycin sensitive. Finally, recombinants carrying the desired deletion were identified by PCR-based screening using primers (Table 5) described in Polidore et al., mBio. 2021 Jan-Feb; 12(1): e03402-20, which reference and supporting information is incorporated herein by reference in its entirety.

TABLE 5

Primers used in this study.

| Primer Name | Sequence (5' -> 3') | Use |
|---|---|---|
| Pgb-int-rev | CTTGCTGCAGGTAGGGGT (SEQ ID NO: 26) | PCR-based assay for detection of phosphocholine cytidylyltransferase |
| Pgb-int-for | TCTATCCACGGCAAACCACT (SEQ ID NO: 27) | gene (n.t. 2,701,405 -> 2,700,635)[a] within Pgb gene cluster |
| dPgb-rev | TGATGGCCTGCAAGACGG (SEQ ID NO: 28) | PCR-based assay for detection of |
| dPgb-for | TCTATCCACGGCAAACCACT (SEQ ID NO: 29) | the deletion of Pgb gene cluster |
| Phn-int-rev | CAGCGCAACAGACTGGGA (SEQ ID NO: 30) | PCR-based assay for detection of alpha-D-ribose 1-methylphosphonate 5-triphosphate |
| Phn-int-for | CCCATTCCGCCATGAGCA (SEQ ID NO: 31) | diphosphatase gene (phnM; n.t. 1,796,249 -> 1,797,385)[a] within Phn gene cluster |
| dPhn-rev | ACGGTAAGATTGGGCGCC (SEQ ID NO: 32) | PCR-based assay for detection of |
| dPhn-for | GGCCAACGATCGCGGATA (SEQ ID NO: 33) | the deletion of Phn gene cluster |
| PANA_3283 812-833R | GCTGCTATCCCCGAGATAATGA (SEQ ID NO: 34) | PCR-based assay for detection of MFS transporter gene (hvrl; 809,348 -> 810,584)[a] within Hvr |
| PANA_3283 64-85F | GCTGAAGGGATTCAGACGGTTA (SEQ ID NO: 35) | gene cluster; primer sequences taken from the reference below8 |
| dHvr-rev | TTACCGCCACCTTGCTGG (SEQ ID NO: 36) | PCR-based assay for detection of |
| dHvr-for | TTTCGCCCGTTCCCCTTC (SEQ ID NO: 37) | the deletion of Hvr gene cluster |
| PANA-Hvr-pepM-rev | GCCGTCCTGCCATATCTCAA (SEQ ID NO: 38) | |
| PANA-Hvr-pepM-for | TAACGGACTCAGCATCTCGC (SEQ ID NO: 39) | Detection of Hvr marker gene; Phosphoenolypyruvate mutase gene (hvrA; n.t. 801,910 -> 802,764)[a] |
| pHC001A-MCS-rev | CCCGACCCGAAACACCAT (SEQ ID NO: 40) | Sequencing primer |
| pHC001A-MCS-for | TGTTCGCCAGGCTCAAGG (SEQ ID NO: 41) | Sequencing primer |
| Phn-left-hArm_R | ACTAAAGGGAACAAAAGCTGGA GCTCCGCCAAAAATCAGCTGTG (SEQ ID NO: 42) | For pAP05 construction |
| Phn-left-hArm_F | GGATTTAATTGTGAAAGACTCTC CGCTCGTG (SEQ ID NO: 43) | |
| Phn-right-hArm_R | GCGGAGAGTCTTTCACAATTAA ATCCTCACATCAGTAGAGG (SEQ ID NO: 44) | |
| Phn-right-hArm_F | CTGGATGATCCTCCAGCGGGGC CCCCCCTCGAGTTCATGGCGCGG CTTTCG (SEQ ID NO: 45) | |
| Pgb-left-hArm_R | ATTTTATTTATTTAAACGTTAAA CAAGAAATTCATC (SEQ ID NO: 46) | For pAP02 construction |
| Pgb-left-hArm_F | TCCTCCAGCGGGGCCCCCCCTCG AGTTGAAGCGGCTAACTTCC (SEQ ID NO: 47) | |

TABLE 5-continued

Primers used in this study.

| Primer Name | Sequence (5' -> 3') | Use |
|---|---|---|
| Pgb-right-hArm_R | AGGGAACAAAAGCTGGAGCTCT TGTTTCATCCATCATACC (SEQ ID NO: 48) | |
| Pgb-right-hArm_F | TTAACGTTTAAATAAATAAAATT GCTTGTCTCATG (SEQ ID NO: 49) | |
| Hvr-left-hArm_R | CTGACGGATTTTACAAACGCAA AAACCCCCGCC (SEQ ID NO:50) | For pAP04 construction |
| Hvr-left-hArm_F | CTGGATGATCCTCCAGCGGGGC CCCCCCTCGAGTAATCGCCGCCC ACGCCG (SEQ ID NO: 51) | |
| Hvr-right-hArm_R | ACTAAAGGGAACAAAAGCTGGA GCTCCCATCATTACGTTTATGCC (SEQ ID NO: 52) | |
| Hvr-right-hArm F | GTTTTTGCGTTTGTAAAATCCGT CAGGTGCAC (SEQ ID NO: 53) | |
| SEQ-PAP-rev | ACTATGAGCACGTCGGCG (SEQ ID NO: 54) | sequencing primer |
| SEQ-pAP-for | CGCACTCCCGTTCTGGAT (SEQ ID NO: 55) | sequencing primer |
| aph-rev | CAGGATGAGGATCGTTTCGC (SEQ ID NO: 56) | $Kan^R$ marker gene detection |
| aph-for | TCGAACCCCAGAGTCCCG (SEQ ID NO: 57) | $Kan^R$ marker gene detection |
| PAP10-rev | ATGTATATCTCCTTCTTACAAGC TTGGC (SEQ ID NO: 58) | For pAP01 construction |
| PAP10-for | TCTAGATGCACTCCACCGCTGAT GACATCAG (SEQ ID NO: 59) | |
| Hvr-PepM-rev | ATGTCATCAGCGGTGGAGTGCA TCTAGATTAAGGAATCAGTGAA ATAATTTC (SEQ ID NO: 60) | |
| Hvr-PepM-for | AAGCTTGTAAGAAGGAGATATA CATATGATCAAAAAACTTATTGC AG (SEQ ID NO: 61) | |
| pAH56-pAE4oriT-rev | CATGAGAATTAATTCCGGGGAT CCGTCGACACTACCATCGGGGG CCATC (SEQ ID NO: 62) | For pAP10 construction |
| pAH56-pAE4oriT-for | CTACAGCCTCGGGAATTGCTGC AGGTCGACTCTAGATGCACTCC ACCGC (SEQ ID NO: 63) | |

[g]Mol Plant Microbe Interact 2018, 31(12):1291-1300

Introduction of IPTG inducible Ptac system. Plasmid construct, pAP01, was introduced into WM6026 by electroporation with selection on LB+50 μg/mL kanamycin (LB-Kan). The plasmid was then transferred to *P. ananatis* MMG1988 as described in the preceding section. Recombinants that carry an integrated copy of pAP01 inserted into the hvrA gene were selected on LB-Kan. The resulting colonies were screened for the plasmid integration using primers for aph and $lal^q$ as well as the Hvr-marker gene hvrI. The resulting strain, *P. ananatis* MMG2010, was maintained in LB-Kan to prevent loss of the integrated plasmid.

NMR and MS. The $^1$H-NMR, $^{13}$C-NMR and $^{31}$P-NMR spectra were recorded on an Agilent DD2 600 MHz spectrometer (600 MHz for $^1$H, 150 MHz for $^{13}$C and 243 MHz for $^{31}$P). Samples were prepared in 20-100% $D_2O$ as the locking solvent. Quantitative $^{31}$P NMR was performed using an internal standard of 0.5 mM dimethylphosphinate with addition of 0.9 mM EDTA, and acquisition was performed using 5× the T1 measurement (relaxation time) for the sample. Phosphonate peak integrals were calculated using MestReNova v11.0.1 software and normalized to the internal standard. Concentrations were calculated based on the ratio of the normalized phosphonate peak integrals to the known concentration of internal standard. Mass spectrometry was performed by the School of Chemical Sciences Mass Spectrometry Laboratory using a Waters@ Q-TOF Ultima ESI in which 10 μL of sample was injected at a concentration of 10 μg/mL in methanol.

IPTG-induced expression of the hvr operon in *P. ananatis* MMG2010. A frozen glycerol stock of *P. ananatis* MMG2010 was revived on LB+50 μg/mL kanamycin and incubated at 30° C. for 24 hours. A single colony was then transferred to 5 mL of phosphonate induction media (PIM). The culture was incubated at 30° C. for 48 hours, then 0.5 mL of culture was transferred to 50 mL PIM and incubated at 30° C. for 24 hours. The next day, 8 mL of culture was transferred to each of four flasks containing 800 mL PIM medium plus 1 mM IPTG. These 800 mL cultures were incubated shaking at 175 rpm at 30° C. for 72 hours. After growth, cultures were centrifuged at 8000 rpm for 20 minutes to remove cells and debris and the supernatant was concentrated by freeze-drying. Quantitative $^{31}$P NMR analysis was performed on the concentrated supernatant aliquot to determine phosphonate production levels after adding dimethylphosphinate (0.5 mM final) as an internal standard.

Purification of pantaphos and compound 2. A 3.2 L culture of *P. ananatis* MMG2010 was grown in PIM medium with 1 mM IPTG as described in the preceding section. After centrifugation to remove cells, the spent medium was freeze-dried and the dried material resuspended in 300 mL $H_2O$. 1200 mL of 100% cold methanol was then added for a final concentration of 75% methanol and incubated at −20° C. overnight. Precipitated material was removed and saved using vacuum filtration with a Whatman® grade 42 ashless filter and the methanol-soluble fraction dried to completion using initial rotary evaporation followed by freeze-drying. The 48.0 g of dried material obtained by this process (Sample A) was saved for further purification. The precipitated material saved from the above methanol extraction was subject to a secondary 75% methanol extraction as described. Then the methanol-soluble fraction was dried to completion using initial rotary evaporation followed by freeze-drying. The 1.60 g of dried material obtained by this process (Sample B) was saved for further purification. Sample A was subject to $Fe^{3+}$-IMAC purification as follows. Ten grams of Chelex resin (sodium form) was converted to the $H^+$ form by incubation in 1 M HCl for 30 minutes followed by wash with 5 column volumes (CV) of water. Next, the resin was charged with $Fe^{+3}$ by resuspension in 100 mL of 300 mM $FeCl_3 \cdot 6H_2O$ for 1 hour at 4° C. followed by washing with 100 mL of 0.1% acetic acid and incubation in 100 mL of 0.1% acetic acid overnight at 4° C. Sample A was acidified using concentrated acetic acid to pH 3 and incubated with the Fe-IMAC resin at 4° C. for 2 hours. The solution was separated from the resin using a gravity column and the flow-through containing unbound phosphonic acids was saved (Sample-Flowthrough). Bound phosphonic acids were eluted from the Fe-IMAC resin using a gradient of 100 mL $NH_4HCO_3$ (1, 5, 25, 50, 100, 250, 500, and 1000 mM) and fractions collected and neutralized to neutral pH using acetic acid. The eight fractions were concentrated using initial rotary evaporation followed by freeze-drying. Sample-Flowthrough, containing any unbound phosphonic acids, obtained from above was combined with Sample B and subjected to a second round of Fe-IMAC purification as described above. Fractions were concentrated using initial rotary evaporation followed by freeze-drying. From each of the Fe-IMAC purifications, the fractions were combined in 2-3 mL $H_2O$ as follows: the 500-1000 mM $NH_4HCO_3$ fractions (Sample 1), the 1-5 mM $NH_4HCO_3$ fractions (Sample-2), and the 25-50-100-250 mM $NH_4HCO_3$ fractions (Sample 3). Samples 1, 2, and 3 were separately concentrated and dried via freeze-drying to obtain 45.1 mg, 30.6 mg, and 6.9 mg of dried material respectively. Quantitative phosphorus NMR, based on a 0.5 mM dimethylphosphinate standard reference, and purity assessment using proton NMR was performed for each sample. Samples 1 and 3 contained 0.551 mmol and 0.215 mmol phosphonate respectively. However, Sample 2 was found to contain only 0.0165 mmol phosphonate and included residual phosphates that are not present in Samples 1 and 3, therefore, was not used for further purification steps.

Sample 1 was subjected to further purification using a Teledyne ISCO CombiFlash RF+UV-Vis system using a RediSep SAX anion exchange resin. Sample 1 was lyophilized, then reconstituted in 75% methanol. Insoluble material was removed by centrifugation, resuspended in 1 mL of 100% $D_2O$ and examined by $^{31}P$ NMR. Samples containing residual phosphonates were subjected to additional cycles of drying and 75% methanol until all phosphonate compounds were solubilized. The methanol-soluble fractions were then pooled and subjected to CombiFlash purification. To do this, 5.7 g RediSep SAX column was equilibrated with 20 column volumes (CV) of 5% $NH_4OH$ in $H_2O$, followed by 20 CV of $H_2O$, then 20 CV of 90% methanol. A 1 mL sample from the methanol-soluble fractions was loaded onto the column via direct injection followed by: 3.3 min 100% A (90% methanol), linear gradient to 100% B (5% $NH_4OH$ in $H_2O$) over 15 min then 100% B for 6 min followed 5 by 3.5 min 100% A at 18 mL/min flow rate. Fractions were monitored using UV 250 nm and 210 nm, fractions showing absorbance at either wavelength were combined and analyzed by $^{31}P$ NMR. Fractions containing the $\delta_P$ 18 and 15 ppm phosphorus chemical shifts were saved and dried via rotary evaporation followed by freeze-drying.

Sample 3 and the Combiflash purified Sample 1 were then subject to HPLC purification separately. Dried samples were reconstituted in 1 mL $H_2O$, then 50-100 μL of sample was diluted in solvent B (90% acetonitrile+10 mM $NH_4HCO_3$ at pH 9.20) for a final concentration of 75% solvent B. Samples were then filtered through a 0.45 m filter and purified using Atlantis HILIC Silica column (10×250 $mm^2$, 5 μm particle size) using gradient elution. Chromatography was performed at flow rate of 4 mL/min using $H_2O$+10 mM $NH_4HCO_3$ at pH 8.50 (solvent A) and 90% acetonitrile+10 mM $NH_4CO_3$ at pH 9.20 (solvent B). The gradient performed was as follows: 8 min at 90% solvent B, followed by a linear gradient to 70% solvent B over 20 min, then 50% solvent B over 1 min, hold at 50% solvent B over 8 min, then back to 90% solvent B over 1 min, followed by hold at 90% solvent B for 8 min. Fractions were collected and monitored for UV absorption at 210 and 250 nm. Fractions that absorbed at these wavelengths were combined and dried via rotary evaporation and analyzed using phosphorus NMR. Fractions were obtained that contained a pure phosphonate compound with a $\delta_P$ 15 ppm chemical shift (corresponding to pantaphos), and fractions were obtained containing a purified phosphonate compound with a $\delta_P$ 18 ppm chemical shift (corresponding to compound 2). Additional fractions were obtained that contained a mixture of pantaphos and compound 2. Purified compounds were dried and saved at 4° C. for MS and NMR structural analyses as described above.

Onion bioactivity assays. Yellow onions purchased form the local market were surface sterilized in a laminar flow biosafety hood as follows. First, the outermost layers with any damage or browning were removed and discarded, followed by soaking for 10 minutes in 10% bleach. The onions were then rinsed three times with sterile $dH_2O$, followed by soaking in 70% EtOH for an additional 10 minutes, then rinsed four times with sterile $dH_2O$. The onions were left in a biosafety laminar flow hood until water and ethanol were completely evaporated. For testing virulence of microbial strains, the onions were inoculated by stabbing with a previously sterilized wooden toothpick dipped into a bacterial cell suspension (1×103 CFU/mL in 1×PBS buffer). Chemical complementation studies were performed by addition of 100 μL of filter-sterilized sample into the hole created by the toothpick during inoculation. For testing bioactivity of crude and purified chemical samples in the absence of bacteria, holes were punched in sterilized onions using sterile toothpicks followed by addition of 100 μL of a filter-sterilized sample. Following inoculation and/or treatment with filter-sterilized compounds, the onions were placed in zip-lock plastic bags and incubated at 30° C. in the dark for the indicated number of days. Following incubation, the onions were sectioned across the site of inoculation/sample application to allow visual inspection of the center rot phenotype.

Mustard seedling and *Arabidopsis thaliana* Col-0 bioactivity testing. All seed preparation was performed in a laminar flow biosafety hood. Burpee® tendergreen mustard seeds were cleaned as follows: 10% bleach for 1 min, 3× rinse with sterile $dH_2O$, 70% ethanol for 1 min, followed by 5× rinse with sterile $dH_2O$. Washed seeds were transferred to a sterilized paper towel and placed inside a sterile container. Then, 5 mL of sterile tap water was added to the paper towel and the container was incubated in the dark for 48 hours to allow the seeds to germinate. Germinated seedlings were transferred to 24-well cell culture plates containing 1 mL of Murashige and Skoog agar (1% agar) per well. *Arabidopsis thaliana* Col-0 sterile seeds (Stock Number: CS1092) were purchased from the *Arabidopsis* Biological Resource Center (ABRC) and incubated at 4° C. for 2-3 days. Cold incubated seeds were then transferred to 24-well cell culture plates containing 1 mL of Murashige and Skoog agar (1% agar) per well and incubated in the dark until seed germination observed. To both mustard and *Arabidopsis* germinated seedlings, 20 µl of an appropriate dilution of the filter-sterilized compounds being tested were then added to each well to achieve the desired concentration. For negative controls, 20 µL of sterile $dH_2O$ was spotted onto the agar. The 24-well plates were incubated in a 60% humidity-controlled growth room with a 16 hr. light cycle at 23° C. for one week. Following incubation, plants were extracted from the growth agar by gentle pulling, which resulted in essentially agar free plants. Root length was measured immediately; dry weight was determined after drying for 24 hrs. at 150° C. Statistical analysis was performed among each condition to determine significance using the standard Welch's t-test analysis from GraphPad Prism 8.4.1 software.

Cell culture cytotoxicity screening. The compounds were evaluated for their ability to kill cancer cell lines in culture, using HOS (osteosarcoma); ES-2 (ovarian cancer); HCT 116 (colon cancer); A549 (lung carcinoma); and A172 (glioma) cells. Human skin fibroblast cells (HFF-1) were also assessed. Cells were seeded (3000 cells $well^{-1}$ for ES-2, HCT 116, A549 and A172; 4000 cells $well^{-1}$ for HFF-1 and 2500 cells $well^{-1}$ for HOS) in a 96-well plate and allowed to attach overnight. Cells were treated with pantaphos in water. The concentrations of the tested compounds were 5 nM to 100 µM (1% water final; 100 µl $well^{-1}$). Raptinal (50 µM) was used as a dead control. On each plate, five technical replicates per compound were performed. 72 hrs. post-treatment, cell viability was assessed using the Alamar Blue method (http://www.bio-rad-antibodies.com/measuring-cytotoxicity-proliferation-spectrophotometry-fluorescence-alamarBlue.html). Alamar Blue solution (10 µl of 440 µM resazurin in sterile 1×PBS) was added to each well, and the plate was incubated for 3-4 hrs. Conversion of Alamar Blue was measured with a plate reader (SpectraMax M3; Molecular Devices) by fluorescence (excitation wavelength: 555 nm; emission wavelength: 585 nm; cutoff 570 nm; auto-gain). Percentage death was determined by normalizing to water-treated cells and Raptinal-treated cells. For $IC_{50}$ determination, the data were plotted as compound concentration versus dead cell percentage and fitted to a logistic-dose-response curve using OriginPro 2019 (OriginLab). The data were generated in triplicate, and $IC_{50}$ values are reported as the average of three separate experiments along with SEM values.

Antibacterial bioassays. Susceptibility testing for the ESKAPE pathogens and *Salmonella enterica* LT2 was performed using a Kirby-Bauer method as outlined by the Clinical and Laboratory Standards Institute (CLSI). For rich media bioassays, Mueller Hinton Broth 2 (MH-2, Sigma-Aldrich, 90922) was used for all strains except 1% BHI was supplemented for *Enterococcus faecalis* ATCC 19433. For minimal media bioassays, glucose-MOPS minimal medium was used. Briefly, overnight bacterial cultures were sub-cultured and inoculated into 5 mL top agar (0.7% agar) for final concentration of $5\times10^5$ CFU/mL. Then, 20 µL of a compound 2-fold dilution series (200, 100, 50, 25, 12.5, 6.25 µM in water) was spotted on 6 mm diameter blank paper discs (BD BBL™ 231039). Control discs received 20 µL of 50 mg/mL kanamycin. Plates were incubated at 35° C. for 20-24 hours. Minimum Inhibitory Concentration (MIC) was recorded as the lowest concentration of compound that resulted in a clear zone of inhibition around the disc. Sensitivity of the IPTG-inducible phosphonate uptake strain WM6242 to pantaphos was tested using a disk diffusion assay. Plates containing growth medium were overlayed with 5 mL of top agar (0.7% agar) inoculated with 100 µL ($OD_{600}$=0.8) of the phosphonate-specific *E. coli* indicator strain (WM6242) with or without addition of 1 mM IPTG. WM6242 is engineered with an IPTG-inducible, non-specific phosphonate uptake system (phnCDE). After the seeded overlay solidified, 6 mm paper disks were spotted with 10 µL of a dilution series (200, 100, 50, 25, 12.5, 6.25 µM in water) of pantaphos and applied to the plates that were then incubated at 37° C. for 24 hrs. Phosphonate-specific activity was queried by comparing sensitivity to that of 200 µM kanamycin and 200 µM fosfomycin. Minimum Inhibitory Concentration (MIC) was recorded as the lowest concentration of compound that resulted in a clear zone of inhibition around the disc Fungicidal bioassays. Methods for fungicide testing were adopted from the CLSI publication M27, Reference for Broth Dilution Antifungal. Briefly, a −80° C. fungal stock was streaked on the appropriate media as indicated previously and incubated at 35° C. for 24-48 hrs. For *Candida* and *Saccharomyces*, a single colony was picked and resuspended in 1 mL 1×PBS and then diluted in growth medium to a final concentration of $1\times10^4$ CFU/mL. For *Aspergillus*, spores from the hyphal growth on the growth medium plate were resuspended by swirling 1 mL of 90% saline+0.1% Tween-20 onto the lawn. This 1 mL yeast suspension was then diluted in growth medium to $1\times10^4$ CFU/mL final concentration. Then, 2 µL of compound was added to 198 µL of the yeast suspension in a sterile 96-well round bottom plate. For positive controls, 2 µL of a stock solution of amphotericin B was added to a final concertation of 2 or 10 µM as specified. 200 µL of un-treated yeast suspension and an uninoculated media were included as controls. The plate was incubated at 35° C. for 24-48 hrs depending on growth medium without shaking. Minimum Inhibitory Concentration (MIC) was determined visually by finding the concentration of compound at which there was no visual difference between that concentration and the uninoculated media control.

Identification and analysis of homologous Hvr biosynthetic gene clusters in bacteria. NCBI tblastn was used to identify bacterial genomes that contain Hvr-like gene clusters. The query was constructed by concatenating the gene translations of hvrA-L. Tblastn was used against the RefSeq Genomes and the RefSeq Representative Genomes databases using the 'Organism' parameter of 'Bacteria [taxid:2]', and the non-redundant nucleotide database. The results were filtered by 45% query coverage, which resulted in 185 unique bacterial strains. The GenBank files for each strain was downloaded and homologous Hvr gene clusters were determined using MultiGeneBlast. Homologous Hvr biosynthetic gene clusters were organized by type based on gene arrangement within the cluster and presence of additional gene functions.

Example 2. Structure Elucidation of Phosphonate Compounds (1)

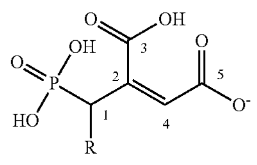

-continued

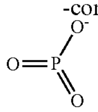

mass = 78.9583
formula = $O_3P^-$
Δppm = -2.61

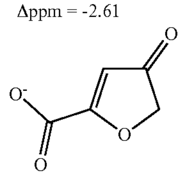

mass = 127.0031
formula = $C_5H_3O_4^-$
Δppm = -0.26

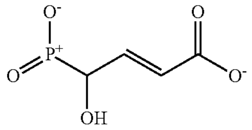

mass = 162.9798
formula = $C_4H_4O_5P^-$
Δppm = 1.01

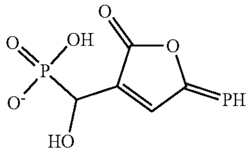

mass = 206.9698
formula = $C_5H_4O_1P^-$
Δppm = 1.62
mass = 207.97331
formula = $C_4{}^{13}C_1H_4O_7P^-$
Δppm = 1.35

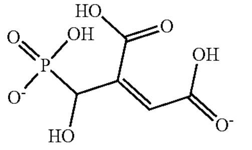

mass = 224.9805
formula = $C_5H_6O_8P^-$
Δppm = 2.09
mass = 225.9834
formula = $C_4{}^{13}C_1H_6O_8P^-$
Δppm = 0.07

Structure elucidation of compound 1: NMR spectral data are summarized in the main text (Table 1) and below; High-resolution mass-spectral data for compound 1 (purified pantaphos) are presented here. The designated mass fragments with assigned chemical structures are shown above. MS chemical formulas and mass error was calculated using ChemCalc workspace. Compound 1 was isolated as a white, amorphous solid. Its molecular formula was deduced by negative mode HRMS (calcd. for $C_5H_6O_8P^{-1}$: 224.98058, observed m/z 224.9805 [Δppm 2.09]).

Compound 1 was dissolved in 100% D20 for NMR experiments. The $^1H$-NMR spectrum for compound 1 revealed two signals at $\delta_H$ 4.31 and 5.91 ppm that appeared as doublets with coupling constants J of 15.3 Hz and 6.00 Hz, respectively. The large coupling constant J of 15.3 Hz is typical for protons bound to the adjacent carbon to a phosphorus atom in phosphonic acids. These protons were also correlated to the phosphorus atom of the compound at $\delta_P$ 15.40 ppm in the $^1H$-$^{31}P$ HMBC analysis indicating close proximity (within 3-bond distance) to P. In addition, the downfield signal at $\delta_H$ 5.91 indicates a vinyl-carbon or alkene structure, which indicates that this signal corresponds to a single proton. The $^{13}C$-NMR spectrum revealed signals at $\delta_C$ 71.00 (d, J=144.00 Hz), 142.98 (s), 174.62 (s), 126.50 (d, J=9.05 Hz), and 175.20 (s) ppm indicating compound 1 contains five carbons. The large coupling constant of the signal at $\delta_C$ 71.00 ppm suggests this carbon is bonded to the phosphorus atom as this splitting pattern has been observed for C—P bonding in other phosphonic acid compounds. Therefore, this signal at $\delta_C$ 71.00 ppm is assigned as carbon position 1. None of the other carbon signals showed a typical C—P splitting pattern, therefore, the signals corresponding to these carbons must reflect carbon positions opposite the phosphonate moiety and adjacent to or nearby carbon 1.

Proton-carbon HSQC and HMBC experiments revealed the coupling of proton at $\delta_H$4.31 ppm to the carbon at position 1 ($\delta_C$ 71.00 ppm) and was observed to correlate to the other carbons at $\delta_C$ 142.98, 174.62, and 175.20 ppm supporting the assignment of these carbons at positions adjacent to or nearby carbon 1. The carbon signal at $\delta_C$ 142.98 ppm has no splitting pattern and aligns with the chemical shifts predicted for vinyl compounds bound to an adjacent carboxylic acid and methyl group suggesting carbon position 2 assignment. The similar carbon signals at $\delta_C$ 174.62 and 175.20 ppm have no splitting pattern and align with the chemical shifts predicted for carboxylic acids suggesting assignment to carbon positions 3 or 5. However, the splitting of the carbon signal at $\delta_C$ 126.50 ppm (d, J=9.05 Hz) indicates the presence of an adjacent proton as the $^{13}C$-NMR analysis was not performed with decoupling of $^1H$. This is supported by the HSQC between this carbon and the proton at $\delta_H$5.91 ppm. These data fully support the assignment of the carbon at $\delta_C$ 126.50 ppm to carbon position 4. Based on the proton-carbon HMBC between the protons at $\delta_H$ 4.31 and 5.91 ppm and the carbons at $\delta_C$ 142.98, 174.62, and 175.20 ppm, we were able to confirm assignment of carbons at $\delta_C$ 142.98, 174.62, and 175.20 ppm to positions 2, 3, and 5, respectively. Finally, after $^1H$-$^1H$ correlation analyses, it was determined that the protons at $\delta_H$ 4.31 and 5.91 ppm are arranged in a cis carbon-carbon double bond configuration. Based on the agreements between the MS data and these NMR assignments the compound structure is identified as (E)-2-(hydroxy(phosphono)methyl)-4-oxopent-2-enoate.

(2)

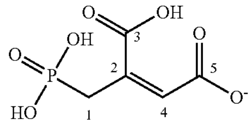

Structure elucidation of compound 2: NMR spectral data are summarized in the main text (Table 1); NMR spectra and high-resolution mass-spectral data for compound 2 are found at the end of this paragraph. MS chemical formulas and mass error was calculated using ChemCalc workspace. Compound 2 was isolated as a white, amorphous solid. Its molecular formula was deduced by negative mode HRMS (calcd. for $C_5H_6O_7P^{-1}$: 208.98566, observed m/z 208.9851 [Δppm-0.07]). Fractions containing pure compound 2 were dissolved in 100% $D_2O$ and subjected to proton and phosphorus NMR analyses. For carbon NMR experiments, a sample containing trace amounts of compound 1 were used as there was not enough concentrated pure compound 2 to perform carbon-13 analyses. The $^1$H-NMR spectrum for compound 2 revealed two signals at δ 5.71 (d, J=6.00 Hz) and 2.43 ppm (d, J=18.0 Hz). The large coupling constant J of 18.0 Hz is typical for protons bound to the adjacent carbon to a phosphorus atom in phosphonic acids. These protons were also correlated to the phosphorus atom of the compound at $\delta_P$ 18.46 ppm in the $^1$H-$^{31}$P HMBC analysis indicating close proximity (within 3-bond distance) to P. In addition, the downfield signal at $\delta_H$ 5.71 indicates a vinyl-carbon or alkene structure, which indicates that this signal corresponds to a single proton. $^{13}$C-NMR analysis revealed signals at $\delta_C$ 34.05 (d, J=123.0 Hz), 6 126.10 (d, J=10.60 Hz), 6 140.36 (s), 6 174.68 (s), and 6 177.02 (s) ppm associated with compound 2 indicating a five-carbon molecule. The large coupling constant of the carbon signal at $\delta_C$ 34.05 ppm suggests this carbon is bonded to the phosphorus atom as this splitting pattern has been observed for C—P bonding in other phosphonic acid compounds. Therefore, this signal at $\delta_C$ 34.05 ppm is assigned as carbon position 1. None of the other carbon signals showed a typical C—P splitting pattern, therefore, the signals corresponding to these carbons must reflect carbon positions opposite the phosphonate moiety and adjacent to or nearby carbon 1. Proton-carbon HSQC and HMBC experiments revealed the coupling of protons at $\delta_H$ 2.43 ppm to the carbon at position 1 ($\delta_C$ 34.05 ppm) and was observed to correlate to the other carbons at $\delta_C$ 140.36, 174.68, and 177.02 ppm supporting the assignment of these carbons at positions adjacent to or nearby carbon 1. The carbon signal at $\delta_C$ 140.36 ppm has no splitting pattern and aligns with the chemical shifts predicted for vinyl compounds bound to an adjacent carboxylic acid and methyl group suggesting carbon position 2 assignment. The similar carbon signals at $\delta_C$ 174.68 and 177.02 ppm have no splitting pattern and align with the chemical shifts predicted for carboxylic acids suggesting assignment to carbon positions 3 or 5. However, the splitting of the carbon signal at $\delta_C$ 126.10 ppm (d, J=10.60 Hz) indicates the presence of an adjacent proton as the $^{13}$C-NMR analysis was not performed with decoupling of $^1$H. This is supported by the HSQC between this carbon and the proton at $\delta_H$ 5.71 ppm. These data fully support the assignment of the carbon at $\delta_C$ 126.10 ppm to carbon position 4. Based on the proton-carbon HMBC between the protons at $\delta_H$ 2.43 and 5.71 ppm and the carbons at $\delta_C$ 140.36, 174.68, and 177.02 ppm, we were able to confirm assignment of carbons at $\delta_C$ 140.36, 174.68, and 177.02 ppm to positions 2, 3, and 5, respectively. Finally, after $^1$H-$^1$H correlation analyses, it was determined that the protons at $\delta_H$ 2.43 and 5.71 ppm are arranged in a cis carbon-carbon double bond configuration. Based on the agreements between the MS data and these NMR assignments the compound structure is identified as (E)-2-(phosphono)methyl)-4-oxopent-2-enoate.

Example 3. Multigram Preparation of Phosphonate Compounds

Process Flowchart for Multigram Scale Preparation of Phosphonate Products Disclosed Herein:

1. Phosphate induction with IPTG in 10 L bioreactor
2. Pellet cells and concentrate supernatant via freeze-drying
3. Methanol extraction of phosphonic acids
4. Purification from the methanol-soluble fraction using iron-IMAC
5. Further purification using flash chromatography and HILIC HPLC Detailed Steps of the Process:

Step 1: Frozen culture stock of phosphonate induction strain was streaked on LB medium and incubated ~18 hours at 30° C.;

Step 2: Single colony transferred into 5 mL of phosphonate-induction-medium (PIM minus IPTG; see published reference for formulation) and incubated for 48 hours at 30° C.;

Step 3: 1 mL of previous culture transferred to 200 mL PIM (minus IPTG) and incubated 48 hours at 30° C.;

Step 4: 100 mL of previous culture was transferred to 10 Liters PIM (with 1 mM IPTG) in New Brunswick BIOFLO 110 Fermenter/Bioreactor and incubated for 96 hours as follows:

a) Oxygenation (bubbling air at bottom of reactor) through a sterile air filter with gauge set to ~5 liters/min air flow rate;

b) Bioreactor equipped with heating jacket set to 30° C.;

c) *Pantoea ananatis* growth and phosphonate production indicated by yellow pigment development;

Step 5: Cells were pelleted (centrifugation 7500×g for 20 min) and culture supernatant (spent media) harvested and freeze dried until completely dehydrated;

Step 6: Phosphonic acids then extracted from the spent media using 75% cold methanol;

Step 7: The methanol-soluble fraction was separated either by filtration methods or centrifugation and the resulting solution was concentrated via rotary evaporation to remove methanol;

Step 8: methanol-soluble phosphonic acids were purified from the concentrated solution using 200 grams of Iron-IMAC resin affinity chromatography with a step-gradient of ammonium-bicarbonate up to 1 M. The resulting fractions were neutralized with acetic acid and concentrated using rotary evaporation;

Step 9: The resulting concentrated fractions containing phosphonic acids were further purified using a fast chromatography system with a strong-anion exchange column with a gradient of 5% ammonium-hydroxide. The resulting fractions that have an absorbance at 250 nm UV were pooled together and neutralized using acetic acid followed by concentration via rotary evaporation;

Step 10: The flash chromatography fractions can be further purified using HILIC HPLC with a gradient of acetonitrile+10 mM ammonium bicarbonate, pH 8.5 (solvent B) and water+10 mM ammonium bicarbonate, pH 8.5 (solvent A); fractions that absorb at 250 nm UV are collected and can be further separated using HILIC HPLC with a gradient of acetonitrile+10 mM ammonium acetate, pH 4 (solvent B) and water+10 mM ammonium acetate, pH 4 (solvent A). Finally, the remaining ammonium acetate is removed from pure compounds using HILIC HPLC with gradient of acetonitrile (solvent B) and water (solvent A).

Example 4. Phosphonate-Related Gene Clusters Associated with Various Pathogenic and Non-Pathogenic *P. ananatis* Strains

| Strain (sorted alphabetcally) | Isolation host/environment | Associated with plant Pathogenicity | Associated with onion disease | Hvr BGC* | Pgb BGC* | Putative phosphonate BGC-A* | Putative phosphonate BGC-B* | C-P lyase pathway** | Genome completion level | # pepM per strain |
|---|---|---|---|---|---|---|---|---|---|---|
| *P. ananatis* 97-1 | onion | Y | Y | + | – | – | – | + | complete | 1 |
| *P. ananatis* AJ13355 | soil | n/a | nt | – | – | + | – | + | complete | 1 |
| *P. ananatis* AMG521 | rice | N[g] | nt | – | – | – | – | + | scaffold | 0 |
| *P. ananatis* ARC272 | rice | n/a | nt | – | – | – | – | + | contig | 0 |
| *P. ananatis* ARC310 | rice | n/a | nt | – | – | – | – | + | contig | 0 |
| *P. ananatis* ARC311 | rice | n/a | nt | – | – | – | – | + | contig | 0 |
| *P. ananatis* (stewartii) B-133*** | fungus | N | N | – | – | – | – | + | scaffold | 0 |
| *P. ananatis* B-14773*** | fungus | N | N | – | – | – | – | + | scaffold | 0 |
| *P. ananatis* B1-9 | onion | N[g] | N | – | – | + | – | + | scaffold | 1 |
| *P. ananatis* B7 | maize | n/a | nt | + | – | – | – | + | contig | 1 |
| *P. ananatis* BAV 3296 | rain-isolated | n/a | nt | – | – | – | – | + | contig | 0 |
| ***P. ananatis* BD442** | maize | Y | N | – | – | – | + | + | contig | 1 |
| *P. ananatis* BRT175 | strawberry | n/a | nt | – | – | – | – | + | scaffold | 0 |
| *P. ananatis* CFH 7-1 | cotton | Y | nt | – | – | – | – | + | contig | 0 |
| *P. ananatis* DAR 76143 | rice | Y | nt | + | – | + | – | + | contig | 2 |
| *P. ananatis* DE0584 | soil | n/a | nt | – | – | – | – | + | scaffold | 0 |
| *P. ananatis* DZ-12 | maize | Y | nt | + | – | – | – | + | scaffold | 1 |
| *P. ananatis* F-C2 | acid mine drainage | n/a | nt | + | – | – | – | + | contig | 1 |
| *P. ananatis* FDAARGOS_680 | clinical | n/a | nt | – | – | – | – | + | complete | 0 |
| *P. ananatis* LMG 20103 | Eucalyptus | Y | Y | + | – | – | – | + | complete | 1 |
| *P. ananatis* LMG 2665 | pinneapple | Y | Y | + | – | – | – | + | scaffold | 1 |
| *P. ananatis* LMG 5342 | clinical | Y | Y | + | + | – | – | + | complete | 2 |
| *P. ananatis* M232A | maize | n/a | nt | + | – | – | – | + | contig | 1 |
| *P. ananatis* MMB-1 | soil | n/a | nt | + | + | – | – | + | contig | 2 |
| *P. ananatis* MR5 | groundnut plant | n/a[e] | nt | – | – | – | – | + | contig | 0 |
| *P. ananatis* NFIX48 | n/a | n/a | nt | + | – | – | – | + | scaffold | 1 |
| *P. ananatis* NFR11 | n/a | n/a | nt | + | + | – | – | + | scaffold | 2 |
| *P. ananatis* NN08200 | sugarcane | n/a[e] | nt | – | – | – | – | + | complete | 0 |
| *P. ananatis* NS296 | rice seed | n/a[e] | nt | – | – | – | – | + | contig | 0 |
| *P. ananatis* NS303 | rice seed | n/a[e] | nt | – | – | – | – | + | contig | 0 |
| *P. ananatis* NS311 | rice seed | n/a[e] | nt | – | – | – | – | + | contig | 0 |
| *P. ananatis* PA13 | rice | Y | Y | + | – | + | – | + | complete | 2 |
| ***P. ananatis* PA4** | onion seed | Y | Y | – | – | – | – | + | contig | 0 |
| ***P. ananatis* PaMB1** | n/a | Y | nt | – | – | + | – | + | scaffold | 1 |
| *P. ananatis* PANS 01-2 | onion | Y | Y | + | – | – | – | + | contig | 1 |
| *P. ananatis* PANS 02-01 | n/a | n/a | nt | + | – | + | – | + | scaffold | 2 |
| ***P. ananatis* PANS 04-2** | thrips | N | N | + | – | + | – | + | contig | 2 |
| *P. ananatis* PANS 200-1 | herb | N | N | – | – | – | – | + | scaffold | 0 |
| *P. ananatis* PANS 99-23 | grass | N | N | – | – | – | – | + | contig | 0 |
| *P. ananatis* PANS 99-3 | onion | Y | Y | + | – | – | – | + | contig | 1 |
| *P. ananatis* PANS 99-36 | coffee plant | N | N | – | – | – | – | + | contig | 0 |
| *P. ananatis* PNA 06-1 | onion | Y | Y | + | – | – | – | + | contig | 1 |
| *P. ananatis* PNA 07-1 | onion | Y | Y | + | – | – | – | + | scaffold | 1 |
| ***P. ananatis* PNA 07-10** | onion | N | N | + | – | – | – | + | scaffold | 1 |
| *P. ananatis* PNA 11-1 | onion | N | N | – | – | – | – | + | scaffold | 0 |
| ***P. ananatis* PNA 14-1** | onion | Y | Y | – | – | – | – | + | contig | 0 |
| *P. ananatis* PNA 15-1 | onion | Y | Y | + | – | – | – | + | contig | 1 |
| ***P. ananatis* PNA 200-3** | onion seed | Y | Y | – | – | – | – | + | contig | 0 |
| ***P. ananatis* PNA 200-7** | onion seed | N | N | + | – | – | – | + | scaffold | 1 |
| *P. ananatis* PNA 86-1 | soil | n/a | nt | – | – | – | – | + | scaffold | 0 |
| *P. ananatis* PNA 98-11 | onion | Y | Y | + | – | – | – | + | scaffold | 1 |
| *P. ananatis* PNA 99-7 | onion | N | N | – | – | – | – | + | contig | 0 |
| *P. ananatis* R100 | rice seed | n/a | nt | + | – | – | – | + | complete | 1 |
| *P. ananatis* RSA47 | rice seed | n/a[e] | nt | – | – | – | – | + | contig | 0 |
| *P. ananatis* S6 | corn seed | n/a[g] | nt | – | – | – | – | + | contig | 0 |
| *P. ananatis* S7 | corn seed | Y | nt | + | – | – | – | + | contig | 1 |
| *P. ananatis* S8 | corn seed | n/a[g] | nt | – | – | – | – | – | contig | 0 |
| *P. ananatis* Sd-1 | rice seed | n/a | nt | – | – | – | – | + | scaffold | 0 |
| *P. ananatis* SGAir0210 | tropical air | n/a | nt | – | – | – | – | + | chromosome | 0 |
| *P. ananatis* strain 1.38 | rice | N[g] | nt | – | – | – | – | + | contig | 0 |
| *P. ananatis* SUPP2219^ | rice | Y | Y | + | n/a | – | – | n/a | locus | 1 |
| *P. ananatis* UBA12293 | metagenome | n/a | nt | – | – | – | – | + | scaffold | 0 |

-continued

| Strain (sorted alphabetcally) | Isolation host/environment | Associated with plant Pathogenicity | Associated with onion disease | Hvr BGC* | Pgb BGC* | Putative phosphonate BGC-A* | Putative phosphonate BGC-B* | C-P lyase pathway** | Genome completion level | # pepM per strain |
|---|---|---|---|---|---|---|---|---|---|---|
| *P. ananatis* Weeds_Lee_18a | tomato and pepper phyllosphere metagenome | Y | nt | − | − | − | − | + | contig | 0 |
| *P. ananatis* YJ76 | rice | n/a[e] | nt | − | − | + | − | + | complete | 1 |
| *Pantoea* sp. AG702 | rice | n/a | nt | + | − | − | − | + | scaffold | 1 |

bold text = strains with exceptions to the correlation between hvr and pathogenicity
n/a = data not available
nt = not tested
[g]= strains that show ability to promote plant growth based on data from the associated reference
[e]= strains that exhibit an endophytic lifestyle based on data from associated reference
^deposited as only a virulence determining genetic locus not full genome
*locus identified based on presence of pepM gene and the associated genomic region referenced to *P. ananatis* LMG 5342 hvr gene cluster
**locus identified based on presence of phnJ gene
***denotes strains that were sequenced in this study (see Materials and Methods)

|  | Hvr BGC | Pgb BGC | Putative phosphonate BGC-A | Putative phosphonate BGC-B | C-P lyase pathway |
|---|---|---|---|---|---|
| Total positive strains | 27 | 3 | 8 | 1 | 64 |
| % of total strains | 42% | 5% | 12% | 2% | 98% |
| Total # strains with at least 1 pepM | 32 | — | — | — | — |
| % of strains with pepM | 49% | — | — | — | — |
| # strains with one pepM | 25 | — | — | — | — |
| # strains with two pepM | 7 | — | — | — | — |

Example 5. Cytotoxicity Profiling

Figure 8:
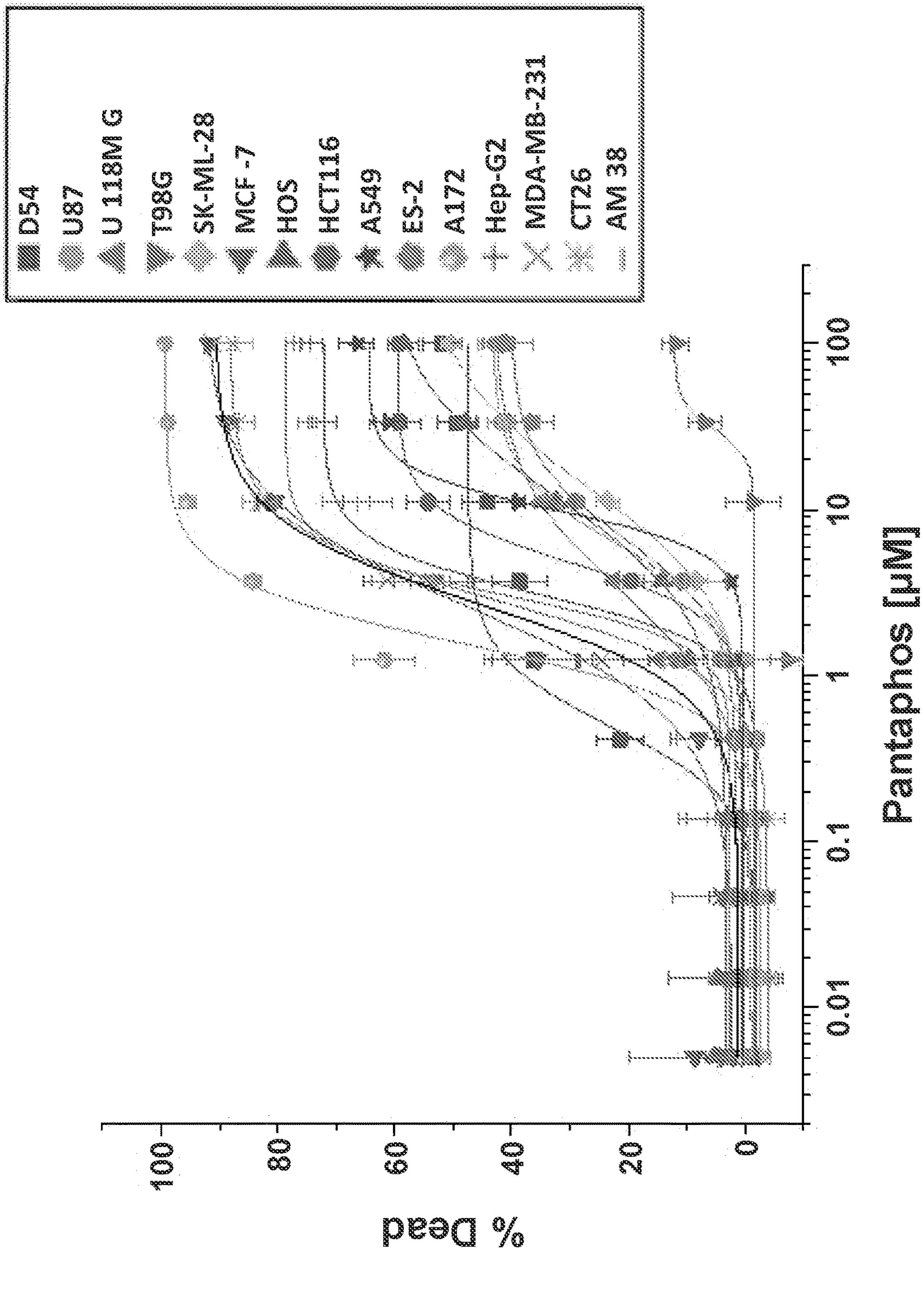
FIG. 8. Cytotoxicity of pantaphos across various cancer cell lines. Assays were conducted as described (mBio. 2021 Feb. 2; 12(1):e03402-20), using the Alamar Blue method with 72-hour treatment using Raptinal (50 mM) as Dead cell control; n=3. Cell seeding densities: CT26 (colon carcinoma) 2000 c/w; HOS (osteosarcoma) 2500 c/w; ES-2 (ovarian carcinoma), HCT-116 (colorectal carcinoma), A-549 (lung carcinoma), A-172 (glioblastoma), D54 (glioblastoma), U87 (glioblastoma), T98G (glioblastoma), SK-ML-28 (melanoma), MCF-7 (breast cancer), AM38 (glioblastoma) and MDA-MB-231 (breast cancer) 3000 c/w; U118MG (malignant glioma) 4000 c/w; HepG2 (liver cancer) 8000 c/w. c/w=cells per well. $IC_{50}$ and $E_{max}$ values shown in Table 6 were extracted from the raw data plotted in FIG. 8.

We previously conducted cytotoxicity profiling against a panel of human cell lines, including normal fibroblast cells (HFF-1 cell line), and five cancer cell lines (HOS (human osteosarcoma), ES-2 (human ovarian cancer), A-549 (human lung cancer) and A-172 (human glioma). Pantophos showed modest cytotoxicity to several human cell lines (Table 6). With the exception of one ovarian cancer cell line (ES-2), which was unaffected at the maximum dose, the $IC_{50}$ levels were roughly similar, in the range of 6.0 to 37.0 mM for each of the cell lines tested. One glioma cell line (A-172) was especially sensitive to pantaphos ($IC_{50}$ of 1.0 mM). To ask whether this sensitivity is specific to glioma cell lines, we expanded the panel to include an additional ten human cancer lines (FIG. 8 and Table 6). Consistent with previous data some cell lines are sensitive, while others are resistant, including the glioblastoma cell line TG98. Thus, pantaphos cytotoxicity is not a feature of all glioblastomas. However, cell lines from other cancer types, including MCF-7 (breast cancer) MDA-MB-231 (breast cancer) CT26 (colon carcinoma) HepG2 (liver cancer) AM38 (glioblastoma) were sensitive to the compound. These data suggest that these cell lines carry mutations that confer sensitivity to pantaphos, paving the way for use of the molecule as a therapy for carcinomas carrying these genetic markers.

TABLE 6

Cytotoxicity of pantaphos across various cancer cell lines.

| Cell line | $IC_{50}$ | $E_{max}$ |
|---|---|---|
| D54 | ND | 46-58% |
| U87 | ND | 38-48% |
| U118MG | ND | 38-45% |
| T98G | >100 | ND |
| SK-ML-28 | ND | 47-51% |
| MCF-7 | 2.88 + 6.28 | 90-92% |
| HOS | 36.98 + 6.28 | 58% |
| HCT-116 | 10.42 + 2.00 | 59% |
| A-549 | 14.73 + 0.61 | 66% |
| ES-2 | >100 | ND |
| A-172 | 1.01 + 0.06 | 99% |
| HepG2 | 4.22 + 0.57 | 71-77% |
| MDA-MB-231 | 2.68 + 0.23 | 91% |
| CT26 | 3.38 + 0.09 | 81-92% |
| AM38 | 3.97 + 1.01 | 74-78% |

Example 6. Nucleic Acid and Amino Acid Sequences

| Gene Name | Nucleic Acid Sequence | SEQ ID NO |
|---|---|---|
| hvrA | ATGATCAAAAAACTTATTGCAGAAAAGGGTACTCTGATTTTTATTGAGG CCCATAATCCGCTCTCCGCATTAATTGCGTCTAAAGCAGAACAAACTAA TTCAGAAGGCCGTATTGTCAAATTTGACGGTATATGGTCAAGCTCGTTA ACGGACTCAGCATCTCGCGGTATTCCCGATAACGAAACACTGGCATTA AGCAGCAGGTTAGAAAATATTGCTGATATCCGAAATGTGACAGACATG CCCATCATCATGGATGCTGATACGGGGGGAAAACCAGAACATTTTAGT TATTACGTAAAAAGAATGATTAACAACGGTGTAAATGGCGTCATCATC GAAGATAAAACAGGATTAAAGAAAAATTCTTTGTTCGGCACTGAAGTA GAACAGACTCTCGCGAGATATTAATGATTTTTCAGAGAAGATTAAAAGA GGAAAATCTGCAGTTTATATTGATGATTTTATGATCATAGCCAGACTTG | SEQ ID NO: 1 |

-continued

AAAGTCTTATTGCAGGGTTCGACGTAGAACATGCACTCGAACGTGCCG
ACGCATACGTCGAAGCCGGGGCAGACGGAATTATGATTCATAGTTGTA
AGAAGACTCCGGATGAGGTTTTCTTATTCAGTACGAAATTTCGGAAAA
AATATCCATCAGTACCATTAATTTGTGTTCCTACTACTTATTCTGCAACC
AGCAACAGAGAACTCAGTGAAGCGGGTTTTAACGTGATCATTTATGCA
AACCATATGCTCAGGGCTGCTTATAAAGCAATGGAAAATGTTTCAAAA
GAAATATTGAGATATGGCAGGACGGCAGAGATAGAAAAATCTTGCAT
GAGTGTAAAGGAAATTATTTCACTGATTCCTTAA hvrB SEQ ID NO: 2

TTGCATGAGTGTAAAGGAAATTATTTCACTGATTCCTTAAAGAGAATGA
CCATGAAAAAAAAAGAGATGATAATAGGTGCCTATATATCGTATGGAA
CAGGACATCATCCTGCTTCATGGCGCGAAAGTGGCGTAAATGCAGCGG
CAGCGCTTGATATTGATACGTATGCCAATCTTGCAAGAGTATGTGAGA
AAGGATTAGCTGATTTACTTTTTCTTGCAGATACGCCTTCTGTATTTCAG
GACAATATGGACGGTTATGGCAGCAGGGTATCTGTACTGGAGCCATTA
TCATTATTATCGTATTTAGCATCTCAAACACAAAATATTGGGCTGGTTG
CGACGGCTTCAACGACGTACAAACACCCTTACAACATTGCGAGGGAAT
TTGCTTCGCTGGATTACATTAGCAAAGGAAGGGCAGGGTGGAATCTG
GTGACATCCTCAAAGTCGGATGCGGCTAAAAACTTTGGCCTTGCCGCT
CATCCAGAACATTCAAAGCGTTATGATATGGCCTGGGAAGCATGGCAG
GTTATCAGTGGTTTGTGGGACAGCTGGGAAGACAATGCTTTAGTAAGG
AATAAAACCAGTGGACAATTCTTCGTTAAGGATAAATACCGGGAAATA
AATTTTGAGGGTGAATATTTTAATGTAAAAGGCCCATTAAACATAGCTC
GCCCTCCTCAGGGCTATCCCGTCATCGTCCAGGCGGGTTCCTCTGAGG
AAGGAAAAGAGTTAGCTGCAAAAACAGCAGATATTGTTTTTACTGCAC
AAAACAATATTGAAGATGCAAAAAAATTCTATGATGATCTTAAAGGGC
GAATGGAAAAATACGGAAGGTCAAAGAGTGAACTTCTTATTCTTCCCG
GATTAAGCTTTTATATTGCAAGTGACGAATCTAAAGCCCGTAAAAAGCT
TAATGATCTCAACGCACTGATCCCTCAATCATTTGGCTTAAGTATGTTAT
CAGATTTACTGGGTGGGGTTGATTTAAAAAACAATGATCCTGAAGGAC
CATTACCAGATTTACCGAAATCTAATGGTAATCAGAGTAGACAAAAAA
TTATTATCGATTTAGCTCGAAAAGAAAAACTATCTATCAAGCAACTTTA
TGAAAAAATAATCATTTCAAGAGGACATTATACATTTACAGGTTCCTAT
CAAGATTTAGCAGATGAGATGATTAAGTGGGTTGAAAATGAAGCATGT
GATGGTTTCAACATTATGCCTCCTCTCATGCCTGAATCTCTTATTAATCT
TTTCGATCATGTCATTCCACTTATTCAGGCAAGAGGATGGTATAAAAAA
TCATATTCTACTGGAACATTAAGAGAAAAACTGGGGCTTAAAAGACCT
ACTAATAAATTGTTTAATCAATAA hvrC SEQ ID NO: 3

ATGCTTAATAAAAATCTGATTCTTGAAGATACCACTTTACGTGATGGTG
AGCAGGCGCCAGGTGTTGCATTTACACCAGAGCAAAAAGTAGAAATTT
TTTATCTACTTGCAAATATGGGCGTTAAATGGATCGAAGCCGGAATAC
CTGCGATGAAGGGTGATGAAGTAAAGGCTCTGTCGGAAATGTTAGAG
AGAAAAAATGAAATTAACATCATCGCGTGGAACCGAGGCGTGCTTGAA
GACATTGAGTACAGTATCTCACTTGGATTCAAAGCGGTGCATATCGGG
CTACCGACTTCAGCTATCCATTTAGAGAAAAGCGTTAAGAAAGATAAG
TCCTGGCTTGTAAAGACGGCTTCAGATTTAGTTAAGTTTGCCAAAGACA
AAGGGATGTTTGTTTCTATCAGCGCAGAAGATATAGGCCGAACAGATA
TTGGATTCTTACAGGAGTATGCACAGGTAGTTGCTGAGGCTGGAGCCG
ATCGTCTTCGCCTCTCTGACACGATTGGTATTCTTTCTCCTGCACAATAC
AAAGAAAAAGTCTCTTTGTTAAATAAGAACGTCAACATCGATTTGCAGT
GCCATTGCCACAATGATTTTGGTTTTGCAGTTGCTAACACGCTGGCAGG
CATTGAAGCAGGAGCACGCTACTTTCATGTCTGCGTCAATGGCATTGG
TGAAAGGGCTGGAATGCCAGACCTGGCACAAGTTGCTATGGCATTGCA
CTTTTTCCACGGGGTTGATTTAGGGCTCGATTTAACAAAATTAATCGCG
TTGAGTGAAACGGTCGCCAGGTACAGCCATCAAAAAATCAGTCCATGG
CAGCCGATCGTAGGCGATAACGTTTTTGCACATGAATCGGGCATTCAC
GCAAATGGTATGCTCAAAGACAGCAGTACTTTTGAACCCTTCGACCCA
GCTACGGTGGGAGGAGAACGACGTCTGGTCGTGGGTAAACATTCCGG
TCGCGCCATTATCAAACATTTTCTCGAAGAATCAGGCGTGAAAGCTGCC
GACGATAAGGCTCTTGATCGCTGTTTAGAACGCGTGAGAAGTCATGCC
GTGCGCCACCCCGGTGGGATCCCTCCACATGTATTAGTTGATCTGTATA
CCGCGGGGTAA hvrD SEQ ID NO: 4

ATGAAAAGTAATCAGCCGATTGTTAACCAGATCATTGCGTCACACAGT
GGCAGAGGTCAGGTTTCAGCAGGTGAACTGATCACGGTAGATGTTGA
CTACGTCTATGTTCAGGATGGAAATTCACCGACCGTGGCAAAACTGTTT
CAGGATTATCATCTGTCTGAGGTGCTAAAACCCGATAAAATCGGGTTCT
TCTTCGACCATTCAGTTCTGGTACCTGATAAAACCATGGCTAAACGTGT
CAACGAGGCCATGGAATTTGCAAAAAAACTTGGAATAAACATCTATTC
ACGAGGGGAGGGAATTAGTCACGTCATTGCCCTGGAGAGTAAAATAT
TTAAACCCGGCAATATAGTGCTGGGCGCAGATTCCCATACTTGTACAG
GGGGGGCCGTACAGTCTTTAGCGCTGGGAATGGGGGCTTCGGATATT
CTGGTTGCTATGTTAACAGGACAAACGTGGTTGAAAGTCCCTCAAACA
GTCCATTTGTGTATTAAGGGTAAAACGGGAAAAGATGTGCGGGCAAA
AGATGTCATGTTGGCACTTTTAAATAAGTACGGACAAACACCATTTCTT
TATAAATCGATCGAAGTTTCAGGGGAATGGGCAGAAGAGCTAACGCTT
GACGAAGCTGCAAGTTTTGCAAGTATGGCTGTTGAGTTAGGAGCCAAA
TGCATATTTATGCCAGATGGGCAAGGCAGGCCTGAGGGGCTATTGAA

-continued

```
         GGCGGATGCCTCAGTGGCAGACAGTGTCATCAATTTTTCTGTATCAGA
         ATTAATGCCCCATATCGCACCACCTCACAGTCCTTTGTATGCTAAACCTG
         CAAATGACTTTGAGGGTCTGAAATTTGATTATATTTTCATTGGAAGCTG
         TACTAACAGCAGACTTGAAGATATCAAAGAGGTGGCCGAAATTGTTGC
         TGGTAAAACAATACATCCCGATATTCACTGCCTTCTGACGCCAGGATCG
         AAAAGTGTTTATCTAAAAGCTCTCCAGGGGGATATATCGATACGCTTA
         TCCGCTCGGGCATTATTGTCACCCCACCGGGTTGTGGAGCTTGTGTGG
         GTACCCAAGGAACCATTCCTGCGGATGGGGAGAAAGTATTAAGTACG
         ATGAACCGCAATTTTAAGGGAAGAATGGGGAATGCTGAGGCAGACAT
         CTTTTTATGTTCTCCACGAACTGCAGCGATGGTTGCATTGAACGGCACT
         GTTCCACATTTTGAGGGAGAGTCCGCATATGAGTAA

hvrE     CTGTTCCACATTTTGAGGGAGAGTCCGCATATGAGTAAAACTGCTGAA          SEQ ID
         AATTATCGCGTCAGACGCGTGGAAGGGAACATCTCGACCGACGATATT          NO: 5
         ATACCTGCGCGCTATAAACATATGTATACCGAGCCGGCCCAGCTGGCA
         CCGCATCTTTTTGAGAGCCGTTTTCCCGGATTTAGGGAAACGCTCAGTA
         TCAATGATGTGCTTGTATGTGATCAAATATTCGGTATAGGGAGTTCGC
         GGGAGCAGGCAGTAACAACTCTGTTGGCATGTGGTGTTAAATATGTAT
         TTTCCCCTTCTTTCGGGAGGATTTTTTTAGGAACTCTTGGAATTTGGGT
         TTACATGCGATTGAGGTCGATACGAGTGAACTTGCAGATTTAAGTGAA
         ATTAAAATAGAACTGACTGGAGGGGTAATTTATACAGAAAATAATCAA
         ATAAATTTTTTCCCTCCCAGCTCGCAGATGACGGCAATTGTCAGTGCAG
         GTGGCATAATACCCTACACCATAAATAAAATTATGGAAAAAAAGGTG
         ATATTTTAAGAGGTTATAGCAATGAAAAGTGA

hvrF     ATGAAAAGTGAAAAGTTTGATGGTTTGGCTGATAACTATGATAAATAT          SEQ ID
         CGTCCCCGTTATCCTGCAATCCTTTTCAAGGAAATCCATGACTGGATGC         NO: 6
         AGCCGTCTGCCAAAAATATATACGATATTGGCGCAGGCACAGGTATTG
         CTATTGAAGGTATGACACGTGTCACTGGAAAACACTATGATTTCACGG
         CGATAGATATTTCTGAAGATATGATAAAAAAAGGAAGGGAAAAACTG
         CCTGGTACGACTTGGGTTAAAGGAAAAGCGGAAGATATTCTTTCTGAT
         AAAAGCCGTATTGACGTCATTATGGCGGCACAGTCCTTCCAATGGATG
         GATAGAGCTAAAACATTAGAAGTTTCGATAAAATCTTTAAATAAGGGC
         GGGGTTTTTGCAGTTTTGCAAAACAATCGAGATTACAGAAATAATGAA
         ATGCTTAACAAATATGAAGGTTTGCTAGAGAAATTTAGTCCAGGTTAC
         AGCAGACATTATCGCGACTATGACTATGAAAATGAAATCACCAATGTTT
         TTAAATTGCCTATTGCTAACTTTAAGAAAGTCGTCACAGGGTGGACTAT
         GGAAATGATTTCAGAAGATTTTTTTGGATTCATTTCTTCCTCAACCCAG
         GTACAAAGAGCTATTGAGAACGATCGTAATGGATTCTGGAAGGAGATT
         GAAATCTTGATTGACGAACACTCAGTTGGTGGAAAAATTAGCATAGAT
         TATATAAGTGAGTTATTTATAGCTAAGAAGCGTGATGATTCATAG

hvrG     ATGATTCATAGCATGACGATTCAGGACATCAGCATTGAACAAGCTTCG          SEQ ID
         TATGAAGATGCGAAGCTGTTAAGAAAGGCTTTAGAAAAAGTTTACGAA          NO: 7
         CCTTATACACTGAATTTCTCACCTACCGCTTTGCAGTTTACTGAAAATAT
         CATTGCTCAGGAATCCTCGAAGTGGCTAGTCGCGAAATACAAGTCAGA
         CATTGTGGGGGCAGTGAGATATGAACTTTATGATATTTATCTGGACTTC
         CATTTTCTCTGCGTCACACCACCATTCAGAAAAATGGGAGTAGGGAAT
         GAATTATTTCATAAACTGAAGAAAATAGCGTATGAAAAAAGAAAGGAT
         TTTATGAAGATCGTTTTGCGAGATTCGCTAAGCTATAACCGACGCTATT
         TTGAAAGTAAAGGATTTTACTTTTATCATAAATACCAGACAAATATGCA
         TAGTGTATTTATTTTAAAATTAAACGGTGAAAAGCCATGA

hvrH     ATGAATAAAAAAGCATTGGTTATTGGGTTGAAAAGTAATATGGAAAGA          SEQ ID
         GTCATCAAAGGGCTCAATGAGATAGAATTTATTATTATTGACAGAGGA          NO: 8
         ACACTGGATAACGAAAGTATAGATTATATCATTAATCTTTCAGATGATT
         TAATGCATAAAAAATCATTCAGTTATGTTATAGCCAGTTCTGAGGATTT
         TATCGCTTTGGCTGGGTTATTGCGTAATCGTTATTCACTTTATGGTGAA
         AAATATTATAAAAGTACAATTGCAACCAATAAATTCCTGATGCGTAATT
         TTTGCTCAGGTTTTTTATCCTGTCCAAAGTTCTGGCTATCAGGTGAGAT
         CATCAATTCAGAGAATCTTTTACTGTCATCCCAGAAAGATTACATCGTA
         AAACCTCTTACAGGTAGTTCTGCAAAACATGTCGAAACAGTCACACAG
         GAAGACTTAAACCAATATCTTAATGAAAATAACAAATTGATGTTAATTG
         AAGAAAAGGTTTTAATGAGAGATGAATATCATCTTGATTGTATAATCA
         AAGACGGTAATATCCTCTTTTCAACACTGTCAATTTACGACAGGCCTAT
         ACTCGAGGCAAAAAGTAAAAACAGAGCCAGTATCAACTTACCCGATGG
         CACACGGCTTCATGAAGATGCCTTAATACTTGCCACGAATTTGCAAAGT
         CATTTTGAAATGACTAATGGCGTTTTTCATATTGAAATGTATCATACTCA
         GGATGGATTTATACTCGGTGAGTTTGGTATCCGCCCTCCCGGAGCGGG
         TGTGACCGATATGTATTATATGTATAGAGGCGTCGATTTCTGGGAGGC
         ATTTATTTATTCTCAGATTGATAAAGAATTTATTTTACCCCTAAATCATA
         AGTCCGATAAATATTGTGCTGCTATTGGGATATGTTCTTCTTTCCCGGT
         CGATGATATCAGAAGTACGTCAAAAGTATCCGTGGATAAATATGTAAA
         TTTGCGTGAGAATGCTGCTAAACCCGCAGTTCCCAGTTCAACGTCTTTT
         AATCATATGATTTATGTTTCTTCATCATCCTTAGAAGAAATAAGGAATTT
         TTTGCATGATATTTCTGACAGACAAGAGTAA
```

-continued hvrI SEQ ID NO: 9

ATGTTAAAATATGAAACCAAAAAAAACGCTTTCTTCCAGATATACAATT
TTCTTTCATGCTCGGCTGAAGGGATTCAGACGGTTATATTTTTGTGGCT
TATATATCATGAAACTCATAGTCCGATGCTTGTCAGTCTGACTATAGTTT
CTTCATATCTTCCATCAGCCGTATTAGGATTCTTTTTCCTCAAAAAAGCT
GATGCGAGCAGTCCTGGAAAACAGTTATTTATCAGTAATGTTTCTCTTA
GTGCCATATCGCTAATTGTCTATTTTATTTTAATGAGAAATGAGGGTTTT
GAACTAATCACGCTCAGTATCTTTTATTTGGCACAGGCCGTATTATCTG
TTGTCAAAATGTTTAATAAGACATCCCAAAATCGCATTATCAGAACAGC
ATTCAGTAATAGTGATGCAATAAAAGCACTTCAGCTTGCCTCCTCTGGC
ATGCAGGCCGCTCAGGTTTTTGGCGCGGCCATAGGAGGATGGGCTATC
AGTACGGGTTACTACATGCAAGCGCTCATGCTGACCTGCTGCATCTACC
TTTTGAATATTTATATTTCGACACTTTTTGAGAAAGGGAATCCTGATAAT
AAAGACGCTGAGGTTATTGTGCAGATTCACTCTGTCACTAAGAAAAAT
GAATCCTTTACATATCTTTTTCGCAGTAAGGACTTTTTGTTACCCTTGAT
TTTTACTGTTCCATCAAGTGGAGCTTTACAATTTTTAAACACATCCCTTC
CTTCATTATCTTCTCTATATGGTAATAGCGAGAAAATTTATCCAGTGCTG
AATATGACTCTACAATGTGCTGTCATTATCTCGGGGATAGCAGCAGCA
CTCAATATGCTTTCTCTAAAGTCTTCATTACGGTTTTCTCTGTGTATTTCT
GGCATCTGTCTGATTTTGATGTGTTTATCATCGAGAAATTATTATGCCG
TATACTTTTTTTTATTTCTCACTTCTTTTTTTGTTTCATGGCATATGATTTC
TATTAAGGTACTCACGAATCAAATGCCTGATATAGAAAATATTGGTAAA
TTCACAATGATGAGAAACTCAGTCGCTTCTGGTGTGAAAATTGTCTTTT
CTATTTCGTCTGGTGCTTTTTTGACTTTTTACAGCATAACTACAACTTATC
TAATACTTGCGATACTGCTTATTTTTTTCAATGTACTATGGGTTTGTCAG
AGTCGCAGTTTTAACTATGAGGATTTAGGTGATGTTAAATTTCAAAAGT
GA hvrJ SEQ ID NO: 10

ATGTTAAATTTCAAAAGTGATTTTTCTGAATTTATTACTGGTTTTTATCTT
AAACAGTTTACTCATTTAAATACGCAGGAAAGAGAACATGTGCTTGAA
ACGCTTGGCGTCACACCCAGCGCAATCAATGAGTTTATAACATCAGAA
GATATTTATATTACCTTACCTCATGCAAGTATGAATGTTTTTTTTCCAAG
AGCGGGGGTCTCACGTTATGTCTACGATCTACAAAATAGTAACAAAAA
CGCGTTCCATTTAAGGTTTTTCTTGACCCATACCAACTTTAGCGATCTGA
ACTGGCGCCCTTATGCATGGTGGTTTAATAACGGCGGGAAAATAGATA
AACTTACCTTTTTCACACGAAATAAAAAAAAGAAACATAATATCGTTTA
CTCGCTAAAACCAAATGAAATGCACTCTGCCTCTGTAGATCGACGTCTG
CGTCATGACTTTGATACAAGTATGAAGTTTAAACGTATTTCTCTTAGCTT
CATCTATATGACAGCCGTTCAAGAGGTCAATAGCGGTTTTGCACATAA
AGGCCGTACCCTTTATCTCCCACTTGACGCATTTGTAGCTTTTATTATTC
ATCAGGCAAAAAACGATGTTATATCTTTTAATTTTTTAGAAGCTTTTTTA
AGCCAGGCACAATGCAGAAGACTGAATGGCGAAGAATTGAGTTTTACC
AGTGAATGGCGCGATGCATTTATCTTTGATAATTTTACAAACATTGCGC
TGTTAAATTTTTTTCAGCCTGCAGCATTTGTGGGAGGCGAAAAAATGG
ATAACTACTGGCATCAGGTGATTGAAAAATGGAAAATGGCATTACCAA
ATCAATCTGAAGTTGAGTTTGCGTTACCCACTAATCTGGTCATGCCTGC
CGTTCAAGAGTATATTTACCCTTATAAACCATCAAGCGATATAGCAGAA
CAGCTTATTAAAAATAACATCCCATACAGTCTTACCATGGCTATTCAGG
AACATGATCTTTTTTCAAAGAAAGAATAA hvrK SEQ ID NO: 11

ATGCTAGATAAAAGTGCTTTTCGCCACGCAATGTCGCATCTTCCTACTG
CAGTCACTATTGTAACATCAAGCGGCTCCTGCGGGGCTGCAGCATGTA
CAGTTTCATCCGTGTGTTCTGTCACCGACGACCCACCCACTTTACTCGTA
TGTATAAATCGTGCCTCCAATAACAATAGTGTTATAAGAAATAATGGCT
CTTTGTGTGTCAGCATTCTTTCAGGAGAGCAAAGCAACATTGCAATGCA
ATGTGCTAATCATCAGGTTTCAGTTGAGGAGCGCTTAGCATTATTCGAC
GCAGACGTTCTGGTCACGGGGTCTCCTGCTGTAGTTGATTCCGTTTGCT
GTTTAGATTGTCGTGTAGATAATATTGTGGAATCAGGAACCCACTCTGT
CTTCTTTTGTCAGGTTCTTTCTTCTAAAGCTTTTGTGGGGAAAGATGCG
CTGGTTTATTATTGCCGGAATTATCATCGTGTATCATAA hvrL SEQ ID NO: 12

ATGATGAAAAGTTTAATTATTACGTCGCATTTTAATAGTGATTTATCCTC
TATGGCATGCGATGAGTTTGGATTAAAAAGATCACTAATTTTCTATACT
CCAAAAATAAATGAACTTAGCTTAGGTTTAAAATATGAGTACTACGATA
AGATAGATTCTTACTCTGTAAGATTAATGGAGCTTGGGAATGAAATTG
ATTTTATATGGAGCACTTCCGGTTCTGAAATCAACTCGTTCGCTGAATT
AAAAGCTGTTGAGTTGGCAGGATTAAGAAACATCTATCTAGGCATGAA
TGAAAATGCTTTTTCTACAGCTGCTTATAAAAGCATCACGCAAGAGTTA
ATGGCATTTTTGGGTGTTAGTATTCCCAAAGGGCTTCAATGTAACACAA
AAAAAGAAATACATGATTTCCTTGAATATAATGGTGGAACTATAGTCT
GTAAAGCTAACAATGGAGCAGGTGGTGTAAATCAATTTTATTGCCAAA
GATTTGATGACATATATAAACTCCCTCATGAGGTAACTGATTGGTATGT
AGAACAGTTTCTGAAAGGACTTGAGTTTTCTGTAAACGCTTATATGCTA
AATGGGTTTTATATAGCCTCCCCGATAATGTTTAAAGGCGAAACTGATA
TTCATAGCGGGCACGCAATGGACAAATTCAGGTATATTAGCAAGCTAA
AAAATAAAAGCTTAAATGAAAAAATAAATGCCATATTAAGTAAAATTA
GTAATACCAATATCTTTAATGGATGGATAGAGGTTGAGTTTATAAAAA
CACATCAGGATTTGGTAGTTATAGAAATTAATGCGAGGTATAATGGAA
CAATCAGAGCTACTGGATATGCTTGTAATGAAAATTTATATCAATTGGA

-continued

| | | |
|---|---|---|
| | TTTGGAAAGTAAAATTTATAATAAATTTTCTTCACAATTAAATCATGAAA<br>ACGAAGTCATTGAGATGCCAATTCATTTGAAACTTGAAACAGGTTTAA<br>AAGAATTTGGTTTCGTCCAAAAAATGAAATCTCGAAAAACCAACACAG<br>GAAGGGCCACAATATGGGGTGAAGATCAATGTGAACTATTAGAGAGG<br>ATCAAAAATACTGAATTAGAAATATACTCAGAAAGAATTATTCATGGCA<br>TAAATGAGAGTAAGGAGTTATTCGAAAAATATATTTAA | |
| pTAC promotor sequence | GCGCAACGCAATTAATGTGAGTTAGCTCACTCATTAGGCACCCCAGGC<br>TTTACACTTTATGCTTCCGGGTTTTCTTTGCCTCACGATCGCCCCCAAAA<br>CACATAACCAATTGTATTTATTGAAAAATAAATAGATACAACTCACTAA<br>ACATAGCAATTCAGATCCGGTCCAGTAATGACCTCAGAACTCCATCTGG<br>ATTTGTTCAGAACGCTCGGTTGCCGCCGGGCGTTTTTTATTGGTGAGAA<br>TCGCAGCAACTTGTCGCGCCAATCGAGCCATGTCGTCGTCAACGACCC<br>CCCATTCAAGAACAGCAAGCAGCATTGAGAACTTTGGAATCCAGTCCC<br>TCTTCCACCTGCTGATCCGGATCGATCCCGTTATCGACTGCACGGTGCA<br>CCAATGCTTCTGGCGTCAGGCAGCCATCGGAAGCTGTGGTATGGCTGT<br>GCAGGTCGTAAATCACTGCATAATTCGTGTCGCTCAAGGCGCACTCCC<br>GTTCTGGATAATGTTTTTTGCGCCGACATCATAACGGTTCTGGCAAATA<br>TTCTGAAATGAGCTGTTGACAATTAATCATCGGCTCGTATAATGTGTGG<br>AATTGTGAGCGGATAACAATTTCACACAGGAAACAGAATTGATCCGGC<br>CAAGCTTGTAAGAAGGAGATATACAT | SEQ ID NO: 13 |

| Protein Name | Amino Acid Sequence | SEQ ID NO |
|---|---|---|
| HvrA | MIKKLIAEKGTLIFIEAHNPLSALIASKAEQTNSEGRIVKFDGIWSSSLTDSAS<br>RGIPDNETLALSSRLENIADIRNVTDMPIIMDADTGGKPEHFSYYVKRMIN<br>NGVNGVIIEDKTGLKKNSLFGTEVEQTLADINDFSEKIKRGKSAVYIDDFMII<br>ARLESLIAGFDVEHALERADAYVEAGADGIMIHSCKKTPDEVFLFSTKFRKK<br>YPSVPLICVPTTYSATSNRELSEAGFNVIIYANHMLRAAYKAMENVSKEILR<br>YGRTAEIEKSCMSVKEIISLIP | SEQ ID NO: 14 |
| Hvrb | MHECKGNYFTDSLKRMTMKKKEMIIGAYISYGTGHHPASWRESGVNAA<br>AALDIDTYANLARVCEKGLADLLFLADTPSVFQDNMDGYGSRVSVLEPLSL<br>LSYLASQTQNIGLVATASTTYKHPYNIAREFASLDYISKGRAGWNLVTSSKS<br>DAAKNFGLAAHPEHSKRYDMAWEAWQVISGLWDSWEDNALVRNKTSG<br>QFFVKDKYREINFEGEYFNVKGPLNIARPPQGYPVIVQAGSSEEGKELAAK<br>TADIVFTAQNNIEDAKKFYDDLKGRMEKYGRSKSELLILPGLSFYIASDESKA<br>RKKLNDLNALIPQSFGLSMLSDLLGGVDLKNNDPEGPLPDLPKSNGNQSR<br>QKIIJDLARKEKLSIKQLYEKIIISRGHYTFTGSYQDLADEMIKWVENEACDG<br>FNIMPPLMPESLINLFDHVIPLIQARGWYKKSYSTGTLREKLGLKRPTNKLF<br>NQ | SEQ ID NO: 15 |
| HvrC | MLNKNLILEDTTLRDGEQAPGVAFTPEQKVEIFYLLANMGVKWIEAGIPA<br>MKGDEVKALSEMLERKNEINIJAWNRGVLEDIEYSISLGFKAVHIGLPTSAI<br>HLEKSVKKDKSWLVKTASDLVKFAKDKGMFVSISAEDIGRTDIGFLQEYAQ<br>VVAEAGADRLRLSDTIGILSPAQYKEKVSLLNKNVNIDLQCHCHNDFGFAV<br>ANTLAGIEAGARYFHVCVNGIGERAGMPDLAQVAMALHFFHGVDLGLDL<br>TKLIALSETVARYSHQKISPWQPIVGDNVFAHESGIHANGMLKDSSTFEPF<br>DPATVGGERRLVVGKHSGRAIIKHFLEESGVKAADDKALDRCLERVRSHAV<br>RHPGGIPPHVLVDLYTAG | SEQ ID NO: 16 |
| HvrD | MKSNQPIVNQIIASHSGRGQVSAGELITVDVDYVYVQDGNSPTVAKLFQD<br>YHLSEVLKPDKIGFFFDHSVLVPDKTMAKRVNEAMEFAKKLGINIYSRGEGI<br>SHVIALESKIFKPGNIVLGADSHTCTGGAVQSLALGMGASDILVAMLTGQT<br>WLKVPQTVHLCIKGKTGKDVRAKDVMLALLNKYGQTPFLYKSIEVSGEWA<br>EELTLDEAASFASMAVELGAKCIFMPDGQGRPEGLLKADASVADSVINFS<br>VSELMPHIAPPHSPLYAKPANDFEGLKFDYIFIGSCTNSRLEDIKEVAEIVAG<br>KTIHPDIHCLLTPGSKSVYLKALQAGYIDTLIRSGIIVTPPGCGACVGTQGTIP<br>ADGEKVLSTMNRNFKGRMGNAEADIFLCSPRTAAMVALNGTVPHFEGE<br>SAYE | SEQ ID NO: 17 |
| HvrE | MFHILRESPHMSKTAENYRVRRVEGNISTDDIIPARYKHMYTEPAQLAPHL<br>FESRFPGFRETLSINDVLVCDQIFGIGSSREQAVTTLLACGVKYVFSPSFGRI<br>FFRNSWNLGLHAIEVDTSELADLSEIKIELTGGVIYTENNQINFFPPSSQMT<br>AIVSAGGIIPYTINKIMEKKGDILRGYSNEK | SEQ ID NO: 18 |
| HvrF | MKSEKFDGLADNYDKYRPRYPAILFKEIHDWMQPSAKNIYDIGAGTGIAIE<br>GMTRVTGKHYDFTAIDISEDMIKKGREKLPGTTWVKGKAEDILSDKSRIDV<br>IMAAQSFQWMDRAKTLEVSIKSLNKGGVFAVLQNNRDYRNNEMLNKYE<br>GLLEKFSPGYSRHYRDYDYENEITNVFKLPIANFKKVVTGWTMEMISEDFF<br>GFISSSTQVQRAIENDRNGFWKEIEILIDEHSVGGKISIDYISELFIAKKRDDS | SEQ ID NO: 19 |
| HvrG | MIHSMTIQDISIEQASYEDAKLLRKALEKVYEPYTLNFSPTALQFTENIIAQE<br>SSKWLVAKYKSDIVGAVRYELYDIYLDFHFLCVTPPFRKMGVGNELFHKLK<br>KIAYEKRKDFMKIVLRDSLSYNRRYFESKGFYFYHKYQTNMHSVFILKLNGE<br>KP | SEQ ID NO: 20 |

-continued

| | | |
|---|---|---|
| HvrH | MNKKALVIGLKSNMERVIKGLNEIEFIIIDRGTLDNESIDYIINLSDDLMHKK<br>SFSYVIASSEDFIALAGLLRNRYSLYGEKYYKSTIATNKFLMRNFCSGFLSCPK<br>FWLSGEIINSENLLLSSQKDYIVKPLTGSSAKHVETVTQEDLNQYLNENNKL<br>MLIEEKVLMRDEYHLDCIIKDGNILFSTLSIYDRPILEAKSKNRASINLPDGTR<br>LHEDALILATNLQSHFEMTNGVFHIEMYHTQDGFILGEFGIRPPGAGVTD<br>MYYMYRGVDFWEAFIYSQIDKEFILPLNHKSDKYCAAIGICSSFPVDDIRST<br>SKVSVDKYVNLRENAAKPAVPSSTSFNHMIYVSSSSLEEIRNFLHDISDRQE | SEQ ID<br>NO: 21 |
| HvrI | MLKYETKKNAFFQIYNFLSCSAEGIQTVIFLWLIYHETHSPMLVSLTIVSSYL<br>PSAVLGFFFLKKADASSPGKQLFISNVSLSAISLIVYFILMRNEGFELITLSIFYL<br>AQAVLSVVKMFNKTSQNRIIRTAFSNSDAIKALQLASSGMQAAQVFGAAI<br>GGWAISTGYYMQALMLTCCIYLLNIYISTLFEKGNPDNKDAEVIVQIHSVTK<br>KNESFTYLFRSKDFLLPLIFTVPSSGALQFLNTSLPSLSSLYGNSEKIYPVLNM<br>TLQCAVIISGIAAALNMLSLKSSLRFSLCISGICLILMCLSSRNYYAVYFFLFLT<br>SFFVSWHMISIKVLTNQMPDIENIGKFTMMRNSVASGVKIVFSISSGAFLT<br>FYSITTTYLILAILLIFFNVLWVCQSRSFNYEDLGDVKFQK | SEQ ID<br>NO: 22 |
| HvrJ | MLNFKSDFSEFITGFYLKQFTHLNTQEREHVLETLGVTPSAINEFITSEDIYIT<br>LPHASMNVFFPRAGVSRYVYDLQNSNKNAFHLRFFLTHTNFSDLNWRPY<br>AWWFNNGGKIDKLTFFTRNKKKKHNIVYSLKPNEMHSASVDRRLRHDFD<br>TSMKFKRISLSFIYMTAVQEVNSGFAHKGRTLYLPLDAFVAFIIHQAKNDVI<br>SFNFLEAFLSQAQCRRLNGEELSFTSEWRDAFIFDNFTNIALLNFFQPAAFV<br>GGEKMDNYWHQVIEKWKMALPNQSEVEFALPTNLVMPAVQEYIYPYKP<br>SSDIAEQLIKNNIPYSLTMAIQEHDLFSKKE | SEQ ID<br>NO: 23 |
| HvrK | MLDKSAFRHAMSHLPTAVTIVTSSGSCGAAACTVSSVCSVTDDPPTLLVCI<br>NRASNNNSVIRNNGSLCVSILSGEQSNIAMQCANHQVSVEERLALFDADV<br>LVTGSPAVVDSVCCLDCRVDNIVESGTHSVFFCQVLSSKAFVGKDALVYYC<br>RNYHRVS | SEQ ID<br>NO: 24 |
| HvrL | MMKSLIITSHFNSDLSSMACDEFGLKRSLIFYTPKINELSLGLKYEYYDKIDSY<br>SVRLMELGNEIDFIWSTSGSEINSFAELKAVELAGLRNIYLGMNENAFSTA<br>AYKSITQELMAFLGVSIPKGLQCNTKKEIHDFLEYNGGTIVCKANNGAGGV<br>NQFYCQRFDDIYKLPHEVTDWYVEQFLKGLEFSVNAYMLNGFYIASPIMF<br>KGETDIHSGHAMDKFRYISKLKNKSLNEKINAILSKISNTNIFNGWIEVEFIK<br>THQDLVVIEINARYNGTIRATGYACNENLYQLDLESKIYNKFSSQLNHENEV<br>IEMPIHLKLETGLKEFGFVQKMKSRKTNTGRATIWGEDQCELLERIKNTELE<br>IYSERIIHGINESKELFEKYI | SEQ ID<br>NO: 25 |

Example 7. Pharmaceutical Dosage Forms

The following formulations illustrate representative pharmaceutical dosage forms that may be used for the therapeutic or prophylactic administration of a composition of a formula described herein, a composition specifically disclosed herein, or a pharmaceutically acceptable salt or solvate thereof (hereinafter referred to as 'Composition X'):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |

-continued

| | |
|---|---|
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution | q.s. |
| (pH adjustment to 7.0-7.5) | |
| Water for injection | q.s. ad 1 mL |

| (v) Injection 2 (10 mg/mL) | mg/mL |
|---|---|
| 'Composition' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution | q.s. |
| (pH adjustment to 7.0-7.5) | q.s. ad 1 mL |
| Water for injection | |

| (vi) Aerosol | mg/can |
|---|---|
| 'Composition X' | 20 |
| Oleic acid | 10 |
| Trichloromonofluoromethane | 5,000 |

-continued

| | |
|---|---|
| Dichlorodifluoromethane | 10,000 |
| Dichlorotetrafluoroethane | 5,000 |

| (vii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for inhibiting growth or formation of a weed comprising contacting the weed, and/or soil in which the weed can form, with an herbicidally effective amount of a composition comprising a compound of Formula I:

(I)

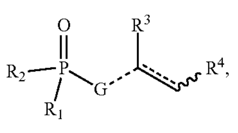

or a salt thereof;

wherein

----- represents single or double bond;

===== represents double or single bond, wherein both ===== and ----- are not double bonds;

G is $X^ACHOR^5$, O, C(=O), C(=$CH_2$), CHP(=O)$(R^6)_2$, or $CX^B{}_2$;

$X^A$ is absent or O;

each $X^B$ is independently H or halo;

$R^1$ and $R^2$ are each independently $OR^A$ or an amino acid;

$R^3$ is —C(=O)$R^7$ or a triazole or tetrazole;

$R^4$ is —C(=O)$R^8$ or a triazole or tetrazole:

$R^5$ is H, —($C_1$-$C_6$)alkyl, —($C_3$-$C_6$)cycloalkyl, aryl, or heteroaryl;

each $R^6$ is independently $OR^B$ or an amino acid;

$R^7$ and $R^8$ are each independently $OR^C$ or an amino acid; and each $R^A$, $R^B$ and $R^C$ are independently H, —($C_1$-$C_6$)alkyl, —($C_3$-$C_6$)cycloalkyl, aryl, or heteroaryl; and a fluid, an additive, or combination thereof;

wherein growth or formation of the weed is thereby inhibited.

2. The method of claim 1, wherein the composition contacts vegetation and/or soil in which the vegetation can form, and growth or formation of the weed is selectively inhibited.

3. A method for inhibiting growth of a cancer cell comprising contacting the cancer cell with an effective amount of a composition comprising a compound of Formula I:

(I)

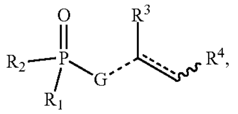

or a salt thereof;

wherein

----- represents single or double bond;

===== represents double or single bond, wherein both ===== and ----- are not double bonds;

G is $X^A$CHOR$^5$, O, C(═O), C(═CH$_2$), CHP(═O)(R$^6$)$_2$, or CX$^B{}_2$;

$X^A$ is absent O;

each $X^B$ is independently H or halo;

$R^1$ and $R^2$ are each independently OR$^A$ or an amino acid;

$R^3$ is —C(═O)R$^7$ or a triazole or tetrazole;

$R^4$ is —C(═O)R$^8$ or a triazole or tetrazole:

$R^5$ is H, —($C_1$-$C_6$)alkyl, —($C_3$-$C_6$)cycloalkyl, aryl, or heteroaryl;

each $R^6$ is independently OR$^B$ or an amino acid;

$R^7$ and $R^8$ are each independently OR$^C$ or an amino acid; and each $R^A$, $R^B$ and $R^C$ are independently H, —($C_1$-$C_6$)alkyl, —($C_3$-$C_6$)cycloalkyl, aryl, or heteroaryl; and a fluid, an additive, or combination thereof;

wherein growth of the cancer is thereby inhibited.

4. The method of claim 3 wherein the cancer cell is a glioblastoma cell.

5. A method for suppressing growth of a plant comprising contacting the plant, or contacting soil near the plant, with an effective amount of a composition comprising a compound of Formula I:

(I)

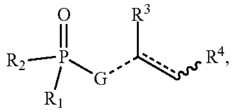

or a salt thereof, wherein

----- represents single or double bond;

===== represents double or single bond, wherein both ===== and ----- are not double bonds;

G is $X^A$CHOR$^5$, O, C(═O), C(═CH$_2$), CHP(═O)(R$^6$)$_2$, or CX$^B{}_2$;

$X^A$ is absent or O;

each $X^B$ is independently H or halo;

$R^1$ and $R^2$ are each independently OR$^A$ or an amino acid;

$R^3$ is —C(═O)R$^7$ or a triazole or tetrazole;

$R^4$ is —C(═O)R$^8$ or a triazole or tetrazole;

$R^5$ is H, —($C_1$-$C_6$)alkyl, —($C_3$-$C_6$)cycloalkyl, aryl, or heteroaryl;

each $R^6$ is independently OR$^B$ or an amino acid;

$R^7$ and $R^8$ are each independently OR$^C$ or an amino acid; and each $R^A$, $R^B$ and $R^C$ are independently H, —($C_1$-$C_6$)alkyl, —($C_3$-$C_6$)cycloalkyl, aryl, or heteroaryl; and a fluid, an additive, or combination thereof, wherein growth of the plant is thereby suppressed.

6. A method for killing a plant comprising contacting the plant, or contacting soil near the plant, with an herbicidally effective amount of a composition comprising a compound of Formula I:

(I)

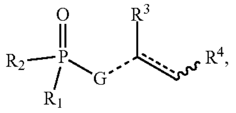

or a salt thereof;

wherein

----- represents single or double bond;

===== represents double or single bond, wherein both ===== and ----- are not double bonds;

G is $X^A$CHOR$^5$, O, C(═O), C(═CH$_2$), CHP(═O)(R$^6$)$_2$, or CX$^B{}_2$;

$X^A$ is absent or O;

each $X^B$ is independently H or halo;

$R^1$ and $R^2$ are each independently OR$^A$ or an amino acid;

$R^3$ is —C(═O)R$^7$ or a triazole or tetrazole;

$R^4$ is —C(═O)R$^8$ or a triazole or tetrazole;

$R^5$ is H, —($C_1$-$C_6$)alkyl, —($C_3$-$C_6$)cycloalkyl, aryl, or heteroaryl;

each $R^6$ is independently OR$^B$ or an amino acid;

$R^7$ and $R^8$ are each independently OR$^C$ or an amino acid; and each $R^A$, $R^B$ and $R^C$ are independently H, —($C_1$-$C_6$)alkyl, —($C_3$-$C_6$)cycloalkyl, aryl, or heteroaryl; and a fluid, an additive, or combination thereof, wherein the plant is thereby killed.

* * * * *

SEQUENCE LISTING

<160> NUMBER OF SEQ ID NOS: 63

<210> SEQ ID NO 1
<211> LENGTH: 855
<212> TYPE: DNA
<213> ORGANISM: Pantoea ananatis

<400> SEQUENCE: 1
atgatcaaaa aacttattgc agaaaagggt actctgattt ttattgaggc ccataatccg 60
ctctccgcat taattgcgtc taaagcagaa caaactaatt cagaaggccg tattgtcaaa 120
tttgacggta tatggtcaag ctcgttaacg gactcagcat ctcgcggtat tcccgataac 180
gaaacactgg cattaagcag caggttagaa aatattgctg atatccgaaa tgtgacagac 240
atgcccatca tcatggatgc tgatacgggg ggaaaaccag aacattttag ttattacgta 300
aaaagaatga ttaacaacgg tgtaaatggc gtcatcatcg aagataaaac aggattaaag 360
aaaaattctt tgttcggcac tgaagtagaa cagactctcg cagatattaa tgatttttca 420
gagaagatta aaagaggaaa atctgcagtt tatattgatg attttatgat catagccaga 480
cttgaaagtc ttattgcagg gttcgacgta gaacatgcac tcgaacgtgc cgacgcatac 540
gtcgaagccg gggcagacgg aattatgatt catagttgta agaagactcc ggatgaggtt 600
ttcttattca gtacgaaatt tcggaaaaaa tatccatcag taccattaat ttgtgttcct 660
actacttatt ctgcaaccag caacagagaa ctcagtgaag cgggttttaa cgtgatcatt 720

-continued

```
tatgcaaacc atatgctcag ggctgcttat aaagcaatgg aaaatgtttc aaaagaaata    780

ttgagatatg gcaggacggc agagatagaa aaatcttgca tgagtgtaaa ggaaattatt    840

tcactgattc cttaa                                                     855
```

<210> SEQ ID NO 2
<211> LENGTH: 1380
<212> TYPE: DNA
<213> ORGANISM: Pantoea ananatis

<400> SEQUENCE: 2

```
ttgcatgagt gtaaaggaaa ttatttcact gattccttaa agagaatgac catgaaaaaa     60

aaagagatga taataggtgc ctatatatcg tatggaacag gacatcatcc tgcttcatgg    120

cgcgaaagtg gcgtaaatgc agcggcagcg cttgatattg atacgtatgc caatcttgca    180

agagtatgtg agaaaggatt agctgattta ctttttcttg cagatacgcc ttctgtattt    240

caggacaata tggacggtta tggcagcagg gtatctgtac tggagccatt atcattatta    300

tcgtatttag catctcaaac acaaaatatt gggctggttg cgacggcttc aacgacgtac    360

aaacaccctt acaacattgc gagggaattt gcttcgctgg attacattag caaaggaagg    420

gcagggtgga atctggtgac atcctcaaag tcggatgcgg ctaaaaactt tggccttgcc    480

gctcatccag aacattcaaa gcgttatgat atggcctggg aagcatggca ggttatcagt    540

ggtttgtggg acagctggga agacaatgct ttagtaagga ataaaaccag tggacaattc    600

ttcgttaagg ataaataccg ggaaataaat tttgagggtg aatattttaa tgtaaaaggc    660

ccattaaaca tagctcgccc tcctcagggc tatcccgtca tcgtccaggc gggttcctct    720

gaggaaggaa aagagttagc tgcaaaaaca gcagatattg tttttactgc acaaaacaat    780

attgaagatg caaaaaaatt ctatgatgat cttaaagggc gaatggaaaa atacggaagg    840

tcaaagagtg aacttcttat tcttcccgga ttaagctttt atattgcaag tgacgaatct    900

aaagcccgta aaaagcttaa tgatctcaac gcactgatcc ctcaatcatt tggcttaagt    960

atgttatcag atttactggg tggggttgat ttaaaaaaca atgatcctga aggaccatta   1020

ccagatttac cgaaatctaa tggtaatcag agtagacaaa aaattattat cgatttagct   1080

cgaaaagaaa aactatctat caagcaactt tatgaaaaaa taatcatttc aagaggacat   1140

tatacattta caggttccta tcaagattta gcagatgaga tgattaagtg ggttgaaaat   1200

gaagcatgtg atggtttcaa cattatgcct cctctcatgc ctgaatctct tattaatctt   1260

ttcgatcatg tcattccact tattcaggca agaggatggt ataaaaaatc atattctact   1320

ggaacattaa gagaaaaact ggggcttaaa agacctacta ataaattgtt taatcaataa   1380
```

<210> SEQ ID NO 3
<211> LENGTH: 1122
<212> TYPE: DNA
<213> ORGANISM: Pantoea ananatis

<400> SEQUENCE: 3

```
atgcttaata aaaatctgat tcttgaagat accactttac gtgatggtga gcaggcgcca     60

ggtgttgcat ttacaccaga gcaaaaagta gaaatttttt atctacttgc aaatatgggc    120

gttaaatgga tcgaagccgg aatacctgcg atgaagggtg atgaagtaaa ggctctgtcg    180

gaaatgttag agagaaaaaa tgaaattaac atcatcgcgt ggaaccgagg cgtgcttgaa    240

gacattgagt acagtatctc acttggattc aaagcggtgc atatcgggct accgacttca    300
```

-continued

```
gctatccatt tagagaaaag cgttaagaaa gataagtcct ggcttgtaaa gacggcttca    360
gatttagtta agtttgccaa agacaaaggg atgtttgttt ctatcagcgc agaagatata    420
ggccgaacag atattggatt cttacaggag tatgcacagg tagttgctga ggctggagcc    480
gatcgtcttc gcctctctga cacgattggt attctttctc ctgcacaata caaagaaaaa    540
gtctctttgt taaataagaa cgtcaacatc gatttgcagt gccattgcca caatgatttt    600
ggttttgcag ttgctaacac gctggcaggc attgaagcag gagcacgcta ctttcatgtc    660
tgcgtcaatg gcattggtga aagggctgga atgccagacc tggcacaagt tgctatggca    720
ttgcactttt tccacggggt tgatttaggg ctcgatttaa caaaattaat cgcgttgagt    780
gaaacggtcg ccaggtacag ccatcaaaaa atcagtccat ggcagccgat cgtaggcgat    840
aacgtttttg cacatgaatc gggcattcac gcaaatggta tgctcaaaga cagcagtact    900
tttgaaccct tcgacccagc tacggtggga ggagaacgac gtctggtcgt gggtaaacat    960
tccggtcgcg ccattatcaa acattttctc gaagaatcag gcgtgaaagc tgccgacgat   1020
aaggctcttg atcgctgttt agaacgcgtg agaagtcatg ccgtgcgcca ccccggtggg   1080
atccctccac atgtattagt tgatctgtat accgcggggt aa                      1122
```

<210> SEQ ID NO 4
<211> LENGTH: 1239
<212> TYPE: DNA
<213> ORGANISM: Pantoea ananatis

<400> SEQUENCE: 4

```
atgaaaagta atcagccgat tgttaaccag atcattgcgt cacacagtgg cagaggtcag     60
gtttcagcag gtgaactgat cacggtagat gttgactacg tctatgttca ggatggaaat    120
tcaccgaccg tggcaaaact gtttcaggat tatcatctgt ctgaggtgct aaaacccgat    180
aaaatcgggt tcttcttcga ccattcagtt ctggtacctg ataaaaccat ggctaaacgt    240
gtcaacgagg ccatggaatt tgcaaaaaaa cttggaataa acatctattc acgaggggag    300
ggaattagtc acgtcattgc cctggagagt aaaatattta aacccggcaa tatagtgctg    360
ggcgcagatt cccatacttg tacagggggg gccgtacagt ctttagcgct gggaatgggg    420
gcttcggata ttctggttgc tatgttaaca ggacaaacgt ggttgaaagt ccctcaaaca    480
gtccatttgt gtattaaggg taaaacggga aaagatgtgc gggcaaaaga tgtcatgttg    540
gcacttttaa ataagtacgg acaaacacca tttctttata aatcgatcga agtttcaggg    600
gaatgggcag aagagctaac gcttgacgaa gctgcaagtt ttgcaagtat ggctgttgag    660
ttaggagcca aatgcatatt tatgccagat gggcaaggca ggcctgaggg gctattgaag    720
gcggatgcct cagtggcaga cagtgtcatc aatttttctg tatcagaatt aatgccccat    780
atcgcaccac ctcacagtcc tttgtatgct aaacctgcaa atgactttga gggtctgaaa    840
tttgattata ttttcattgg aagctgtact aacagcagac ttgaagatat caaagaggtg    900
gccgaaattg ttgctggtaa aacaatacat cccgatattc actgccttct gacgccagga    960
tcgaaaagtg tttatctaaa agctctccag gcgggatata tcgatacgct tatccgctcg   1020
ggcattattg tcaccccacc gggttgtgga gcttgtgtgg gtacccaagg aaccattcct   1080
gcggatgggg agaaagtatt aagtacgatg aaccgcaatt ttaagggaag aatggggaat   1140
gctgaggcag acatcttttt atgttctcca cgaactgcag cgatggttgc attgaacggc   1200
actgttccac attttgaggg agagtccgca tatgagtaa                          1239
```

<210> SEQ ID NO 5
<211> LENGTH: 564
<212> TYPE: DNA
<213> ORGANISM: Pantoea ananatis

<400> SEQUENCE: 5
ctgttccaca ttttgaggga gagtccgcat atgagtaaaa ctgctgaaaa ttatcgcgtc 60
agacgcgtgg aagggaacat ctcgaccgac gatattatac ctgcgcgcta taaacatatg 120
tataccgagc cggcccagct ggcaccgcat ctttttgaga gccgttttcc cggatttagg 180
gaaacgctca gtatcaatga tgtgcttgta tgtgatcaaa tattcggtat agggagttcg 240
cgggagcagg cagtaacaac tctgttggca tgtggtgtta aatatgtatt ttccccttct 300
ttcgggagga tttttttag gaactcttgg aatttgggtt tacatgcgat tgaggtcgat 360
acgagtgaac ttgcagattt aagtgaaatt aaaatagaac tgactggagg ggtaatttat 420
acagaaaata atcaaataaa ttttttccct cccagctcgc agatgacggc aattgtcagt 480
gcaggtggca taatacccta caccataaat aaaattatgg aaaaaaaagg tgatatttta 540
agaggttata gcaatgaaaa gtga 564

<210> SEQ ID NO 6
<211> LENGTH: 768
<212> TYPE: DNA
<213> ORGANISM: Pantoea ananatis

<400> SEQUENCE: 6
atgaaaagtg aaaagtttga tggtttggct gataactatg ataaatatcg tccccgttat 60
cctgcaatcc ttttcaagga aatccatgac tggatgcagc cgtctgccaa aaatatatac 120
gatattggcg caggcacagg tattgctatt gaaggtatga cacgtgtcac tggaaaacac 180
tatgatttca cggcgataga tatttctgaa gatatgataa aaaaaggaag ggaaaaactg 240
cctggtacga cttgggttaa aggaaaagcg gaagatattc tttctgataa aagccgtatt 300
gacgtcatta tggcggcaca gtccttccaa tggatggata gagctaaaac attagaagtt 360
tcgataaaat ctttaaataa gggcggggtt tttgcagttt tgcaaaacaa tcgagattac 420
agaaataatg aaatgcttaa caaatatgaa ggtttgctag agaaatttag tccaggttac 480
agcagacatt atcgcgacta tgactatgaa aatgaaatca ccaatgtttt taaattgcct 540
attgctaact ttaagaaagt cgtcacaggg tggactatgg aaatgatttc agaagatttt 600
tttggattca tttcttcctc aacccaggta caaagagcta ttgagaacga tcgtaatgga 660
ttctggaagg agattgaaat cttgattgac gaacactcag ttggtggaaa aattagcata 720
gattatataa gtgagttatt tatagctaag aagcgtgatg attcatag 768

<210> SEQ ID NO 7
<211> LENGTH: 477
<212> TYPE: DNA
<213> ORGANISM: Pantoea ananatis

<400> SEQUENCE: 7
atgattcata gcatgacgat tcaggacatc agcattgaac aagcttcgta tgaagatgcg 60
aagctgttaa gaaaggcttt agaaaaagtt tacgaacctt atacactgaa tttctcacct 120
accgctttgc agtttactga aaatatcatt gctcaggaat cctcgaagtg gctagtcgcg 180
aaatacaagt cagacattgt gggggcagtg agatatgaac tttatgatat ttatctggac 240
ttccattttc tctgcgtcac accaccattc agaaaaatgg gagtagggaa tgaattattt 300

-continued

```
cataaactga agaaaatagc gtatgaaaaa agaaaggatt ttatgaagat cgttttgcga    360

gattcgctaa gctataaccg acgctatttt gaaagtaaag gattttactt ttatcataaa    420

taccagacaa atatgcatag tgtatttatt ttaaaattaa acggtgaaaa gccatga      477


<210> SEQ ID NO 8
<211> LENGTH: 1104
<212> TYPE: DNA
<213> ORGANISM: Pantoea ananatis

<400> SEQUENCE: 8

atgaataaaa aagcattggt tattgggttg aaaagtaata tggaaagagt catcaaaggg     60

ctcaatgaga tagaatttat tattattgac agaggaacac tggataacga aagtatagat    120

tatatcatta atctttcaga tgatttaatg cataaaaaat cattcagtta tgttatagcc    180

agttctgagg attttatcgc tttggctggg ttattgcgta atcgttattc actttatggt    240

gaaaaatatt ataaaagtac aattgcaacc aataaattcc tgatgcgtaa tttttgctca    300

ggttttttat cctgtccaaa gttctggcta tcaggtgaga tcatcaattc agagaatctt    360

ttactgtcat cccagaaaga ttacatcgta aaacctctta caggtagttc tgcaaaacat    420

gtcgaaacag tcacacagga agacttaaac caatatctta atgaaaataa caaattgatg    480

ttaattgaag aaaaggtttt aatgagagat gaatatcatc ttgattgtat aatcaaagac    540

ggtaatatcc tcttttcaac actgtcaatt tacgacaggc ctatactcga ggcaaaaagt    600

aaaaacagag ccagtatcaa cttacccgat ggcacacggc ttcatgaaga tgccttaata    660

cttgccacga atttgcaaag tcattttgaa atgactaatg gcgtttttca tattgaaatg    720

tatcatactc aggatggatt tatactcggt gagtttggta tccgccctcc cggagcgggt    780

gtgaccgata tgtattatat gtatagaggc gtcgatttct gggaggcatt tatttattct    840

cagattgata aagaatttat tttacccccta aatcataagt ccgataaata ttgtgctgct    900

attgggatat gttcttcttt cccggtcgat gatatcagaa gtacgtcaaa agtatccgtg    960

gataaatatg taaatttgcg tgagaatgct gctaaacccg cagttcccag ttcaacgtct   1020

tttaatcata tgatttatgt ttcttcatca tccttagaag aaataaggaa tttttttgcat   1080

gatatttctg acagacaaga gtaa                                          1104


<210> SEQ ID NO 9
<211> LENGTH: 1239
<212> TYPE: DNA
<213> ORGANISM: Pantoea ananatis

<400> SEQUENCE: 9

atgttaaaat atgaaaccaa aaaaaacgct ttcttccaga tatacaattt tctttcatgc     60

tcggctgaag ggattcagac ggttatattt ttgtggctta tatatcatga aactcatagt    120

ccgatgcttg tcagtctgac tatagtttct tcatatcttc catcagccgt attaggattc    180

tttttcctca aaaaagctga tgcgagcagt cctggaaaac agttatttat cagtaatgtt    240

tctcttagtg ccatatcgct aattgtctat tttattttaa tgagaaatga gggttttgaa    300

ctaatcacgc tcagtatctt ttatttggca caggccgtat tatctgttgt caaaatgttt    360

aataagacat cccaaaatcg cattatcaga acagcattca gtaatagtga tgcaataaaa    420

gcacttcagc ttgcctcctc tggcatgcag gccgctcagg tttttggcgc ggccatagga    480

ggatgggcta tcagtacggg ttactacatg caagcgctca tgctgacctg ctgcatctac    540

cttttgaata tttatatttc gacacttttt gagaaaggga atcctgataa taaagacgct    600
```

-continued gaggttattg tgcagattca ctctgtcact aagaaaaatg aatcctttac atatcttttt 660
cgcagtaagg actttttgtt acccttgatt tttactgttc catcaagtgg agctttacaa 720
tttttaaaca catcccttcc ttcattatct tctctatatg gtaatagcga gaaaatttat 780
ccagtgctga atatgactct acaatgtgct gtcattatct cggggatagc agcagcactc 840
aatatgcttt ctctaaagtc ttcattacgg ttttctctgt gtatttctgg catctgtctg 900
attttgatgt gtttatcatc gagaaattat tatgccgtat actttttttt atttctcact 960
tctttttttg tttcatggca tatgatttct attaaggtac tcacgaatca aatgcctgat 1020
atagaaaata ttggtaaatt cacaatgatg agaaactcag tcgcttctgg tgtgaaaatt 1080
gtcttttcta tttcgtctgg tgcttttttg actttttaca gcataactac aacttatcta 1140
atacttgcga tactgcttat ttttttcaat gtactatggg tttgtcagag tcgcagtttt 1200
aactatgagg atttaggtga tgttaaattt caaaagtga 1239

<210> SEQ ID NO 10
<211> LENGTH: 1008
<212> TYPE: DNA
<213> ORGANISM: Pantoea ananatis

<400> SEQUENCE: 10
atgttaaatt tcaaaagtga tttttctgaa tttattactg gtttttatct taaacagttt 60
actcatttaa atacgcagga aagagaacat gtgcttgaaa cgcttggcgt cacacccagc 120
gcaatcaatg agtttataac atcagaagat atttatatta ccttacctca tgcaagtatg 180
aatgtttttt ttccaagagc gggggtctca cgttatgtct acgatctaca aaatagtaac 240
aaaaacgcgt tccatttaag gtttttcttg acccatacca actttagcga tctgaactgg 300
cgcccttatg catggtggtt taataacggc gggaaaatag ataaacttac ctttttcaca 360
cgaaataaaa aaaagaaaca taatatcgtt tactcgctaa aaccaaatga aatgcactct 420
gcctctgtag atcgacgtct gcgtcatgac tttgatacaa gtatgaagtt taaacgtatt 480
tctcttagct tcatctatat gacagccgtt caagaggtca atagcggttt tgcacataaa 540
ggccgtaccc tttatctccc acttgacgca tttgtagctt ttattattca tcaggcaaaa 600
aacgatgtta tatcttttaa ttttttagaa gctttttaa gccaggcaca atgcagaaga 660
ctgaatggcg aagaattgag ttttaccagt gaatggcgcg atgcatttat ctttgataat 720
tttacaaaca ttgcgctgtt aaattttttt cagcctgcag catttgtggg aggcgaaaaa 780
atggataact actggcatca ggtgattgaa aaatggaaaa tggcattacc aaatcaatct 840
gaagttgagt ttgcgttacc cactaatctg gtcatgcctg ccgttcaaga gtatatttac 900
ccttataaac catcaagcga tatagcagaa cagcttatta aaaataacat cccatacagt 960
cttaccatgg ctattcagga acatgatctt ttttcaaaga aagaataa 1008

<210> SEQ ID NO 11
<211> LENGTH: 480
<212> TYPE: DNA
<213> ORGANISM: Pantoea ananatis

<400> SEQUENCE: 11
atgctagata aaagtgcttt tcgccacgca atgtcgcatc ttcctactgc agtcactatt 60
gtaacatcaa gcggctcctg cggggctgca gcatgtacag tttcatccgt gtgttctgtc 120
accgacgacc cacccacttt actcgtatgt ataaatcgtg cctccaataa caatagtgtt 180

-continued ataagaaata atggctcttt gtgtgtcagc attctttcag gagagcaaag caacattgca 240
atgcaatgtg ctaatcatca ggtttcagtt gaggagcgct tagcattatt cgacgcagac 300
gttctggtca cggggtctcc tgctgtagtt gattccgttt gctgtttaga ttgtcgtgta 360
gataatattg tggaatcagg aacccactct gtcttctttt gtcaggttct ttcttctaaa 420
gcttttgtgg ggaaagatgc gctggtttat tattgccgga attatcatcg tgtatcataa 480

<210> SEQ ID NO 12
<211> LENGTH: 1155
<212> TYPE: DNA
<213> ORGANISM: Pantoea ananatis

<400> SEQUENCE: 12
atgatgaaaa gtttaattat tacgtcgcat tttaatagtg atttatcctc tatggcatgc 60
gatgagtttg gattaaaaag atcactaatt ttctatactc caaaaataaa tgaacttagc 120
ttaggtttaa aatatgagta ctacgataag atagattctt actctgtaag attaatggag 180
cttgggaatg aaattgattt tatatggagc acttccggtt ctgaaatcaa ctcgttcgct 240
gaattaaaag ctgttgagtt ggcaggatta agaaacatct atctaggcat gaatgaaaat 300
gctttttcta cagctgctta taaaagcatc acgcaagagt taatggcatt tttgggtgtt 360
agtattccca aagggcttca atgtaacaca aaaaaagaaa tacatgattt ccttgaatat 420
aatggtggaa ctatagtctg taaagctaac aatggagcag gtggtgtaaa tcaattttat 480
tgccaaagat ttgatgacat atataaactc cctcatgagg taactgattg gtatgtagaa 540
cagtttctga aaggacttga gttttctgta aacgcttata tgctaaatgg gttttatata 600
gcctccccga taatgtttaa aggcgaaact gatattcata gcgggcacgc aatggacaaa 660
ttcaggtata ttagcaagct aaaaaataaa agcttaaatg aaaaaataaa tgccatatta 720
agtaaaatta gtaataccaa tatctttaat ggatggatag aggttgagtt tataaaaaca 780
catcaggatt tggtagttat agaaattaat gcgaggtata atggaacaat cagagctact 840
ggatatgctt gtaatgaaaa tttatatcaa ttggatttgg aaagtaaaat ttataataaa 900
ttttcttcac aattaaatca tgaaaacgaa gtcattgaga tgccaattca tttgaaactt 960
gaaacaggtt taaaagaatt tggtttcgtc caaaaaatga aatctcgaaa aaccaacaca 1020
ggaagggcca caatatgggg tgaagatcaa tgtgaactat tagagaggat caaaaatact 1080
gaattagaaa tatactcaga aagaattatt catggcataa atgagagtaa ggagttattc 1140
gaaaaatata tttaa 1155

<210> SEQ ID NO 13
<211> LENGTH: 658
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
gcgcaacgca attaatgtga gttagctcac tcattaggca ccccaggctt tacactttat 60
gcttccgggt tttctttgcc tcacgatcgc ccccaaaaca cataaccaat tgtatttatt 120
gaaaaataaa tagatacaac tcactaaaca tagcaattca gatccggtcc agtaatgacc 180
tcagaactcc atctggattt gttcagaacg ctcggttgcc gccgggcgtt ttttattggt 240
gagaatcgca gcaacttgtc gcgccaatcg agccatgtcg tcgtcaacga ccccccattc 300

-continued

```
aagaacagca agcagcattg agaactttgg aatccagtcc ctcttccacc tgctgatccg    360

gatcgatccc gttatcgact gcacggtgca ccaatgcttc tggcgtcagg cagccatcgg    420

aagctgtggt atggctgtgc aggtcgtaaa tcactgcata attcgtgtcg ctcaaggcgc    480

actcccgttc tggataatgt tttttgcgcc gacatcataa cggttctggc aaatattctg    540

aaatgagctg ttgacaatta atcatcggct cgtataatgt gtggaattgt gagcggataa    600

caatttcaca caggaaacag aattgatccg gccaagcttg taagaaggag atatacat      658


<210> SEQ ID NO 14
<211> LENGTH: 284
<212> TYPE: PRT
<213> ORGANISM: Pantoea ananatis

<400> SEQUENCE: 14

Met Ile Lys Lys Leu Ile Ala Glu Lys Gly Thr Leu Ile Phe Ile Glu
1               5                   10                  15

Ala His Asn Pro Leu Ser Ala Leu Ile Ala Ser Lys Ala Glu Gln Thr
            20                  25                  30

Asn Ser Glu Gly Arg Ile Val Lys Phe Asp Gly Ile Trp Ser Ser Ser
        35                  40                  45

Leu Thr Asp Ser Ala Ser Arg Gly Ile Pro Asp Asn Glu Thr Leu Ala
    50                  55                  60

Leu Ser Ser Arg Leu Glu Asn Ile Ala Asp Ile Arg Asn Val Thr Asp
65                  70                  75                  80

Met Pro Ile Ile Met Asp Ala Asp Thr Gly Gly Lys Pro Glu His Phe
                85                  90                  95

Ser Tyr Tyr Val Lys Arg Met Ile Asn Asn Gly Val Asn Gly Val Ile
            100                 105                 110

Ile Glu Asp Lys Thr Gly Leu Lys Lys Asn Ser Leu Phe Gly Thr Glu
        115                 120                 125

Val Glu Gln Thr Leu Ala Asp Ile Asn Asp Phe Ser Glu Lys Ile Lys
    130                 135                 140

Arg Gly Lys Ser Ala Val Tyr Ile Asp Asp Phe Met Ile Ile Ala Arg
145                 150                 155                 160

Leu Glu Ser Leu Ile Ala Gly Phe Asp Val Glu His Ala Leu Glu Arg
                165                 170                 175

Ala Asp Ala Tyr Val Glu Ala Gly Ala Asp Gly Ile Met Ile His Ser
            180                 185                 190

Cys Lys Lys Thr Pro Asp Glu Val Phe Leu Phe Ser Thr Lys Phe Arg
        195                 200                 205

Lys Lys Tyr Pro Ser Val Pro Leu Ile Cys Val Pro Thr Thr Tyr Ser
    210                 215                 220

Ala Thr Ser Asn Arg Glu Leu Ser Glu Ala Gly Phe Asn Val Ile Ile
225                 230                 235                 240

Tyr Ala Asn His Met Leu Arg Ala Ala Tyr Lys Ala Met Glu Asn Val
                245                 250                 255

Ser Lys Glu Ile Leu Arg Tyr Gly Arg Thr Ala Glu Ile Glu Lys Ser
            260                 265                 270

Cys Met Ser Val Lys Glu Ile Ile Ser Leu Ile Pro
        275                 280


<210> SEQ ID NO 15
<211> LENGTH: 459
<212> TYPE: PRT
<213> ORGANISM: Pantoea ananatis
```

-continued

<400> SEQUENCE: 15

Met His Glu Cys Lys Gly Asn Tyr Phe Thr Asp Ser Leu Lys Arg Met
1               5                   10                  15

Thr Met Lys Lys Lys Glu Met Ile Ile Gly Ala Tyr Ile Ser Tyr Gly
            20                  25                  30

Thr Gly His His Pro Ala Ser Trp Arg Glu Ser Gly Val Asn Ala Ala
        35                  40                  45

Ala Ala Leu Asp Ile Asp Thr Tyr Ala Asn Leu Ala Arg Val Cys Glu
    50                  55                  60

Lys Gly Leu Ala Asp Leu Leu Phe Leu Ala Asp Thr Pro Ser Val Phe
65                  70                  75                  80

Gln Asp Asn Met Asp Gly Tyr Gly Ser Arg Val Ser Val Leu Glu Pro
                85                  90                  95

Leu Ser Leu Leu Ser Tyr Leu Ala Ser Gln Thr Gln Asn Ile Gly Leu
            100                 105                 110

Val Ala Thr Ala Ser Thr Thr Tyr Lys His Pro Tyr Asn Ile Ala Arg
        115                 120                 125

Glu Phe Ala Ser Leu Asp Tyr Ile Ser Lys Gly Arg Ala Gly Trp Asn
    130                 135                 140

Leu Val Thr Ser Ser Lys Ser Asp Ala Ala Lys Asn Phe Gly Leu Ala
145                 150                 155                 160

Ala His Pro Glu His Ser Lys Arg Tyr Asp Met Ala Trp Glu Ala Trp
                165                 170                 175

Gln Val Ile Ser Gly Leu Trp Asp Ser Trp Glu Asp Asn Ala Leu Val
            180                 185                 190

Arg Asn Lys Thr Ser Gly Gln Phe Phe Val Lys Asp Lys Tyr Arg Glu
        195                 200                 205

Ile Asn Phe Glu Gly Glu Tyr Phe Asn Val Lys Gly Pro Leu Asn Ile
    210                 215                 220

Ala Arg Pro Pro Gln Gly Tyr Pro Val Ile Val Gln Ala Gly Ser Ser
225                 230                 235                 240

Glu Glu Gly Lys Glu Leu Ala Ala Lys Thr Ala Asp Ile Val Phe Thr
                245                 250                 255

Ala Gln Asn Asn Ile Glu Asp Ala Lys Lys Phe Tyr Asp Asp Leu Lys
            260                 265                 270

Gly Arg Met Glu Lys Tyr Gly Arg Ser Lys Ser Glu Leu Leu Ile Leu
        275                 280                 285

Pro Gly Leu Ser Phe Tyr Ile Ala Ser Asp Glu Ser Lys Ala Arg Lys
    290                 295                 300

Lys Leu Asn Asp Leu Asn Ala Leu Ile Pro Gln Ser Phe Gly Leu Ser
305                 310                 315                 320

Met Leu Ser Asp Leu Leu Gly Gly Val Asp Leu Lys Asn Asn Asp Pro
                325                 330                 335

Glu Gly Pro Leu Pro Asp Leu Pro Lys Ser Asn Gly Asn Gln Ser Arg
            340                 345                 350

Gln Lys Ile Ile Ile Asp Leu Ala Arg Lys Glu Lys Leu Ser Ile Lys
        355                 360                 365

Gln Leu Tyr Glu Lys Ile Ile Ile Ser Arg Gly His Tyr Thr Phe Thr
    370                 375                 380

Gly Ser Tyr Gln Asp Leu Ala Asp Glu Met Ile Lys Trp Val Glu Asn
385                 390                 395                 400

Glu Ala Cys Asp Gly Phe Asn Ile Met Pro Pro Leu Met Pro Glu Ser

```
                405                 410                 415

Leu Ile Asn Leu Phe Asp His Val Ile Pro Leu Ile Gln Ala Arg Gly
            420                 425                 430

Trp Tyr Lys Lys Ser Tyr Ser Thr Gly Thr Leu Arg Glu Lys Leu Gly
        435                 440                 445

Leu Lys Arg Pro Thr Asn Lys Leu Phe Asn Gln
    450                 455


<210> SEQ ID NO 16
<211> LENGTH: 373
<212> TYPE: PRT
<213> ORGANISM: Pantoea ananatis

<400> SEQUENCE: 16

Met Leu Asn Lys Asn Leu Ile Leu Glu Asp Thr Thr Leu Arg Asp Gly
1               5                   10                  15

Glu Gln Ala Pro Gly Val Ala Phe Thr Pro Glu Gln Lys Val Glu Ile
            20                  25                  30

Phe Tyr Leu Leu Ala Asn Met Gly Val Lys Trp Ile Glu Ala Gly Ile
        35                  40                  45

Pro Ala Met Lys Gly Asp Glu Val Lys Ala Leu Ser Glu Met Leu Glu
    50                  55                  60

Arg Lys Asn Glu Ile Asn Ile Ile Ala Trp Asn Arg Gly Val Leu Glu
65                  70                  75                  80

Asp Ile Glu Tyr Ser Ile Ser Leu Gly Phe Lys Ala Val His Ile Gly
                85                  90                  95

Leu Pro Thr Ser Ala Ile His Leu Glu Lys Ser Val Lys Lys Asp Lys
            100                 105                 110

Ser Trp Leu Val Lys Thr Ala Ser Asp Leu Val Lys Phe Ala Lys Asp
        115                 120                 125

Lys Gly Met Phe Val Ser Ile Ser Ala Glu Asp Ile Gly Arg Thr Asp
    130                 135                 140

Ile Gly Phe Leu Gln Glu Tyr Ala Gln Val Val Ala Glu Ala Gly Ala
145                 150                 155                 160

Asp Arg Leu Arg Leu Ser Asp Thr Ile Gly Ile Leu Ser Pro Ala Gln
                165                 170                 175

Tyr Lys Glu Lys Val Ser Leu Leu Asn Lys Asn Val Asn Ile Asp Leu
            180                 185                 190

Gln Cys His Cys His Asn Asp Phe Gly Phe Ala Val Ala Asn Thr Leu
        195                 200                 205

Ala Gly Ile Glu Ala Gly Ala Arg Tyr Phe His Val Cys Val Asn Gly
    210                 215                 220

Ile Gly Glu Arg Ala Gly Met Pro Asp Leu Ala Gln Val Ala Met Ala
225                 230                 235                 240

Leu His Phe Phe His Gly Val Asp Leu Gly Leu Asp Leu Thr Lys Leu
                245                 250                 255

Ile Ala Leu Ser Glu Thr Val Ala Arg Tyr Ser His Gln Lys Ile Ser
            260                 265                 270

Pro Trp Gln Pro Ile Val Gly Asp Asn Val Phe Ala His Glu Ser Gly
        275                 280                 285

Ile His Ala Asn Gly Met Leu Lys Asp Ser Ser Thr Phe Glu Pro Phe
    290                 295                 300

Asp Pro Ala Thr Val Gly Gly Glu Arg Arg Leu Val Val Gly Lys His
305                 310                 315                 320
```

-continued

```
Ser Gly Arg Ala Ile Ile Lys His Phe Leu Glu Glu Ser Gly Val Lys
                325                 330                 335

Ala Ala Asp Asp Lys Ala Leu Asp Arg Cys Leu Glu Arg Val Arg Ser
            340                 345                 350

His Ala Val Arg His Pro Gly Gly Ile Pro Pro His Val Leu Val Asp
        355                 360                 365

Leu Tyr Thr Ala Gly
    370


<210> SEQ ID NO 17
<211> LENGTH: 412
<212> TYPE: PRT
<213> ORGANISM: Pantoea ananatis

<400> SEQUENCE: 17

Met Lys Ser Asn Gln Pro Ile Val Asn Gln Ile Ile Ala Ser His Ser
1               5                   10                  15

Gly Arg Gly Gln Val Ser Ala Gly Glu Leu Ile Thr Val Asp Val Asp
            20                  25                  30

Tyr Val Tyr Val Gln Asp Gly Asn Ser Pro Thr Val Ala Lys Leu Phe
        35                  40                  45

Gln Asp Tyr His Leu Ser Glu Val Leu Lys Pro Asp Lys Ile Gly Phe
    50                  55                  60

Phe Phe Asp His Ser Val Leu Val Pro Asp Lys Thr Met Ala Lys Arg
65                  70                  75                  80

Val Asn Glu Ala Met Glu Phe Ala Lys Lys Leu Gly Ile Asn Ile Tyr
                85                  90                  95

Ser Arg Gly Glu Gly Ile Ser His Val Ile Ala Leu Glu Ser Lys Ile
            100                 105                 110

Phe Lys Pro Gly Asn Ile Val Leu Gly Ala Asp Ser His Thr Cys Thr
        115                 120                 125

Gly Gly Ala Val Gln Ser Leu Ala Leu Gly Met Gly Ala Ser Asp Ile
    130                 135                 140

Leu Val Ala Met Leu Thr Gly Gln Thr Trp Leu Lys Val Pro Gln Thr
145                 150                 155                 160

Val His Leu Cys Ile Lys Gly Lys Thr Gly Lys Asp Val Arg Ala Lys
                165                 170                 175

Asp Val Met Leu Ala Leu Leu Asn Lys Tyr Gly Gln Thr Pro Phe Leu
            180                 185                 190

Tyr Lys Ser Ile Glu Val Ser Gly Glu Trp Ala Glu Glu Leu Thr Leu
        195                 200                 205

Asp Glu Ala Ala Ser Phe Ala Ser Met Ala Val Glu Leu Gly Ala Lys
    210                 215                 220

Cys Ile Phe Met Pro Asp Gly Gln Gly Arg Pro Glu Gly Leu Leu Lys
225                 230                 235                 240

Ala Asp Ala Ser Val Ala Asp Ser Val Ile Asn Phe Ser Val Ser Glu
                245                 250                 255

Leu Met Pro His Ile Ala Pro Pro His Ser Pro Leu Tyr Ala Lys Pro
            260                 265                 270

Ala Asn Asp Phe Glu Gly Leu Lys Phe Asp Tyr Ile Phe Ile Gly Ser
        275                 280                 285

Cys Thr Asn Ser Arg Leu Glu Asp Ile Lys Glu Val Ala Glu Ile Val
    290                 295                 300

Ala Gly Lys Thr Ile His Pro Asp Ile His Cys Leu Leu Thr Pro Gly
305                 310                 315                 320
```

```
Ser Lys Ser Val Tyr Leu Lys Ala Leu Gln Ala Gly Tyr Ile Asp Thr
                325                 330                 335

Leu Ile Arg Ser Gly Ile Ile Val Thr Pro Pro Gly Cys Gly Ala Cys
            340                 345                 350

Val Gly Thr Gln Gly Thr Ile Pro Ala Asp Gly Glu Lys Val Leu Ser
        355                 360                 365

Thr Met Asn Arg Asn Phe Lys Gly Arg Met Gly Asn Ala Glu Ala Asp
    370                 375                 380

Ile Phe Leu Cys Ser Pro Arg Thr Ala Ala Met Val Ala Leu Asn Gly
385                 390                 395                 400

Thr Val Pro His Phe Glu Gly Glu Ser Ala Tyr Glu
                405                 410
```

<210> SEQ ID NO 18
<211> LENGTH: 187
<212> TYPE: PRT
<213> ORGANISM: Pantoea ananatis

<400> SEQUENCE: 18

```
Met Phe His Ile Leu Arg Glu Ser Pro His Met Ser Lys Thr Ala Glu
1               5                   10                  15

Asn Tyr Arg Val Arg Arg Val Glu Gly Asn Ile Ser Thr Asp Asp Ile
            20                  25                  30

Ile Pro Ala Arg Tyr Lys His Met Tyr Thr Glu Pro Ala Gln Leu Ala
        35                  40                  45

Pro His Leu Phe Glu Ser Arg Phe Pro Gly Phe Arg Glu Thr Leu Ser
    50                  55                  60

Ile Asn Asp Val Leu Val Cys Asp Gln Ile Phe Gly Ile Gly Ser Ser
65                  70                  75                  80

Arg Glu Gln Ala Val Thr Thr Leu Leu Ala Cys Gly Val Lys Tyr Val
                85                  90                  95

Phe Ser Pro Ser Phe Gly Arg Ile Phe Phe Arg Asn Ser Trp Asn Leu
            100                 105                 110

Gly Leu His Ala Ile Glu Val Asp Thr Ser Glu Leu Ala Asp Leu Ser
        115                 120                 125

Glu Ile Lys Ile Glu Leu Thr Gly Gly Val Ile Tyr Thr Glu Asn Asn
    130                 135                 140

Gln Ile Asn Phe Phe Pro Pro Ser Ser Gln Met Thr Ala Ile Val Ser
145                 150                 155                 160

Ala Gly Gly Ile Ile Pro Tyr Thr Ile Asn Lys Ile Met Glu Lys Lys
                165                 170                 175

Gly Asp Ile Leu Arg Gly Tyr Ser Asn Glu Lys
            180                 185
```

<210> SEQ ID NO 19
<211> LENGTH: 255
<212> TYPE: PRT
<213> ORGANISM: Pantoea ananatis

<400> SEQUENCE: 19

```
Met Lys Ser Glu Lys Phe Asp Gly Leu Ala Asp Asn Tyr Asp Lys Tyr
1               5                   10                  15

Arg Pro Arg Tyr Pro Ala Ile Leu Phe Lys Glu Ile His Asp Trp Met
            20                  25                  30

Gln Pro Ser Ala Lys Asn Ile Tyr Asp Ile Gly Ala Gly Thr Gly Ile
        35                  40                  45
```

-continued

```
Ala Ile Glu Gly Met Thr Arg Val Thr Gly Lys His Tyr Asp Phe Thr
    50                  55                  60

Ala Ile Asp Ile Ser Glu Asp Met Ile Lys Lys Gly Arg Glu Lys Leu
65                  70                  75                  80

Pro Gly Thr Thr Trp Val Lys Gly Lys Ala Glu Asp Ile Leu Ser Asp
                85                  90                  95

Lys Ser Arg Ile Asp Val Ile Met Ala Ala Gln Ser Phe Gln Trp Met
            100                 105                 110

Asp Arg Ala Lys Thr Leu Glu Val Ser Ile Lys Ser Leu Asn Lys Gly
        115                 120                 125

Gly Val Phe Ala Val Leu Gln Asn Asn Arg Asp Tyr Arg Asn Asn Glu
    130                 135                 140

Met Leu Asn Lys Tyr Glu Gly Leu Leu Glu Lys Phe Ser Pro Gly Tyr
145                 150                 155                 160

Ser Arg His Tyr Arg Asp Tyr Asp Tyr Glu Asn Glu Ile Thr Asn Val
                165                 170                 175

Phe Lys Leu Pro Ile Ala Asn Phe Lys Lys Val Val Thr Gly Trp Thr
            180                 185                 190

Met Glu Met Ile Ser Glu Asp Phe Phe Gly Phe Ile Ser Ser Ser Thr
        195                 200                 205

Gln Val Gln Arg Ala Ile Glu Asn Asp Arg Asn Gly Phe Trp Lys Glu
    210                 215                 220

Ile Glu Ile Leu Ile Asp Glu His Ser Val Gly Gly Lys Ile Ser Ile
225                 230                 235                 240

Asp Tyr Ile Ser Glu Leu Phe Ile Ala Lys Lys Arg Asp Asp Ser
                245                 250                 255


<210> SEQ ID NO 20
<211> LENGTH: 158
<212> TYPE: PRT
<213> ORGANISM: Pantoea ananatis

<400> SEQUENCE: 20

Met Ile His Ser Met Thr Ile Gln Asp Ile Ser Ile Glu Gln Ala Ser
1               5                   10                  15

Tyr Glu Asp Ala Lys Leu Leu Arg Lys Ala Leu Glu Lys Val Tyr Glu
            20                  25                  30

Pro Tyr Thr Leu Asn Phe Ser Pro Thr Ala Leu Gln Phe Thr Glu Asn
        35                  40                  45

Ile Ile Ala Gln Glu Ser Ser Lys Trp Leu Val Ala Lys Tyr Lys Ser
    50                  55                  60

Asp Ile Val Gly Ala Val Arg Tyr Glu Leu Tyr Asp Ile Tyr Leu Asp
65                  70                  75                  80

Phe His Phe Leu Cys Val Thr Pro Pro Phe Arg Lys Met Gly Val Gly
                85                  90                  95

Asn Glu Leu Phe His Lys Leu Lys Lys Ile Ala Tyr Glu Lys Arg Lys
            100                 105                 110

Asp Phe Met Lys Ile Val Leu Arg Asp Ser Leu Ser Tyr Asn Arg Arg
        115                 120                 125

Tyr Phe Glu Ser Lys Gly Phe Tyr Phe Tyr His Lys Tyr Gln Thr Asn
    130                 135                 140

Met His Ser Val Phe Ile Leu Lys Leu Asn Gly Glu Lys Pro
145                 150                 155
```

-continued

<210> SEQ ID NO 21
<211> LENGTH: 367
<212> TYPE: PRT
<213> ORGANISM: Pantoea ananatis

<400> SEQUENCE: 21

```
Met Asn Lys Lys Ala Leu Val Ile Gly Leu Lys Ser Asn Met Glu Arg
1               5                   10                  15

Val Ile Lys Gly Leu Asn Glu Ile Glu Phe Ile Ile Ile Asp Arg Gly
            20                  25                  30

Thr Leu Asp Asn Glu Ser Ile Asp Tyr Ile Ile Asn Leu Ser Asp Asp
        35                  40                  45

Leu Met His Lys Lys Ser Phe Ser Tyr Val Ile Ala Ser Ser Glu Asp
    50                  55                  60

Phe Ile Ala Leu Ala Gly Leu Leu Arg Asn Arg Tyr Ser Leu Tyr Gly
65                  70                  75                  80

Glu Lys Tyr Tyr Lys Ser Thr Ile Ala Thr Asn Lys Phe Leu Met Arg
                85                  90                  95

Asn Phe Cys Ser Gly Phe Leu Ser Cys Pro Lys Phe Trp Leu Ser Gly
            100                 105                 110

Glu Ile Ile Asn Ser Glu Asn Leu Leu Leu Ser Ser Gln Lys Asp Tyr
        115                 120                 125

Ile Val Lys Pro Leu Thr Gly Ser Ser Ala Lys His Val Glu Thr Val
    130                 135                 140

Thr Gln Glu Asp Leu Asn Gln Tyr Leu Asn Glu Asn Asn Lys Leu Met
145                 150                 155                 160

Leu Ile Glu Glu Lys Val Leu Met Arg Asp Glu Tyr His Leu Asp Cys
                165                 170                 175

Ile Ile Lys Asp Gly Asn Ile Leu Phe Ser Thr Leu Ser Ile Tyr Asp
            180                 185                 190

Arg Pro Ile Leu Glu Ala Lys Ser Lys Asn Arg Ala Ser Ile Asn Leu
        195                 200                 205

Pro Asp Gly Thr Arg Leu His Glu Asp Ala Leu Ile Leu Ala Thr Asn
    210                 215                 220

Leu Gln Ser His Phe Glu Met Thr Asn Gly Val Phe His Ile Glu Met
225                 230                 235                 240

Tyr His Thr Gln Asp Gly Phe Ile Leu Gly Glu Phe Gly Ile Arg Pro
                245                 250                 255

Pro Gly Ala Gly Val Thr Asp Met Tyr Tyr Met Tyr Arg Gly Val Asp
            260                 265                 270

Phe Trp Glu Ala Phe Ile Tyr Ser Gln Ile Asp Lys Glu Phe Ile Leu
        275                 280                 285

Pro Leu Asn His Lys Ser Asp Lys Tyr Cys Ala Ala Ile Gly Ile Cys
    290                 295                 300

Ser Ser Phe Pro Val Asp Asp Ile Arg Ser Thr Ser Lys Val Ser Val
305                 310                 315                 320

Asp Lys Tyr Val Asn Leu Arg Glu Asn Ala Ala Lys Pro Ala Val Pro
                325                 330                 335

Ser Ser Thr Ser Phe Asn His Met Ile Tyr Val Ser Ser Ser Ser Leu
            340                 345                 350

Glu Glu Ile Arg Asn Phe Leu His Asp Ile Ser Asp Arg Gln Glu
        355                 360                 365
```

<210> SEQ ID NO 22
<211> LENGTH: 412

<212> TYPE: PRT
<213> ORGANISM: Pantoea ananatis

<400> SEQUENCE: 22

```
Met Leu Lys Tyr Glu Thr Lys Lys Asn Ala Phe Phe Gln Ile Tyr Asn
1               5                   10                  15

Phe Leu Ser Cys Ser Ala Glu Gly Ile Gln Thr Val Ile Phe Leu Trp
            20                  25                  30

Leu Ile Tyr His Glu Thr His Ser Pro Met Leu Val Ser Leu Thr Ile
        35                  40                  45

Val Ser Ser Tyr Leu Pro Ser Ala Val Leu Gly Phe Phe Phe Leu Lys
    50                  55                  60

Lys Ala Asp Ala Ser Ser Pro Gly Lys Gln Leu Phe Ile Ser Asn Val
65                  70                  75                  80

Ser Leu Ser Ala Ile Ser Leu Ile Val Tyr Phe Ile Leu Met Arg Asn
                85                  90                  95

Glu Gly Phe Glu Leu Ile Thr Leu Ser Ile Phe Tyr Leu Ala Gln Ala
            100                 105                 110

Val Leu Ser Val Val Lys Met Phe Asn Lys Thr Ser Gln Asn Arg Ile
        115                 120                 125

Ile Arg Thr Ala Phe Ser Asn Ser Asp Ala Ile Lys Ala Leu Gln Leu
    130                 135                 140

Ala Ser Ser Gly Met Gln Ala Ala Gln Val Phe Gly Ala Ala Ile Gly
145                 150                 155                 160

Gly Trp Ala Ile Ser Thr Gly Tyr Tyr Met Gln Ala Leu Met Leu Thr
                165                 170                 175

Cys Cys Ile Tyr Leu Leu Asn Ile Tyr Ile Ser Thr Leu Phe Glu Lys
            180                 185                 190

Gly Asn Pro Asp Asn Lys Asp Ala Glu Val Ile Val Gln Ile His Ser
        195                 200                 205

Val Thr Lys Lys Asn Glu Ser Phe Thr Tyr Leu Phe Arg Ser Lys Asp
    210                 215                 220

Phe Leu Leu Pro Leu Ile Phe Thr Val Pro Ser Ser Gly Ala Leu Gln
225                 230                 235                 240

Phe Leu Asn Thr Ser Leu Pro Ser Leu Ser Ser Leu Tyr Gly Asn Ser
                245                 250                 255

Glu Lys Ile Tyr Pro Val Leu Asn Met Thr Leu Gln Cys Ala Val Ile
            260                 265                 270

Ile Ser Gly Ile Ala Ala Ala Leu Asn Met Leu Ser Leu Lys Ser Ser
        275                 280                 285

Leu Arg Phe Ser Leu Cys Ile Ser Gly Ile Cys Leu Ile Leu Met Cys
    290                 295                 300

Leu Ser Ser Arg Asn Tyr Tyr Ala Val Tyr Phe Phe Leu Phe Leu Thr
305                 310                 315                 320

Ser Phe Phe Val Ser Trp His Met Ile Ser Ile Lys Val Leu Thr Asn
                325                 330                 335

Gln Met Pro Asp Ile Glu Asn Ile Gly Lys Phe Thr Met Met Arg Asn
            340                 345                 350

Ser Val Ala Ser Gly Val Lys Ile Val Phe Ser Ile Ser Ser Gly Ala
        355                 360                 365

Phe Leu Thr Phe Tyr Ser Ile Thr Thr Thr Tyr Leu Ile Leu Ala Ile
    370                 375                 380

Leu Leu Ile Phe Phe Asn Val Leu Trp Val Cys Gln Ser Arg Ser Phe
385                 390                 395                 400
```

```
Asn Tyr Glu Asp Leu Gly Asp Val Lys Phe Gln Lys
                405                 410


<210> SEQ ID NO 23
<211> LENGTH: 335
<212> TYPE: PRT
<213> ORGANISM: Pantoea ananatis

<400> SEQUENCE: 23

Met Leu Asn Phe Lys Ser Asp Phe Ser Glu Phe Ile Thr Gly Phe Tyr
1               5                   10                  15

Leu Lys Gln Phe Thr His Leu Asn Thr Gln Glu Arg Glu His Val Leu
            20                  25                  30

Glu Thr Leu Gly Val Thr Pro Ser Ala Ile Asn Glu Phe Ile Thr Ser
        35                  40                  45

Glu Asp Ile Tyr Ile Thr Leu Pro His Ala Ser Met Asn Val Phe Phe
    50                  55                  60

Pro Arg Ala Gly Val Ser Arg Tyr Val Tyr Asp Leu Gln Asn Ser Asn
65                  70                  75                  80

Lys Asn Ala Phe His Leu Arg Phe Phe Leu Thr His Thr Asn Phe Ser
                85                  90                  95

Asp Leu Asn Trp Arg Pro Tyr Ala Trp Trp Phe Asn Asn Gly Gly Lys
            100                 105                 110

Ile Asp Lys Leu Thr Phe Phe Thr Arg Asn Lys Lys Lys Lys His Asn
        115                 120                 125

Ile Val Tyr Ser Leu Lys Pro Asn Glu Met His Ser Ala Ser Val Asp
    130                 135                 140

Arg Arg Leu Arg His Asp Phe Asp Thr Ser Met Lys Phe Lys Arg Ile
145                 150                 155                 160

Ser Leu Ser Phe Ile Tyr Met Thr Ala Val Gln Glu Val Asn Ser Gly
                165                 170                 175

Phe Ala His Lys Gly Arg Thr Leu Tyr Leu Pro Leu Asp Ala Phe Val
            180                 185                 190

Ala Phe Ile Ile His Gln Ala Lys Asn Asp Val Ile Ser Phe Asn Phe
        195                 200                 205

Leu Glu Ala Phe Leu Ser Gln Ala Gln Cys Arg Arg Leu Asn Gly Glu
    210                 215                 220

Glu Leu Ser Phe Thr Ser Glu Trp Arg Asp Ala Phe Ile Phe Asp Asn
225                 230                 235                 240

Phe Thr Asn Ile Ala Leu Leu Asn Phe Phe Gln Pro Ala Ala Phe Val
                245                 250                 255

Gly Gly Glu Lys Met Asp Asn Tyr Trp His Gln Val Ile Glu Lys Trp
            260                 265                 270

Lys Met Ala Leu Pro Asn Gln Ser Glu Val Glu Phe Ala Leu Pro Thr
        275                 280                 285

Asn Leu Val Met Pro Ala Val Gln Glu Tyr Ile Tyr Pro Tyr Lys Pro
    290                 295                 300

Ser Ser Asp Ile Ala Glu Gln Leu Ile Lys Asn Asn Ile Pro Tyr Ser
305                 310                 315                 320

Leu Thr Met Ala Ile Gln Glu His Asp Leu Phe Ser Lys Lys Glu
                325                 330                 335


<210> SEQ ID NO 24
<211> LENGTH: 159
<212> TYPE: PRT
```

<213> ORGANISM: Pantoea ananatis

<400> SEQUENCE: 24

```
Met Leu Asp Lys Ser Ala Phe Arg His Ala Met Ser His Leu Pro Thr
1               5                   10                  15

Ala Val Thr Ile Val Thr Ser Ser Gly Ser Cys Gly Ala Ala Ala Cys
            20                  25                  30

Thr Val Ser Ser Val Cys Ser Val Thr Asp Asp Pro Pro Thr Leu Leu
        35                  40                  45

Val Cys Ile Asn Arg Ala Ser Asn Asn Asn Ser Val Ile Arg Asn Asn
    50                  55                  60

Gly Ser Leu Cys Val Ser Ile Leu Ser Gly Glu Gln Ser Asn Ile Ala
65                  70                  75                  80

Met Gln Cys Ala Asn His Gln Val Ser Val Glu Glu Arg Leu Ala Leu
                85                  90                  95

Phe Asp Ala Asp Val Leu Val Thr Gly Ser Pro Ala Val Val Asp Ser
            100                 105                 110

Val Cys Cys Leu Asp Cys Arg Val Asp Asn Ile Val Glu Ser Gly Thr
        115                 120                 125

His Ser Val Phe Phe Cys Gln Val Leu Ser Ser Lys Ala Phe Val Gly
    130                 135                 140

Lys Asp Ala Leu Val Tyr Tyr Cys Arg Asn Tyr His Arg Val Ser
145                 150                 155
```

<210> SEQ ID NO 25
<211> LENGTH: 384
<212> TYPE: PRT
<213> ORGANISM: Pantoea ananatis

<400> SEQUENCE: 25

```
Met Met Lys Ser Leu Ile Ile Thr Ser His Phe Asn Ser Asp Leu Ser
1               5                   10                  15

Ser Met Ala Cys Asp Glu Phe Gly Leu Lys Arg Ser Leu Ile Phe Tyr
            20                  25                  30

Thr Pro Lys Ile Asn Glu Leu Ser Leu Gly Leu Lys Tyr Glu Tyr Tyr
        35                  40                  45

Asp Lys Ile Asp Ser Tyr Ser Val Arg Leu Met Glu Leu Gly Asn Glu
    50                  55                  60

Ile Asp Phe Ile Trp Ser Thr Ser Gly Ser Glu Ile Asn Ser Phe Ala
65                  70                  75                  80

Glu Leu Lys Ala Val Glu Leu Ala Gly Leu Arg Asn Ile Tyr Leu Gly
                85                  90                  95

Met Asn Glu Asn Ala Phe Ser Thr Ala Ala Tyr Lys Ser Ile Thr Gln
            100                 105                 110

Glu Leu Met Ala Phe Leu Gly Val Ser Ile Pro Lys Gly Leu Gln Cys
        115                 120                 125

Asn Thr Lys Lys Glu Ile His Asp Phe Leu Glu Tyr Asn Gly Gly Thr
    130                 135                 140

Ile Val Cys Lys Ala Asn Asn Gly Ala Gly Gly Val Asn Gln Phe Tyr
145                 150                 155                 160

Cys Gln Arg Phe Asp Asp Ile Tyr Lys Leu Pro His Glu Val Thr Asp
                165                 170                 175

Trp Tyr Val Glu Gln Phe Leu Lys Gly Leu Glu Phe Ser Val Asn Ala
            180                 185                 190

Tyr Met Leu Asn Gly Phe Tyr Ile Ala Ser Pro Ile Met Phe Lys Gly
```

```
        195                 200                 205

Glu Thr Asp Ile His Ser Gly His Ala Met Asp Lys Phe Arg Tyr Ile
    210                 215                 220

Ser Lys Leu Lys Asn Lys Ser Leu Asn Glu Lys Ile Asn Ala Ile Leu
225                 230                 235                 240

Ser Lys Ile Ser Asn Thr Asn Ile Phe Asn Gly Trp Ile Glu Val Glu
                245                 250                 255

Phe Ile Lys Thr His Gln Asp Leu Val Val Ile Glu Ile Asn Ala Arg
            260                 265                 270

Tyr Asn Gly Thr Ile Arg Ala Thr Gly Tyr Ala Cys Asn Glu Asn Leu
        275                 280                 285

Tyr Gln Leu Asp Leu Glu Ser Lys Ile Tyr Asn Lys Phe Ser Ser Gln
    290                 295                 300

Leu Asn His Glu Asn Glu Val Ile Glu Met Pro Ile His Leu Lys Leu
305                 310                 315                 320

Glu Thr Gly Leu Lys Glu Phe Gly Phe Val Gln Lys Met Lys Ser Arg
                325                 330                 335

Lys Thr Asn Thr Gly Arg Ala Thr Ile Trp Gly Glu Asp Gln Cys Glu
            340                 345                 350

Leu Leu Glu Arg Ile Lys Asn Thr Glu Leu Glu Ile Tyr Ser Glu Arg
        355                 360                 365

Ile Ile His Gly Ile Asn Glu Ser Lys Glu Leu Phe Glu Lys Tyr Ile
    370                 375                 380
```

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
cttgctgcag gtaggggt 18

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tctatccacg gcaaaccact 20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tgatggcctg caagacgg 18

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
tctatccacg gcaaaccact 20

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
cagcgcaaca gactggga 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
cccattccgc catgagca 18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
acggtaagat tgggcgcc 18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
ggccaacgat cgcggata 18

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
gctgctatcc ccgagataat ga 22

<210> SEQ ID NO 35
<211> LENGTH: 22
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 35
gctgaaggga ttcagacggt ta                                              22

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttaccgccac cttgctgg                                                   18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tttcgcccgt tccccttc                                                   18

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gccgtcctgc catatctcaa                                                 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
taacggactc agcatctcgc                                                 20

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cccgacccga aacaccat                                                   18

<210> SEQ ID NO 41
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
tgttcgccag gctcaagg 18

<210> SEQ ID NO 42
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
actaaaggga acaaaagctg gagctccgcc aaaaatcagc tgtg 44

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
ggatttaatt gtgaaagact ctccgctcgt g 31

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gcggagagtc tttcacaatt aaatcctcac atcagtagag g 41

<210> SEQ ID NO 45
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ctggatgatc ctccagcggg gcccccccctc gagttcatgg cgcggctttc g 51

<210> SEQ ID NO 46
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
attttattta tttaaacgtt aaacaagaaa ttcatc 36

<210> SEQ ID NO 47
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
tcctccagcg gggccccccc tcgagttgaa gcggctaact tcc 43

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
agggaacaaa agctggagct cttgtttcat ccatcatacc 40

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ttaacgttta aataaataaa attgcttgtc tcatg 35

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
ctgacggatt ttacaaacgc aaaaaccccc gcc 33

<210> SEQ ID NO 51
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
ctggatgatc ctccagcggg gcccccccctc gagtaatcgc cgcccacgcc g 51

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
actaaaggga acaaaagctg gagctcccat cattacgttt atgcc 45

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
gtttttgcgt ttgtaaaatc cgtcaggtgc ac 32

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
actatgagca cgtcggcg 18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
cgcactcccg ttctggat 18

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
caggatgagg atcgtttcgc 20

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
tcgaacccca gagtcccg 18

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
atgtatatct ccttcttaca agcttggc 28

<210> SEQ ID NO 59
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 59

-continued tctagatgca ctccaccgct gatgacatca g 31

<210> SEQ ID NO 60
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 60
atgtcatcag cggtggagtg catctagatt aaggaatcag tgaaataatt tc 52

<210> SEQ ID NO 61
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
aagcttgtaa gaaggagata tacatatgat caaaaaactt attgcag 47

<210> SEQ ID NO 62
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 62
catgagaatt aattccgggg atccgtcgac actaccatcg ggggccatc 49

<210> SEQ ID NO 63
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
ctacagcctc gggaattgct gcaggtcgac tctagatgca ctccaccgc 49